United States Patent
Krueger

(10) Patent No.: US 12,042,294 B2
(45) Date of Patent: Jul. 23, 2024

(54) SYSTEMS AND METHODS TO MEASURE OCULAR PARAMETERS AND DETERMINE NEUROLOGIC HEALTH STATUS

(71) Applicant: Wesley W. O. Krueger, San Antonio, TX (US)

(72) Inventor: Wesley W. O. Krueger, San Antonio, TX (US)

( * ) Notice: Subject to any disclaimer, the term of this patent is extended or adjusted under 35 U.S.C. 154(b) by 0 days.

(21) Appl. No.: 17/989,429

(22) Filed: Nov. 17, 2022

(65) Prior Publication Data
US 2023/0210442 A1 Jul. 6, 2023

Related U.S. Application Data

(63) Continuation-in-part of application No. 17/576,673, filed on Jan. 14, 2022, now Pat. No. 11,504,051, which is a continuation-in-part of application No. 16/903,136, filed on Jun. 16, 2020, now Pat. No. 11,490,809, which is a continuation-in-part of application No. 16/264,242, filed on Jan. 31, 2019, now Pat. No. 10,716,469, which is a continuation-in-part of application No. 15/713,418, filed on Sep. 22, 2017, now Pat. No. 10,231,614, (Continued)

(51) Int. Cl.
| | |
|---|---|
| A61B 5/00 | (2006.01) |
| A61B 3/11 | (2006.01) |
| A61B 3/113 | (2006.01) |
| A61B 3/14 | (2006.01) |
| A61B 5/11 | (2006.01) |

(52) U.S. Cl.
CPC ............ *A61B 5/4088* (2013.01); *A61B 3/112* (2013.01); *A61B 3/113* (2013.01); *A61B 3/14* (2013.01); *A61B 5/1114* (2013.01); *A61B 5/4848* (2013.01); *A61B 2562/0219* (2013.01); *A61B 2562/0223* (2013.01)

(58) Field of Classification Search
CPC ....... A61B 5/4088; A61B 3/112; A61B 3/113; A61B 3/14; A61B 5/1114; A61B 5/4848; A61B 2562/0219; A61B 2562/0223
USPC ........................................................ 600/301
See application file for complete search history.

(56) References Cited

U.S. PATENT DOCUMENTS

| | | |
|---|---|---|
| 3,616,463 A | 11/1971 | Theodore et al. |
| 4,817,633 A | 4/1989 | McStravick et al. |

(Continued)

FOREIGN PATENT DOCUMENTS

| | | |
|---|---|---|
| WO | 2013117727 | 8/2013 |

OTHER PUBLICATIONS

Allison et al. Combined Head and Eye Tracking System for Dynamic Testing of the Vestibular System. IEEE Transactions on Biomedical Engineering. vol. 43 No. 11, Nov. 1996 (USA).

*Primary Examiner* — Mohammed A Hasan

(57) ABSTRACT

A system and/or method for diagnosing a neurologic condition. The system comprises a wearable head orientation sensor, a wearable eye imaging module, and a display with a visual target. The head orientation sensor is responsive to pitch or yaw head orientation information. The eye imaging module is configured for imaging a characteristic of the retina, sclera, cornea, limbus, or pupil to determine an eye position or eye movement. An electronic circuit in the system determines an ocular parameter measurement in response to the head orientation sensor and the eye imaging module. The neurologic condition is diagnosed in response to the ocular parameter measurement.

18 Claims, 30 Drawing Sheets

Related U.S. Application Data which is a continuation-in-part of application No. 15/162,300, filed on May 23, 2016, now Pat. No. 9,788,714, which is a continuation-in-part of application No. 14/326,335, filed on Jul. 8, 2014, now Pat. No. 9,370,302, said application No. 16/264,242 is a continuation-in-part of application No. 13/749,873, filed on Jan. 25, 2013, now abandoned, said application No. 17/576,673 is a continuation-in-part of application No. 16/805,253, filed on Feb. 28, 2020, now Pat. No. 11,389,059, which is a continuation-in-part of application No. 16/351,326, filed on Mar. 12, 2019, now Pat. No. 10,602,927, which is a continuation-in-part of application No. 16/264,242, filed on Jan. 31, 2019, now Pat. No. 10,716,469.

(56) References Cited

U.S. PATENT DOCUMENTS

| | | | |
|---|---|---|---|
| 5,180,907 | A | 1/1993 | Udden et al. |
| 5,204,998 | A | 4/1993 | Lin et al. |
| 5,550,601 | A | 8/1996 | Donaldson |
| 5,555,895 | A | 9/1996 | Ulmer et al. |
| 5,621,922 | A | 4/1997 | Russ, III |
| 5,838,420 | A | 11/1998 | Donaldson |
| 5,919,149 | A | 7/1999 | Allum |
| 5,942,954 | A | 8/1999 | Galiana et al. |
| 5,953,102 | A | 9/1999 | Berry |
| 5,978,972 | A | 11/1999 | Stewart et al. |
| 6,301,718 | B1 | 10/2001 | Rigal |
| 6,796,947 | B2 | 9/2004 | Watt et al. |
| 6,931,671 | B2 | 8/2005 | Skiba |
| 7,276,458 | B2 | 10/2007 | Wen |
| 7,380,938 | B2 | 6/2008 | Chmielewski, Jr. et al. |
| 7,386,401 | B2 | 6/2008 | Vock et al. |
| 7,401,920 | B1 | 7/2008 | Kranz et al. |
| 7,448,751 | B2 | 11/2008 | Kiderman et al. |
| 7,500,752 | B2 | 3/2009 | Nashner |
| 7,509,835 | B2 | 3/2009 | Beck |
| 7,526,389 | B2 | 4/2009 | Greenwald et al. |
| 7,651,224 | B2 | 1/2010 | Wood et al. |
| 7,682,024 | B2 | 3/2010 | Plant et al. |
| 7,727,162 | B2 | 6/2010 | Peterka |
| 7,731,360 | B2 | 6/2010 | MacDougall et al. |
| 7,753,523 | B2 | 7/2010 | Kiderman et al. |
| 7,849,524 | B1 | 12/2010 | Williamson et al. |
| 7,866,818 | B2 | 1/2011 | Schroeder et al. |
| 7,931,370 | B2 | 4/2011 | Bartomeu |
| 7,988,287 | B1 | 8/2011 | Butler et al. |
| 8,232,881 | B2 | 7/2012 | Hertz |
| 8,253,814 | B2 | 8/2012 | Zhang et al. |
| 8,285,416 | B2 | 10/2012 | Cho et al. |
| 8,510,166 | B2 | 8/2013 | Neven |
| 8,529,463 | B2 | 9/2013 | Della Santina et al. |
| 8,578,520 | B2 | 11/2013 | Halldin |
| 8,696,126 | B2 | 4/2014 | Yoo et al. |
| 8,764,193 | B2 | 7/2014 | Kiderman et al. |
| 10,191,294 | B2 | 1/2019 | Macnamara |
| 10,535,151 | B2 | 1/2020 | Bleyer et al. |
| 11,504,051 | B2* | 11/2022 | Krueger ............ A61B 5/163 |
| 2002/0118339 | A1 | 8/2002 | Lowe |
| 2002/0176051 | A1* | 11/2002 | Saladin ............ A61B 3/032 |
| | | | 351/239 |
| 2004/0097839 | A1* | 5/2004 | Epley ............ A61B 5/377 |
| | | | 600/595 |
| 2006/0059606 | A1 | 3/2006 | Ferrara |
| 2006/0098087 | A1 | 5/2006 | Brandt et al. |
| 2006/0270945 | A1 | 11/2006 | Ghajar |
| 2007/0161875 | A1* | 7/2007 | Epley ............ A61B 5/4839 |
| | | | 600/595 |
| 2008/0022441 | A1 | 1/2008 | Oranchak et al. |
| 2009/0021695 | A1 | 1/2009 | Scarpino |
| 2009/0174865 | A1* | 7/2009 | Privitera ............ A61B 3/14 |
| | | | 351/246 |
| 2010/0036289 | A1 | 2/2010 | White et al. |
| 2010/0092049 | A1 | 4/2010 | Schroeder et al. |
| 2010/0101005 | A1 | 4/2010 | Cripton et al. |
| 2010/0198104 | A1 | 8/2010 | Schubert et al. |
| 2010/0280372 | A1 | 11/2010 | Poolman et al. |
| 2011/0176106 | A1 | 7/2011 | Lewkowski |
| 2011/0209272 | A1 | 9/2011 | Drake |
| 2012/0133892 | A1 | 5/2012 | Furman et al. |
| 2012/0143526 | A1 | 6/2012 | Benzel et al. |
| 2012/0194551 | A1* | 8/2012 | Osterhout ............ G06F 3/005 |
| | | | 345/633 |
| 2012/0198604 | A1 | 8/2012 | Weber et al. |
| 2012/0204327 | A1 | 8/2012 | Faden et al. |
| 2012/0297526 | A1 | 11/2012 | Leon |
| 2013/0232668 | A1 | 9/2013 | Suddaby |
| 2013/0278899 | A1 | 10/2013 | Waldorf et al. |
| 2014/0111771 | A1 | 4/2014 | Liu |
| 2014/0171756 | A1 | 6/2014 | Waldorf et al. |
| 2014/0192326 | A1 | 7/2014 | Kiderman et al. |
| 2014/0327880 | A1 | 11/2014 | Kiderman et al. |
| 2015/0038803 | A1 | 2/2015 | Uhlig et al. |
| 2015/0051508 | A1 | 2/2015 | Ghajar et al. |
| 2015/0223683 | A1 | 8/2015 | Davidovics et al. |
| 2015/0243099 | A1 | 8/2015 | Schowengerdt |
| 2015/0245766 | A1 | 9/2015 | Rennaker et al. |
| 2015/0335239 | A1 | 11/2015 | MacDougall |
| 2016/0033750 | A1 | 2/2016 | Nunnink et al. |
| 2016/0062459 | A1 | 3/2016 | Publicover et al. |
| 2016/0081546 | A1 | 3/2016 | MacDougall |
| 2016/0085302 | A1 | 3/2016 | Publicover et al. |
| 2016/0106315 | A1 | 4/2016 | Kempinski |
| 2016/0110920 | A1 | 4/2016 | Schowengerdt |
| 2016/0132726 | A1 | 5/2016 | Kempinski et al. |
| 2017/0299870 | A1* | 10/2017 | Urey ............ G02B 5/0242 |

* cited by examiner

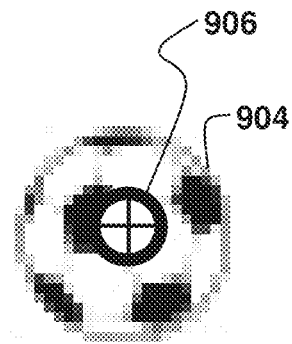
FIG. 24A　　　　　　　　FIG. 24B
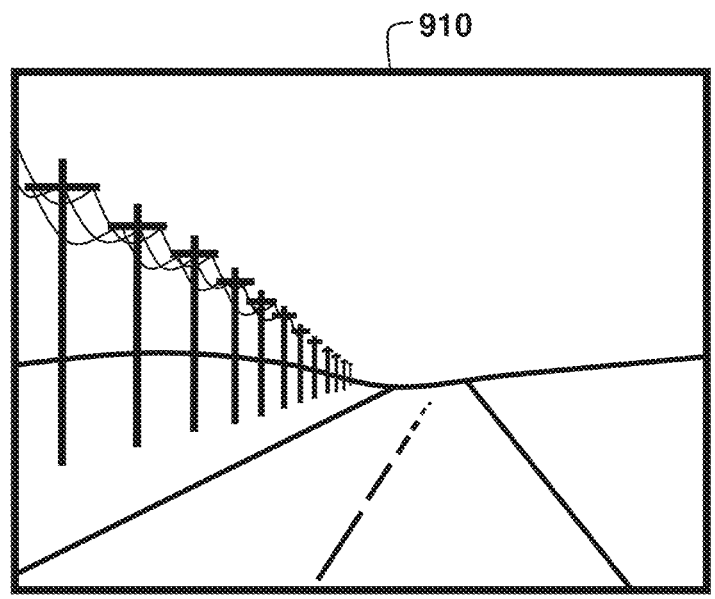
FIG. 25

SYSTEMS AND METHODS TO MEASURE OCULAR PARAMETERS AND DETERMINE NEUROLOGIC HEALTH STATUS

CROSS REFERENCE TO RELATED APPLICATIONS

This application is a continuation-in-part of U.S. patent application Ser. No. 17/576,673 by KRUEGER, entitled "SYSTEMS AND METHODS FOR OBSERVING EYE AND HEAD INFORMATION TO MEASURE OCULAR PARAMETERS AND DETERMINE HUMAN HEALTH STATUS," filed Jan. 14, 2022, which is a continuation-in-part of U.S. patent application Ser. No. 16/903,136 by KRUEGER, entitled "OCULAR PARAMETER-BASED HEAD IMPACT MEASUREMENT USING A FACE SHIELD," filed Jun. 16, 2020, which is a continuation in part of U.S. patent application Ser. No. 16/264,242 by KRUEGER, entitled "OCULAR-PERFORMANCE-BASED HEAD IMPACT MEASUREMENT APPLIED TO ROTATIONALLY-CENTERED IMPACT MITIGATION SYSTEMS AND METHODS," filed Jan. 31, 2019, now U.S. Pat. No. 10,716,469, which is a continuation-in-part of U.S. patent application Ser. No. 15/713,418 by KRUEGER, entitled "SYSTEMS AND METHODS FOR USING VIRTUAL REALITY, AUGMENTED REALITY, AND/OR A SYNTHETIC 3-DIMENSIONAL INFORMATION FOR THE MEASUREMENT OF HUMAN OCULAR PERFORMANCE," filed Sep. 22, 2017, now U.S. Pat. No. 10,231,614, which is a continuation-in-part of U.S. patent application Ser. No. 15/162,300 by KRUEGER, entitled "SYSTEMS AND METHODS USING VIRTUAL REALITY OR AUGMENTED REALITY ENVIRONMENTS FOR THE MEASUREMENT AND/OR IMPROVEMENT OF HUMAN VESTIBULO-OCULAR PERFORMANCE," filed May 23, 2016, now U.S. Pat. No. 9,788,714, which is a continuation-in-part of U.S. patent application Ser. No. 14/326,335 by KRUEGER, entitled "SYSTEM AND METHOD FOR THE MEASUREMENT OF VESTIBULO-OCULAR REFLEX TO IMPROVE HUMAN PERFORMANCE IN AN OCCUPATIONAL ENVIRONMENT." filed Jul. 8, 2014, now U.S. Pat. No. 9,370,302. And said U.S. patent application Ser. No. 16/264,242 by KRUEGER, entitled "OCULAR-PERFORMANCE-BASED HEAD IMPACT MEASUREMENT APPLIED TO ROTATIONALLY-CENTERED IMPACT MITIGATION SYSTEMS AND METHODS," filed Jan. 31, 2019, now U.S. Pat. No. 10,716,469, is a continuation-in-part of U.S. patent application Ser. No. 13/749,873 by KRUEGER, entitled "IMPACT REDUCTION HELMET," filed Jan. 25, 2013, which is a continuation-in-part of U.S. patent application Ser. No. 16/805,253 by KRUEGER, entitled "OCULAR-PERFORMANCE-BASED HEAD IMPACT MEASUREMENT USING A FACEGUARD," filed Feb. 28, 2020, now U.S. Pat. No. 11,389,059, which is a continuation-in-part of U.S. patent Ser. No. 16/351,326 by KRUEGER, entitled "OCULAR-PERFORMANCE-BASED HEAD IMPACT MEASUREMENT USING A FACEGUARD," filed Mar. 12, 2019, now U.S. Pat. No. 10,602,927, which is a continuation-in-part of U.S. patent application Ser. No. 16/264,242 by KRUEGER, entitled "OCULAR-PERFORMANCE-BASED HEAD IMPACT MEASUREMENT APPLIED TO ROTATIONALLY-CENTERED IMPACT MITIGATION SYSTEMS AND METHODS," filed Jan. 31, 2019, now U.S. Pat. No. 10,716,469. The entire disclosures of all of the aforementioned patents and applications are incorporated by reference herein.

FIELD OF INVENTION

Embodiments of the invention(s) herein relate to systems and/or methods to observe head position and/or motion, eye position and/or motion, pupil size, and/or eyeblinks and use these observations to measure ocular parameters such as saccades, vestibulo-ocular reflex, vestibulo-ocular reflex cancellation, vergence, smooth pursuit, nystagmus, dynamic visual acuity, pupil size, eye fixation, and/or eyeblinks. These ocular parameter measurements can be used to determine human health status, including:

(a) normal human health;
(b) neurologic disorders, such as traumatic brain injury;
(c) biochemical health impairments, such as alcohol and drug use, and/or
(d) physiologic health impairments, such as motion sickness, fatigue, spatial disorientation, and vertigo.

BACKGROUND

Eye and head tracking, can have significant value in determining human health such as concussions (traumatic brain injury), vision impairment, neurologic or neurocognitive disorders (NCD), alertness, and fatigue. Eye movement responses can also indicate physiologic and biochemical impairments such as impairments due to alcohol and drugs.

Historically, human health status has been diagnosed in a clinical setting. New sensors and electronic technologies enable the development of portable systems for non-clinical environments. Such advancements facilitate increases in speed and accuracy for eye and head movement observations to measure ocular parameters such as saccades, vestibulo-ocular reflex (VOR), vestibulo-ocular reflex cancellation (VORC), vergence, smooth pursuit (SP), nystagmus, dynamic visual acuity (DVA), pupil size, eye fixation, and/or eyeblinks. These ocular parameter measurements can more effectively determine human health status.

Human health status. It has been demonstrated that neurologic disorders, such as traumatic brain injury, microvascular ischemic disease, stroke, Alzheimer's disease, and Parkinson's disease can produce measurable changes in one or more of the following ocular parameters: VOR, saccades, smooth pursuit, vergence, nystagmus, eye fixation, and/or pupillometry. It has also been demonstrated that biochemical health impairments including alcohol and drug use, electrolyte, and hormone deficits (associated with dehydration, renal failure, and diabetes), and pulmonary deficits (resulting in hypercapnia or hypoxia), can cause measurable changes in one or more of the following ocular parameters: VOR, saccades, smooth pursuit, dynamic visual acuity, vergence, pupillometry, eye fixation, and/or eyeblinks. Additionally, it has been demonstrated that physiologic health impairments such as alertness/fatigue, spatial disorientation, vertigo, motion sickness, effects of electromagnetic waves due to exposure, and cardiac hypotension can cause measurable changes in one or more of the following ocular parameters: pupillometry, saccades, VOR, nystagmus, eye fixation, and smooth pursuit. Thus, having a portable device that can be used in a non-clinical environment for measuring one or more of the above ocular parameters would be highly beneficial. Each of the aforementioned human health detriments can affect different areas of the neurologic system and each of the ocular parameters to be measured can assess different anatomical regions and neural pathways of the brain. Human health status and certain health disorders or impairments may be more accurately detected by different ocular parameter measurements or by using a combination of ocular parameter measurements.

For example, the vestibulo-ocular reflex maintains eye fixation during head rotation. It is the head rotation that generates this reflex. Measurement of this reflex assesses the neural pathway response from the inner ear balance structures (e.g., utricle, saccule, semicircular canals) to the vestibular nerves, the vestibular nucleus in the brainstem (medulla and pons), and cranial nerves III, IV and VI, which move the extraocular muscles. The superior branch of the vestibular nerve innervates the lateral semicircular canal, anterior canal, and utricle. The inferior branch innervates the posterior semicircular canal and saccule. It is important to assess VOR function of each individual semicircular canal, as different impairments can affect different semicircular canals. For example, TBI can affect one semicircular canal function and not the others. Other less thorough studies, such as rotary chair testing or videonystagmography, evaluate only the function of the lateral canal. Measuring each of the semicircular canals as described herein at varying frequencies, particularly between 2 and 10 Hz is much more representative of natural head movements and can provide more information regarding impairments affecting the inner ear (e.g., vestibular, or labyrinthine impairments).

Smooth pursuit another ocular parameter, is a voluntary eye movement which requires attention on a moving visual target. It is designed to keep a moving visual target on the fovea, the region in the retina of the eye where visual acuity is highest. The goal of the smooth pursuit system is to generate eye velocities that are like the target speed, as the target is tracked. Visual information from the retina is transmitted to the middle temporal area (MT) and from this area motion signals are transmitted through the parietal sensory-motor cortex to the smooth eye movement region of the frontal eye fields (FEF) in the frontal lobe of the brain. From these 3 areas, the MT, the parietal sensory-motor cortex, and the FEF, signals are transmitted through a variety of brainstem relay nuclei to at least two regions of the cerebellum, the oculomotor vermis and the floccular complex. Following these regions, signals are then relayed to the vestibular nuclei in the brainstem and lastly project to the extraocular muscles, to move the eyes.

Saccades represent another ocular parameter and are described as rapid conjugate eye movements that are under both voluntary and reflex control. Saccades are mainly used for orienting gaze towards a visual object of interest or target. The eyes execute a series of very rapid movements from one point to another, stopping briefly at each point, the fixation point, to assess the visual image. Examples of voluntary saccades are self-directed eye movements in response to skimming a text. The sudden appearance of a peripheral visual object or an abnormal sound may evoke a reflex saccade in the direction of the stimulus. Visual information from the retina generates a signal which is sent to the primary visual cortex in the occipital lobe of the brain. Signal information is then sent to the frontal eye fields (a region in the frontal lobe), the parietal cortex and the superior colliculus of the midbrain. The superior colliculus activates the horizontal and vertical brainstem gaze centers in the pons. The horizontal gaze center and the sixth nerve nucleus allows for coordinated abduction and adduction of the eyes to shift within the horizontal axis by movement of the lateral rectus and medial rectus muscles. The vertical gaze center is in the rostral part of the midbrain which sends signals to the nuclei in the pons, which subsequently provides movement of the superior oblique, inferior oblique, superior rectus, and inferior rectus muscles. Activation of the horizontal and vertical gaze centers in concert allows for oblique eye movements. The frontal eye field of one hemisphere controls voluntary saccadic eye movements that are directed toward the contralateral visual hemifield (i.e., the right frontal eye field directs the eyes to the left).

Pupillometry is another ocular parameter, which is used to record and measure reactions of the pupil, such as size, position and movement with minute fluctuations seen in response to a stimulus. The pupillary light reflex constricts the pupil in response to light, and pupillary constriction is achieved through the innervation of the iris sphincter muscle. Light reaching the retina is converted into neuronal signals. Information travels through the optic nerve, then goes through the optic chiasm to reach the pretectal nucleus in the midbrain, where it communicates with parasympathetic nuclei in the midbrain called Edinger-Westphal nuclei, which controls the efferent pupillary pathway. Efferent parasympathetic fibers travel via the oculomotor nerve to directly innervate the iris sphincter muscles. The contraction of the iris sphincter muscles leads to pupillary constriction (miosis). It is also at the optic chiasm that some nerve fibers cross to the contralateral side of the optic tract. As a result of the crossing fibers, there is not only a direct pupillary reflex but also a consensual pupillary light reflex. The pupillary dilation pathway is a sympathetically driven response to stimuli and is a three-neuron pathway. The first-order neuron begins in the hypothalamus and descends to the spinal cord in the lower cervical area and upper thoracic area. The second-order neuron exits the spinal cord and ascends through the thorax onto the superior cervical ganglion. The superior cervical ganglion, a third-order neuron, enters the orbit via the ophthalmic division of the trigeminal nerve and ends on the dilator pupillae muscle, causing pupillary dilation.

Eye observation. As mentioned previously, ocular parameters can be measured from observations of eye and head information. Observed eye and eyelid information of interest can include horizontal eye movement (left-right when seen from the front), vertical eye movement (up-down when seen from the front), rotation of the eyes (when seen from the front), eye position, eye movement, pupil size and eyeblinks. It is desired to use a system and/or method for observing these eye parameters that is as accurate, repeatable, responsive to higher frequencies, portable, and low cost as possible. In the past, non-imaging technologies, such as detectors that used scleral coils, placed on the eye have also been used. More recently, imaging technologies that detect light information reflected off the eye and convert this light information to electrical information have become the most common technologies for eye and eyelid observation. Such imaging technologies typically have a light source and a photodetector or photodiodes. The light source can be monochromatic or polychromatic, it can be ambient or generated by the device, it can be visible, or at a wavelength that is shorter than visible (ultraviolet) or longer than visible (infrared), it can be a focused and directed beam or multidirectional. Examples of imaging technologies can include video cameras that use an array of photodetectors (typically charge conducting devices known as CCDs), video cameras that scan a beam onto an image and sense this with a photodetector (such as the broadcast video cameras in common use from the 1930s to the 1990s), and scanners that direct a beam at the eye that is then sensed with a photodetector. Imaging of the eye can be used to determine information such eyeblinks, the location and size of the pupils, and/or the location of the sclera, pupil, or other eye characteristic being measured at any time. This location information can determine gaze point and eye closure. By taking multiple successive location readings at successive times, it is possible to determine movement of the eye or eyelid as a function of time. It is desirable to have this eye and/or eyelid movement information at fast enough rates to accurately resolve human physiological behavior such as eyeblinks (which can occur at a mean rate of 17 blinks per minute when resting, 26 blinks per minute in conversation and as low as 4 blinks per minute when reading) and saccades, which can occur at a rate of 900 degrees/second and involved movements of only 0.1-0.5 degrees and generally 0.1 degree in the case of microsaccades.

Head observation. The described eye observations can be combined with head observations to determine ocular parameters such as VOR, DVA, VORC, nystagmus, SP, saccades, eye fixation, and dynamic vergence with combinations of other ocular parameters. The primary head observations of interest are pitch, which is movement of the head up and down when looked at from the front, and yaw, which is a side-to-side movement of the head when viewed from the front. The third rotation that is sometimes of interest is roll, as rotation of the head when looked at from the front. Such head rotations can easily be observed using an inertial measurement unit (IMU), which can comprise one or more accelerometers, gyroscopes, and magnetometers. Other systems and methods for observing head position and/or movement can use optical (including infrared), acoustic, ultrasonic, and laser technologies.

It is desired to overcome some of the following challenges of prior art systems and methods that use eye and head observations to assess human health status:

(a) Achieving a sufficiently high scan rate (also known as frame rate) so that high frequency movements (such as microsaccades) are captured;
(b) Accuracy and resolution of the detected eye and head position and movement;
(c) Portability;
(d) Power consumption;
(e) Cost; and
(f) Ability to be operated and used with minimal or no training.

The potential benefits of devices described herein is that they can change the standards of care and clinical recommendations by optimizing rapid evaluation and treatment. Since ocular parameters assess different areas of the central nervous system and different factors of the human health status, such systems and methods can function as physician extenders by detecting abnormalities, monitoring the recovery process, and establish rehabilitation programs to more rapidly recover from an abnormal ocular parameter detected. The technology can be applicable to any wearable platform (i.e., apparatus), such as a see-through device (face guard, glasses, face shield, augmented reality, etc.), a virtual reality device, or any related technology. Such systems and methods could determine the human health status, detect a health disorder or impairment, define the characteristics of the deficit, quantify the deficit, and wirelessly transmit this information to the wearer of the device, and/or remotely. If an abnormal ocular parameter is noted for users participating in contact sports or military personnel participating in remote areas, not only can a rehabilitation program begin earlier but an accurate monitoring strategy for decisions regarding the need for extraction or returning to play or deployment be determined. Mobile testing for clinics, hospitals, emergency departments, law-enforcement environments, urgent care centers, school facilities, on-the-field locations, or in remote areas can provide greater access for evaluation of the human health status because of its portability, lower expense, scalability, and availability of rapid and accurate results for larger numbers of individuals.

BRIEF DESCRIPTION OF THE DRAWINGS

The present invention will be better understood on reading the following detailed description of non-limiting embodiments thereof, and on examining the accompanying drawings, in which:

FIG. 24A shows an unaltered visual target;

FIG. 24B shows the visual target of FIG. 24A that has been altered by defocusing the visual target and superimposing a sharply focused target;

FIG. 25 shows a scene that can be used for optokinetic testing;

Figure 1:
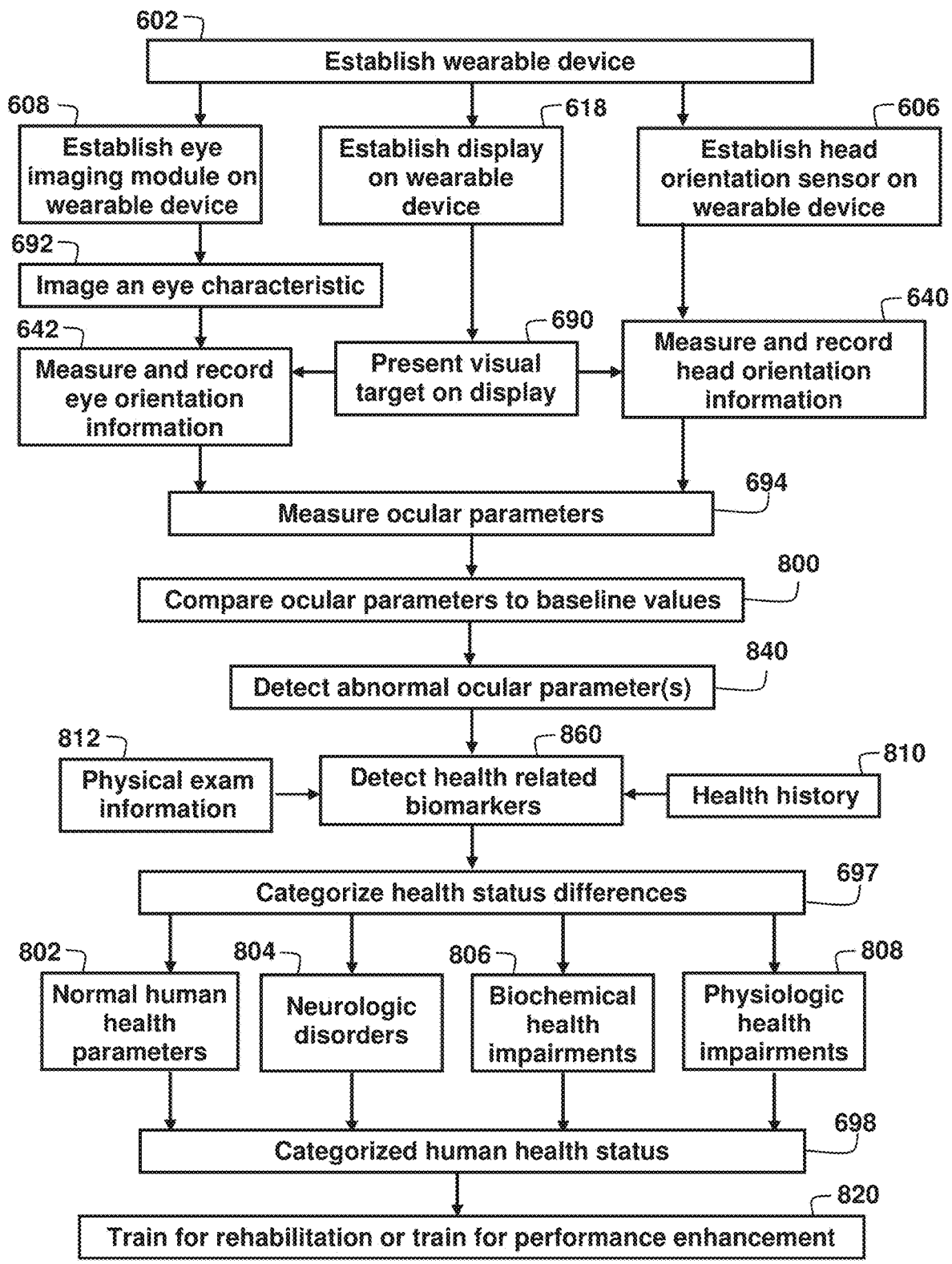
FIG. 1 is a method for observing eye and head information to measure ocular parameters and determine health status for training, rehabilitation, and/or performance enhancement.

It should be understood that the drawings are not necessarily to scale. In certain instances, details that are not necessary for an understanding of the invention or that render other details difficult to perceive may have been omitted. It should be also understood that the invention is not necessarily limited to the embodiments illustrated herein.

DETAILED DESCRIPTION

The ensuing description provides preferred exemplary embodiment(s) only, and is not intended to limit the scope, applicability, or configuration of the disclosure. Rather, the ensuing description of the preferred exemplary embodiment(s) will provide those skilled in the art with an enabling description for implementing preferred exemplary embodiment(s). It should be understood that various changes could be made in the function and arrangement of elements without departing from the spirit and scope as set forth in the appended claims.

Specific details are given in the following description to provide a thorough understanding of the embodiments. However, it will be understood by one of ordinary skill in the art that the embodiments may be practiced without these specific details.

In a preferred embodiment, the present invention comprises systems and/or methods for ocular parameter measurement that use one or more head orientation sensors and one or more eye imaging devices (sensors) integrated into a wearable platform (i.e., apparatus, device). Examples of wearable platforms can include a helmet, a face guard, face shield, a visor, eyeglasses, contact lenses, goggles, virtual reality displays, and augmented reality displays. The wearable device can comprise a display, such as an augmented reality display or a virtual reality display or could have no display. The eye sensor(s) can use an imaging device to generate eye information such as horizontal eye movement, vertical eye movement, eye position, pupil size, pupil position, pupil movement, eyelid movement (e.g., eyeblinks), static eye fixation, and dynamic eye fixation. The eye sensor can comprise an imaging device that uses at least one opto-electric transducer that converts light signals into electrical signals and is configured for imaging eye and or eyelid characteristics at a plurality of times to create a moving image of the eye or eyelid. The system/methods can combine the eye information and head orientation information to measure ocular parameters such as saccades, vestibulo-ocular reflex (VOR), vestibulo-ocular reflex cancellation (VORC), vergence, smooth pursuit (SP), nystagmus, pupil size, dynamic visual acuity (DVA), and/or eyeblinks. The systems/methods can be configured to determine a human health status such as normal health, a neurologic disorder, a biochemical impairment, and/or a physiologic impairment. Embodiments of the systems and methods can be portable and can be deployed in a non-clinical setting.

The following table shows examples of the relationship between health categories (disorders or impairments) and the underlying causes, and measurable ocular parameters.

| Human health category | Underlying human health cause | Measured ocular parameters |
| --- | --- | --- |
| Neurologic disorder that is always neurocognitive | Alzheimer's disease | Saccades<br>Smooth pursuit<br>Pupillometry<br>Eyeblinks |
| Neurologic disorder that is almost always neurocognitive | Traumatic brain injury (Example: concussions) | VOR<br>Saccades<br>Smooth pursuit<br>VORC<br>Vergence |
| Neurologic disorder that can also be neurocognitive | Microvascular ischemic disease | VOR<br>Saccades<br>SP |
| Neurologic disorder that can also be neurocognitive | Stroke | Pupillometry<br>Spontaneous nystagmus |

| Human health category | Underlying human health cause | Measured ocular parameters |
|---|---|---|
| Neurologic disorder that can also be neurocognitive | Parkinson's disease | Saccades<br>Smooth pursuit<br>VORC<br>Pupillometry |
| Neurologic disorder that can be neurocognitive | Multiple sclerosis | Saccades<br>VOR<br>Pupillometry |
| Neurologic disorder that can be neurocognitive | Brain lesion | Smooth pursuit<br>VORC<br>Saccades<br>Optokinetic nystagmus |
| Neurologic disorder that can be neurocognitive | Epilepsy | Saccades<br>Vergence<br>Pupillometry |
| Neurologic disorder that can be neurocognitive | Amyotrophic lateral sclerosis | Smooth pursuit<br>Nystagmus<br>Eye fixation |
| Biochemical health impairment | Alcohol in the blood | VOR<br>Saccades<br>Smooth pursuit<br>DVA<br>Vergence |
| Biochemical health impairment | Drug use | Pupillometry<br>Saccades<br>Vergence<br>VOR |
| Biochemical health impairment | Metabolic deficits such as electrolyte deficits or hormonal deficits (diabetes, etc) | Smooth pursuit<br>Saccades<br>Pupillometry<br>Eyeblinks<br>Spontaneous nystagmus |
| Biochemical health impairment | Pulmonary deficits such as increased $CO_2$ or decreased $O_2$ | Eyeblinks<br>Saccades<br>Pupillometry |
| Physiologic health impairment | Fatigue/lack of alertness | Pupillometry<br>Eyeblinks<br>Saccades |
| Physiologic health impairment | Spatial disorientation | Optokinetic nystagmus<br>Saccades<br>VOR |
| Physiologic health impairment | Vestibular motion sickness and/or Kinetosis | Vestibular nystagmus<br>VORC<br>Saccades<br>Smooth pursuit |
| Physiologic health impairment | Visual motion sickness | Saccades<br>VORC<br>Smooth pursuit<br>Optokinetic nystagmus |
| Physiologic health impairment | Deficits related to electromagnetic wave exposure (Havana syndrome) | VOR<br>VORC<br>Smooth pursuit<br>Saccades<br>Vergence |
| Physiologic health impairment | Cardiac deficits such as hypotension | Saccades<br>Pupillometry |
| Physiologic health impairment | Dizziness related to labyrinthine impairments and/or central nervous system disorders | VOR<br>VORC<br>Saccades<br>Vestibular nystagmus |

As shown in this table, neurologic disorders affecting different areas of the central nervous system, may require different ocular parameter measurements to detect an abnormality. The ocular parameter being tested must involve the neurologic pathway which was affected by the disorder. Additionally, certain health disorders have characteristic ocular parameter abnormalities. For example, abnormal microsaccade rates have been observed in numerous human health disorders or impairments. Here are some further examples:

a. TBIs/Concussions have been associated with abnormalities of smooth pursuit, saccades, near point of convergence (NPC) distance, the vestibulo-ocular reflex (VOR) and vestibulo-ocular reflex cancellation (VORC). Cognitive deficits can also result from TBI. VOR remains most sensitive and vulnerable to TBI of all severities. Dizziness is one of the most common symptoms following head trauma and can serve as a primary predictor of a prolonged recovery. The symptoms of dizziness associated with TBI can be either due to central nervous system (CNS) or peripheral (e.g., vestibular) deficits or both, although peripheral disorders are much more common. Therefore, VOR testing is paramount to accurately assess the neurologic pathway involving the vestibular system to detect a TBI.

b. Dizziness is a broad symptom and, as noted above, can be related to inner ear labyrinthine impairments, such as Meniere's Disease or vestibular dysfunction. Dizziness can also be related to disorders of the central nervous system, such as with a stroke, concussion/TBI, or microvascular ischemic disease. Dizziness is described as a feeling of imbalance, unsteadiness, wooziness, or not being clear-headed. Vertigo is a symptom of illusory movement, especially rotation and often has also been described as a sense of swaying or tilting or may be perceived as a sense of self motion or motion of the environment. Like dizziness, vertigo can be associated with a central nervous system disorder or with a labyrinthine impairment. VOR, VORC, saccades, and/or presence of vestibular nystagmus can be assessed to detect the associated deficits with these disorders or impairments.

c. Motion sickness is a common impairment with symptoms of nausea, vomiting, unsteadiness, and perceived motion with a decay in human performance. Motion sickness can be induced by either vestibular stimulation, such as with body or head rotation (e.g., vestibular motion sickness) or visual stimulation (e.g., visual motion sickness), such as with the use of virtual displays or full field optokinetic stimulation. For example, symptoms can occur in movement evoked environments, such as in a centrifuge or on a roller coaster with no visual input. Alternatively, while a subject is stationary and immersed in a virtual reality display, the visual stimulus can cause symptoms which can be more acute, as all external reference points are blocked from vision, the simulated images are three-dimensional, and in some cases, stereo sound can even contribute to the sense of motion. The stimulation causing the motion sickness symptoms can also be a combination of vestibular and visual stimulation (e.g., kinetosis). Ocular parameters, such as VORC, saccades, smooth pursuit, eye fixation, and presence of optokinetic nystagmus can detect abnormalities associated with these impairments.

d. Many neurologic disorders, such as Alzheimer's Disease, or other neurocognitive disorders resulting in mental deficits, can be detected early by measurement of ocular parameters. Alzheimer's Disease is the single most common cause of dementia and, accounts for most all neurocognitive disorders. Alzheimer's Disease affects the hippocampus first and is the part of the brain most severely affected by the condition. Alzheimers Disease then moves through stages with symptoms worsening over time, as the neuron damage spreads throughout the cortex of the brain. Alzheimer's Disease is associated with eyeblink abnormalities and reduced pupil diameter. However, the most common abnormalities include the saccadic dysfunction, fixation instability, and abnormal smooth pursuit. In the early stages of Alzheimer's disease, detection can be established by eye-tracking and measurement of ocular parameters, such as saccades, smooth pursuit, pupillometry, eye fixation, and eyeblinks, when missed by traditional cognitive assessments.

e. Individuals with multiple sclerosis having lesions in the brainstem (medulla and pons) can have difficulty tracking objects while the head is in motion or when they are observing a moving target. Because of the vestibular nucleus being involved, detection can be easily determined with measurement of an ocular parameter such as the VOR and saccades.

f. Substance abuse with drugs and alcohol are associated with poor cognitive function with tests of verbal memory, visuospatial functioning, psychomotor speed, working memory, attention, cognitive control, and overall IQ. Alcohol has been shown to have diverse effects, including decreased velocity of both saccadic and smooth pursuit eye movements, increased saccadic latency, impairments of convergence, and impairments of the VOR. The number of fixations and the duration of eye fixations can also be increased significantly as a function of increased breath alcohol concentration. These effects contribute to impaired visual information processing, which reduces driving ability. Barbiturates have been reported to produce effects like alcohol, and the effects of benzodiazepines and opioids seem to be more limited but still substantial. Heavy alcohol use has been associated with decreases in gray matter, attenuated increases in white matter volume with deficits in the hippocampal area, resulting in changes with memory and deficits in the cerebellum, resulting in changes with balance. Ocular parameter measurements also show slowed eyelid closure coupled with increased duration and frequency of closure with drowsiness, fatigue, and inattentiveness.

g. While neuropsychological testing traditionally has been used to measure cognitive performance and processing deficits in the past, the cerebral influences on the ocular motor system provides another quantitative method to assess these deficits more accurately and objectively. The eye and its purposeful movements can also represent an opportunity into evaluation of higher functions of the brain. Quantification of cerebral function using neurobehavioral tools is the gold standard, but it can be difficult to assess in some patients whose subjective responses may not always be reliable. Abnormal eye movements can precede detection of neurocognitive disorders before neuropsychological cognitive testing and can accurately assess different cognitive domains. The cognitive control of eye movements requires synchronization of circuits between frontal and parietal cortex as well as subcortical nuclei to produce appropriate context-specific responses. The oculomotor networks substantially overlie the hemispheric attentional systems in frontal, temporal, and parietal lobes interacting at many levels. Cognitive processes are most readily examined with saccades, smooth pursuit and pupillometry when measuring ocular parameters. Extended reality (XR) and 3-D displays can be designed to provide a rehabilitation prescription (e.g., a type of electronic prescription) to improve specific cognitive visual deficits or cognitive domains. The use of such visual displays and measuring ocular parameters can provide information of the cognitive function as well as quantify the degree of the neurocognitive deficit detected. The use of eye and head movement information described in this document can be valuable in cognition evaluation, care, management, and long-term planning for anyone suspected as having a neurocognitive disorder.

h. Other abnormal physiologic properties, such as cardiac, pulmonary, and other central nervous system measures can adversely affect the ocular parameters and such measurement of these parameters can provide a method to detect an abnormality. For example, cardiac disease not only can affect the vessels seen on the retina but can have abnormal ocular parameter measures such as with pupillometry and saccades. In military and civilian aviation, it is well known that visual performance is negatively affected by hypoxia, and the visual system has been shown to serve as a means of monitoring the central nervous system and detecting brain states. It is also associated with an increase of heart rate and blood pressure to combat the reduced oxygen in the blood and maintain adequate tissue oxygenation as well as cognition. Hypoxic-ischemic encephalopathy has been associated with asymmetric eye movements, slow gaze shift from one target to another and disturbance of gaze stabilization. Even abnormal biochemical impairments of hormones, electrolytes, metabolites, and gases can result in abnormal eye movements, which can be detected with ocular parameter measurements. For example, high cortisol can be the trigger for adrenal stress symptoms and related long-term health problems. Cortisol levels have a profound effect on our eyes and vision. Some of the symptoms that can occur include double vision, sensitivity to bright light, difficulty focusing up close, memory issues, and blurred vision. Low cortisol levels can trigger sleeplessness and fatigue, both which can affect ocular parameter measurement.

i. Loss of sodium and dehydration can lead to impaired mental function, fatigue, impaired vision, changes in the cornea and decreased brain volume, all which can also affect the ocular parameter measures. There are numerous metabolic disorders which can result in visual disturbances and can have characteristic ocular findings that assist in their diagnosis. Corneal opacities, cataracts, cherry-red spot, and retinal degeneration may be the earliest signs of many metabolic disorders. As they structurally affect the anatomy of the eye, they can also affect the ocular parameter measurements. Symptoms can also be the result of the toxic effects of accumulating metabolites or deficiencies in the central nervous system.

Based on the foregoing, it should be apparent that wearable systems and methods that measure ocular parameters can be valuable for assessing human health status.

Definitions

The definitions that follow apply to the terminology used in describing the content and embodiments in this disclosure and the related claims.

Artificial intelligence (AI) is defined in this document and embodiments as a computer system program which attempts to implement aspects of human-level intelligence, in which a machine can learn and form judgements to improve a recognition rate for information as it is used. AI can behave in ways that both mimic and go beyond human capabilities. AI-enabled programs can analyze and contextualize data to provide information or automatically trigger actions without human interference. Artificial intelligence technologies include a machine learning (or more advanced deep learning) technology that uses an algorithm that classifies/learns the characteristics of input data by itself and an elemental technology that simulates functions such as recognition or judgment, like the human brain. The elemental technology can include a visual comprehension technique for recognizing objects as in human vision.

Angular velocity is defined as speed of a physical object that is moving along a circular path. The angular velocity of an object is the object's angular displacement with respect to time. Angular velocity is the rate of change of the position angle of an object with respect to time, so $w=theta/t$, where $w$=angular velocity, theta=position angle, and $t$=time. Angular velocity, also called rotational velocity, is a quantitative expression of the amount of rotation that a spinning object undergoes per unit time. It is a vector quantity, consisting of an angular speed component and either of two defined directions or senses.

Augmented reality (AR) is defined as technology that superimposes a computer-generated image on a user's view of the real world, thus providing a composite view. This superimposed digital overlay can, in a limited manner, interact with the environment in real-time but users cannot interact with it like they would be able to in real life. Mixed reality (MR) is a type of augmented reality in which real and virtual worlds are combined to produce new environments and visualizations where physical and digital objects coexist and interact. In this document, the terms AR and MR are used synonymously as both represent visual display systems. Extended reality (XR) in this document is an umbrella term incorporating AR, VR and MR display systems.

Biochemical health impairment is defined as an impairment of production, regulation, structure, levels, or physical properties of the biological or chemical nature of hormones, immunoglobulins, electrolytes, gases, or metabolites. This would include proteins, carbohydrates, lipids, and nucleic acids, the mechanisms of enzyme action, the chemical regulation of metabolism, the chemistry of nutrition, the molecular basis of genetics (inheritance), the chemistry of vitamins, energy utilization in the cell, and the chemistry of the immune response. Most biochemical diseases affect the brain, and many lead to mental deficits, developmental delays, behavioral problems, or neurologic handicaps. For example, the brain requires certain levels of neurotransmitters to function. They are the molecules used by the nervous system to transmit messages between neurons, or from neurons to muscles. Biochemical health impairments associated with mental disorders have included abnormalities of hormones such as serotonin, dopamine, norepinephrine, and gamma-aminobutyric acid (GABA). The hypothalamic-pituitary-adrenal axis (HPA axis), is responsible for the release of vanous hormones, including cortisol, which regulate the stress response. Additionally, toxic drugs can impair the biochemical health of humans. For example, exposure to cocaine before birth may affect the way a child's brain functions many years later, due to alterations in metabolic processes that enable brain cells to use energy and function properly. Biochemical impairments which affect brain function can be detected when they cause abnormal effects on the neural pathways in the brain which are related to the ocular parameter being measured. Examples of biochemical impairments include, but are not limited to, hypoxemia, Addison's disease, inebriation, and drug overdose.

Biometrics can be defined as measurable physical characteristics or personal behavioral traits used to identify, or verify the claimed identity of, an individual. Iris characteristics, facial images, fingerprints, voice recognition, behavior characteristics and handwriting samples are all examples of biometrics which can be captured visually and/or electronically with various sensors and analyzed. Fundamentally biometrics involve any metrics related to human features.

A classifier (or machine learning classifier) is defined as an algorithmic computer vision tool that takes an input data frame (an image for example), processes the pixel-level information against a target, and outputs a result. A classifier attempts to identify a pattern within the pixels in the image and compares that pattern to its target set. Classifiers can be of a machine learning type (such as a convolutional neural networks or general adversarial networks) or of a static type (such as Haar cascades), and typically require some form of training for optimization.

Clock generators are defined as integrated circuits (ICs) that generate timing signals for electrical circuits. MEMS clock generators use micro-electromechanical systems (MEMS) technology. Clock generators typically use oscillators, which typically work on mechanical resonance, and can therefore be called resonators. They can use phase locked loops (PLLs) to produce selectable or programmable output frequencies. Clock generators can generate one output or multiple outputs that supply timing signals for electronic systems that require multiple frequencies or clock phases.

Cognition is defined as the mental action or process of acquiring knowledge and understanding through thought, experience, and the senses. It encompasses various aspects of high-level intellectual functions and processes such as attention, memory, knowledge, decision-making, planning, reasoning, judgment, perception, comprehension, language, and visuospatial function. Cognitive processes are defined as encompassing all information processing eyen at the subconscious level or as the ability to think and reason. Other related cognitive processes are concept formation, pattern recognition, imagery, and problem solving. Measurements of human eye movements have been shown to provide information of cognition, cognitive processing, and cognitive disorders.

Cognitive disorders are defined as any disorder disease, or condition that significantly impairs the cognitive functioning of the person to the point where normal functioning in society is impossible without treatment. These disorders are commonly detected by ocular parameter measurements. There are various causes of these disorders including traumatic brain injuries, infectious diseases or other diseases of the brain, drug effects, lifestyle factors and abnormal metabolic and/or hormonal factors which have an adverse effect on the brain. Genetic influences also play a role in many different cognitive disorders. In this document and embodiments, cognitive disorders are a part of neurocognitive disorders. Alzheimer disease is the most well-known disorder associated with cognitive impairment. The use of eye position and eye movement measurements, related to eye fixation, can be used to assess cognitive disorders, and provide key treatment approaches. Visual and cognitive processing occurs during eye fixations which makes vision-based testing, such as with ocular parameter measurements, vital as a sensitive approach in the initial evaluation of cognitive disorders. For example, VOR, smooth pursuit, vergence, and VORC can be used to detect cognitive deficits or neurocognitive disorders. Additionally, other major eye movement parameters, such as fixations, saccades, eye-blinks, and pupillary measurements can provide distinct information about cognitive effort in response to task demand. Measures of cognition can include analytic comparison of movements and/or positions between the eyes and target status, or between the head, eyes and target status.

A concussion is a traumatic brain injury that results in temporary loss of normal brain function. It is characterized by immediate and transient alteration in brain function, including alteration of mental status or level of consciousness, that results from mechanical force or trauma. Concussions can be caused by direct trauma to the head, such as from falling, getting hit or being in an accident. They can also occur because of rapid acceleration-deceleration of the head, such as in whiplash injuries or blast injuries, such as in a war zone. A concussion can affect memory, judgment, reflexes, speech, balance, and muscle coordination and is associated with abnormal ocular parameter measures. In this document, it is used interchangeably with traumatic brain injury (TBI).

A convolutional neural network (CNN) is defined as a deep learning neural network designed for processing structured arrays of data such as images. Convolutional neural networks (CNN) are widely used in computer vision and many visual applications such as image classification. The CNN contain many convolutional layers stacked on top of each other and each layer processes an incoming image such that the series of layers progressively identify more complex features.

Corneal reflex is defined as an eye blink, a functional activity of the eye, in response to tactile stimulation of the cornea. More specifically, it is a contraction of the orbicularis oculi in response to light touch of the cornea. It is polysynaptic, the afferent limb of the reflex being the ophthalmic division of the fifth cranial nerve, the efferent limb running in the seventh nerve. Absence of the reflex can be associated with specific diseases affecting the central nervous system.

The cornea is defined as the circular transparent layer that covers the pupil, iris and anterior chamber of the eye and is the anterior one-sixth of the fibrous layer of the eyeball. The cornea is noticeably more convex to the outside than the sclera and is a completely avascular structure. The cornea is horizontally oval, measuring 11-12 mm horizontally and 9-11 mm vertically. The average corneal horizontal diameter (white to white) is $11.71 \pm 0.42$ mm. The cornea is convex and aspheric with an anterior curvature of 7.8 mm and posterior curvature about 6.5 mm. There is a gradual increase in thickness from central cornea to the periphery. Alteration in tissue thickness is due to increase in the amount of collagen in the peripheral stroma and the thickness is found to decrease with age. These corneal characteristics can be used for eye tracking, as beams of light striking the cornea create a reflection (e.g., a glint), while the eye imaging module images, records and tracks the position, orientation and movement of the eye. Numerous corneal reflections (glints) can offer high resolution imaging of the pupil and cornea.

Donder's Law of ocular motility states that the orientation of the eye as a whole is determined by the position of the fixation line. Each time the fixation line returns to the same point, no matter by what trajectory, the eye always reassumes the same orientation.

Duction of eye movement refers to the rotation of one eye independently of its fellow. A prefix can be attached to this word to indicate the direction in which the eye is rotated.

Dynamic eye fixation is defined as the ability to fixate on a visual target of interest, which is in motion. Static eye fixation refers to the ability to fixate on a stationary visual target of interest. In normal human activities, when viewing objects in the visual field, the head has natural motion or has movement and we follow moving objects or observe stationary visual targets of interest, while we are in motion. When observing a visual object of interest, it is important to have a focused position of the eye on the visual object when these objects are stationary or in motion, and the head is in motion. Our ability to maintain dynamic and static fixation on these visual targets while we are in motion, performing our daily activities, can provide a measure of human performance.

Dynamic visual acuity (DVA) in this document is defined as an ocular parameter measurement to quantify the visual impairment (i.e., visual acuity loss) while viewing a stationary visual target and moving the head. The total visual acuity lost (i.e., DVA loss) due to dynamic movement of the head is calculated by identifying the total difference in visual acuity between dynamic and static conditions (i.e., DVA—static visual acuity [SVA]). In subjects with a normal functioning VOR, minimal loss of visual acuity occurs between dynamic and static conditions. Visual acuity, also known as clarity of vision or sharpness of vision, refers to a person's ability to see small details.

Dynamic Visual Acuity Testing (DVAT) is defined as a computerized VOR assessment method to evaluate the peripheral vestibular system during head movements, and specifically assesses visual acuity during head movement relative to baseline static visual acuity. In this document DVAT represents DVA. In normal individuals, losses in visual acuity are minimized during head movements by the vestibulo-ocular system that maintains the direction of gaze on an external target by driving the eyes in the opposite direction of the head movement. When the vestibulo-ocular system is impaired, visual acuity degrades during head movements. Adequate function of the peripheral vestibular system, specifically the vestibulo-ocular reflex (e.g., a network of neural connections between the peripheral vestibular system and the extraocular muscles) is essential for maintaining stable vision during head movements. Decreased visual acuity resulting from an impaired peripheral vestibular system may impede balance and postural control and place an individual at risk of falling. Reduced visual acuity, as documented with DVA testing, is significantly reduced in individuals with vestibular deficits and is an important ocular parameter measurement used to detect other human health disorders, impairments, or deficits.

Electromagnetic exposure refers to human tissue penetrated by electromagnetic fields (EMF) or electromagnetic radiation (EMR). Moving electric charges produce both electric and magnetic fields. The properties of electromagnetic radiation depend strongly on its frequency, and the frequency is the rate at which the radiating electromagnetic field is oscillating. Frequencies of electromagnetic radiation are given in Hertz (Hz), with radio frequency (RF) being on the lower end and gamma-ray being on the upper end of the electromagnetic spectrum. These waves of electric and magnetic energy moving together, can cause damaging electromagnetic effects to human health. The electromagnetic harmful effects, to the human body are characterized by the presence of a wide spectrum of non-specific multiple organ symptoms, disorders, and impairments, typically including the central nervous system following acute or chronic exposure to the electromagnetic field or radiation. More specifically, exposure to electromagnetic fields can induce changes in calcium signaling cascades, activate free radical processes, cause fractures of DNA, alter hormone production, and overproduce reactive oxygen species (ROS) in living cells as well as alter neurological and cognitive functions and disruption of the blood-brain barrier. Autonomic nervous system effects of EMF/EMR could also be expressed as symptoms in the cardiovascular system. Other common effects of EMF include effects on skin, microvasculature, immune and hematologic systems. Individuals can have neurologic, neuro-hormonal and neuro-psychiatric symptoms following exposure to EMF/EMR because of neural damage and over-sensitized neural responses. More recently, suspected electromagnetic exposure has been suspected with the "Havana Syndrome", when individuals reported hearing strange sounds before feeling ill. Symptoms of exposure include headaches, vestibular disturbances such as dizziness and disorientation, ear pain, tinnitus, fatigue, confusion, insomnia, difficulty focusing, and cognitive deficits. Examination of these individuals have exhibited an array of oculomotor visual findings including convergence insufficiency, abnormal smooth pursuit, and saccadic dysfunction impairment of the vestibulo-ocular reflex. The use of head and eye tracking can provide relevant ocular parameter measurements, as described in this document, to detect abnormalities associated with this physiologic health impairment Extended reality (XR) is defined as an umbrella term incorporating virtual reality (VR), augmented reality (AR), and mixed reality (MR).

Eye characteristics in this document and embodiments are defined as the anatomic features or distinguishing characteristics of the eye, including the sclera, cornea, limbus, iris, pupil, eyelid and retina. Each of these eye characteristics can be imaged by an eye sensor and used to measure ocular parameters and each of the characteristics can be used to determine the position, movement, orientation, and functional activity of the eye to determine the human health status, such as normal health, neurologic disorders, physiologic and/or biochemical impairments.

Eye correcting algorithm (ECA) is an algorithmic computer vision tool. It builds upon a classifier by attempting to account for movement between the opto-electric transducer itself and the eye being observed. This movement is typically referred to as slippage and the ECA takes the input data frame (the same image as the classifier), processes the information to determine appropriate offsets, and supplies the offset parameters as its output.

Eye Fixation or visual fixation is defined as maintaining the visual gaze on a single location, point of gaze, or gaze point. It is the stationary eye position between eye movements or saccades when observing a point target. More specifically, it refers to a collection of relatively stable gaze points that are near in both spatial and temporal proximity. During fixation, the eyes hold steady on an object, and thus fixation reflects attention to a stimulus and strongly correlate with task performance. Because task performance is also correlated with effort expenditure, there is a link between fixation frequency and cognitive effort. Fixations are those times when our eyes essentially stop scanning about the scene, holding the central foveal vision in place so that the visual system can take in detailed information about what is being looked at. Fixations are brief pauses from scanning a scene to gather a more comprehensive idea of what is being viewed. The eye remains relatively still, spending time in one location to understand the visual world. Most fixations last between 50-600 ms, but the amount of time spent on a specific fixation is dependent on both the task and stimulus. Eye fixation measurement includes the duration of the point of gaze. Fixations are excellent measures of visual attention and visual fixation ability on an object of interest, while the head is stationary or in motion and in this document can be an accurate and predictable measure of human performance and the human health status.

An eye imaging module in this document and embodiments can also be an eye imaging device and can be defined as any mechanical, digital, or electronic apparatus for recording, storing, or transmitting visual images. Examples include still cameras, video cameras, and scanners. Imaging devices can comprise light sources, lenses, prisms, mirrors, and other means for converting images or light paths. These means for converting the image or light path can be passive or could be active, an example would be a micro-opto-electromechanical system (MOEM). Imaging devices also typically comprise a detector. The detector could be a photodectors (e.g., an opto-electric transducer) which converts the optical signal into an electric signal. It could also be an array of electro-optical sensors, such as the charge conducting device (CCD) arrays found in some video cameras. Other imaging devices include CMOS imagers, SPAD sensors, global shutter image sensors, single photon sensitivity sensors, high frame rate image sensors, high dynamic range sensors, low voltage and low power imagers and imaging system-on-a-chip. In this document and embodiments, eye tracking, eye sensor, eye imaging module, and/or eye orientation sensor all represent an eye imaging device, and the terms may be used interchangeably to represent measurements of eye movement, eye gaze position at any given time and measures of any of the eye features as described herein.

Eye tracking is defined as the process of measuring where we look, also known as point of gaze or gaze point. A light source, such as near-infrared light, is directed towards the center of the eyes (pupil), causing detectable reflections in both the pupil and the cornea (the outer-most optical element of the eye). These resulting reflections, the vector between the cornea and the pupil, are tracked by an infrared camera. This is the optical tracking of corneal reflections, known as pupil center corneal reflection. The pupil provides information of gaze direction and glints inform eyeball location. These measurements can be carried out by an eye sensor or sensing device, such as an imaging device comprised of an opto-electric transducer that detects the position and movements of the eye and converts the light signal to an electric signal.

Eyeblinks are the action of closing and re-opening the eyes (e.g., eyelid movement). Eyeblinks are either voluntary, involuntary (such as a spasm), or reflex blinks (evoked by an external stimulus). A voluntary eyeblink involves cortical control. Blink patterns can be comprised of incomplete or partial blinks, prolonged eyelid closure time and short blink intervals. When the eyes are closed during a blink, there is no incoming visual information to process. Eyeblinks can indicate changes in attention, fatigue, and cognition. Specifically, eyeblink characteristics in this document include the frequency of eyeblinks or eyeblink rate, the amplitude, velocity of blinks, blink latency, and the duration of blinks which can be measured to detect different human health disorders or impairments. Eyeblink in this document is used as an ocular parameter measurement to determine eyelid performance and/or function and detect normal human health and human health abnormalities, such as a neurologic disorder, biochemical impairment, and/or physiologic impairment such as fatigue.

Eyelid movement is defined as the motion of the eyelid (e.g., also called an eyeblink) to position the eyelid in a particular place. More specifically, it is related to the velocity of an eyeblink, the duration of the eyeblink, the amplitude, as well as the frequency of eyeblinks, and whether the eyeblink is voluntary, involuntary, or reflexive during the upward or downward motion to position the eyelid in a specific location.

Eyelid position is defined by its location and as being normal when in primary gaze (e.g., binocular fixation while looking straight ahead). For example, in the resting position the eyelid position may be open, partially open or closed. The upper eyelid is positioned about 1 to 2 mm inferior to the superior limbus. Measured in another manner, the normal upper eyelid position in an individual may be up to 5.5 mm above the mid-pupil (or center of the cornea).

Eyelids are thin folds of skin that cover and protect an eye. The eyelid is made up of several layers; skin, orbicularis oculi muscle (main protractor muscle which closes the eyelid), tarsal plate, levator muscle apparatus (which lifts the eyelid, exposing the cornea), and palpebral conjunctiva. The orbicularis oculi muscle helps with both voluntary closure (sleep) and involuntary closure (blink). The muscle also expels tears and debris through the nasolacrimal duct via the two puncta in the upper and lower lids. The tarsal plate is the connective tissue and main structural component of the eyelid. The palpebral conjunctiva is a thin mucous membrane on the inside of each lid. The eyelids also contain glands (Meibomian glands and glands of Zeis and Moll) that secrete substances responsible for lubricating the ocular surface. The human eyelid features a row of eyelashes along the eyelid margin, which serve to heighten the protection of the eye from dust and foreign debris, as well as from perspiration. The names "palpebral" (and "blepharal") also refer to the eyelids. The key function of the eyelid is to regularly spread the tears and other secretions on the eye surface to keep it moist, since the cornea must be continuously moist. The blink reflex protects the eye from trauma or foreign bodies and with each blink the cornea and conjunctiva are swept of debris and relubricated. Both the upper and lower eyelids have rich vascular supply and have many anastomoses between the upper and lower lid circulations. In this document and embodiments eyelid characteristics (which include eyeblinks) can be used to determine the human health status, such as physiologic and/or biochemical impairments and/or neurologic disorders.

A face shield is a device or item of personal protective equipment (PPE), which aims to protect the wearer's entire face (or part of it) from trauma, injury or hazards. In this document and the appended claims, face shields, visors, goggles, and eye shields are used synonymously. These devices can be attached to a helmet or worn separately and can function as a display for displaying visual targets to the user or can be comprised of an extended reality device to view visual targets for ocular parameter measurements.

Focused position of the eyes is defined as the position or orientation of the eyes to provide a clear image of a visual element, visual object, or target of interest on the fovea. In this document and embodiments, it is also referred to as eye fixation, gaze point or point of gaze during a fixation, to provide the highest quality of visual acuity. It is used as an important ocular parameter measure to determine human health status.

Foveated rendering is defined as a process which renders most of the view into a virtual world at lower resolution, except for the exact area directly in front of user's gaze. The gazed area is rendered at a higher resolution. More specifically, foveated imaging uses a digital image processing technique in which the image resolution varies across the image according to the user's gaze, and a foveated display is therefore designed to function in the context of user gaze. The wearable device can then use a display with regions of lower and higher resolution to reduce power consumption and information bandwidth needed for the display. The electric circuit carrying the information may be shared by lower and higher resolution portions of a display, or different portions of a display with different resolutions may be supplied with different electric circuits carrying the information. Foveated rendering can be used in extended reality (XR) applications by using a foveated display and an eye tracking system to monitor the gaze of the user, and to optimize rendering to focus only where the user is actively looking on a display. If the focused position of the eye is determined, the display can show the higher-resolution picture in the individual's direct view, and the lower resolution information remains in the remainder of the display. The result is improved latency and computations.

Functional activity of the eye is defined broadly as the ocular parameters and other eye activity described herein, which provides visual function to maintain good visual acuity. Measurements of functional activity include the ocular reflexes, eye gaze position or gaze point, eye fixation, eye orientation, eye position, and movements of the eye including pupillary movement. This functional activity also includes eyelid movement (e.g. an eyeblink), which provides protection to the eye. Fundamentally, movements include, saccades, which abruptly change the point of fixation, smooth pursuit, which keeps a moving stimulus on the fovea, vergence, which align the fovea of each eye with targets located at different distances from the observer, vestibulo-ocular reflex movements, which maintains eye fixation on a visualized object with head rotation, optokinetic reflex movements, which allows the eyes to follow objects in motion clearly while the head remains stationary, pupil diameter/movement changes, which controls the amount of light which reaches the retina and maximizes visual acuity, vestibulo-ocular reflex cancellation, which triggers eye movements as a result of head motion to maintain fixation on a moving visual object, and eyeblinks, which protects and lubricates the eye. All of these functional activities ultimately are designed to maintain maximal visual acuity with daily activities. Measures of functional activity in this document and embodiments determine eye fixation ability, normal health and can detect an abnormal health status, such as neurologic disorders, biochemical impairments, physiologic impairments including cognitive deficits, fatigue as well as provide health-related biomarkers for early treatment, visual training or rehabilitation for these abnormal conditions.

Gaze or gaze point is defined as where the eyes are looking. More specifically, a gaze point is the instantaneous spatial location of the visual axis landing on the visual stimulus. As such, it has an (x, y) coordinate and a timestamp corresponding to its measurement. If a series of gaze points is very close, in time and/or space, this gaze cluster constitutes a fixation, denoting a period where the eyes are locked towards an object. Gaze can serve as a reliable indicator of attention and cognitive effort. In this document and embodiments, it is also referred to as the point-of-gaze (POG) during a fixation and is an important ocular parameter measurement in this human health system described herein for determining the human health status.

Global Shutter is defined as an imaging sensor that is capable of simultaneously scanning the entire area of an image. This is contrasted with a rolling shutter where the image area is scanned sequentially, typically from the top to bottom. Some consumer and industrial machine vision and 3D sensing need a global shutter to avoid motion blur. Target applications include facial authentication and eye tracking.

Head measurement sensor in this document is defined as a sensing device or apparatus which measures head position, and/or orientation, and/or movement information of the head. The head sensing device can be comprised of one or more accelerometer(s), magnetometer(s), and/or gyroscopes. This sensing device is also referred to as a head odometer in XR (extended reality) devices.

Health-related biomarkers are broadly defined in this document and embodiments as an objective, accurately measurable and reproducible ocular parameter indicator of a person's medical signs. They are characteristics, products, or processes of the body that can be objectively measured and evaluated as an indicator of biological or physiologic processes. In this document and embodiments, biomarkers represent the signs and features of neurologic disorders, biochemical and/or physiologic impairments that can be detected by measured ocular parameters. These biomarkers can serve as early warning systems for health and may be a single characteristic or a panel of multiple characteristics. A biomarker can represent a measured ocular parameter indicator of pharmacologic, physiologic, or biochemical responses to a therapeutic intervention, including training, visual rehabilitation and/or pharmacological therapeutics. Changes in ocular parameter biomarkers can be a useful predictor of pharmaceutical treatment outcomes. An example of a biomarker in Alzheimer's disease can be decreased amplitude and latency of the pupillary light reflex with increased pupillary size. Another example as seen in Parkinson's disease can be reduced saccadic accuracy and increased saccadic latency. Abnormal vergence measurements in combination with abnormal smooth pursuit accuracy can be a biomarker for traumatic brain injury. A biomarker for chronic alcohol use can be prolonged latency with antisaccade tasks. Epilepsy can have reduced saccade latency, pupil dilation and/or vergence abnormalities as an early biomarker. Amyotrophic lateral sclerosis can demonstrate abnormal cogwheeling during smooth pursuit, disturbances with eye fixation and other features with nystagmus such as square wave jerks as biomarkers. Increased eye tracking sampling rates facilitate the specificity of biomarkers for particular disorders and impairments. Those specific disorders and impairments, such as neurologic disorders, biochemical impairments and/or physiologic impairments, can have distinct saccade characteristics of accuracy, amplitude, latency, duration, and velocity, including those with antisaccade and prosaccade tasks. Additionally, these disorders and impairments can have distinct pupillary characteristics of latency, velocity, amplitude, and duration. Vergence biomarkers of convergence and divergence measures including peak velocity, amplitude, symmetry, and latency can also be used to determine specific disorders and impairments.

A hologram is defined as a three-dimensional image reproduced from a pattern of interference produced by a split coherent beam of radiation (such as a laser). It represents an image created by a photographic projection of a recording of a light field and appears as a three-dimensional representation on a two-dimensional object.

Human health status is a multidimensional concept, requiring multiple indicators and multiple methodologies for adequate measurement. It represents an individual's level of wellness and illness, mentally and physically, and in this document and embodiments takes into account the measures to determine the presence of neurologic, biochemical and/or physiological health and function. It can be based on the individual's medical history, physical examination, assessment of laboratory studies, medications, existing disorders, impairments, or disabilities.

The iris is the colored ring portion of the eye. It is comprised of muscles microvessels, pigment cells and connective tissue. The color of the iris and other characteristics are unique to each individual. Five most commonly found iris characteristics are Fuchs' crypts, Wolfflin nodules, pigment spots, contraction furrows and conjunctival melanosis. The muscles of the iris control the pupil diameter and the amount of light entering the eye and the pigment of the iris serves to block out light, allowing it to only enter through the pupil opening. The iris muscle folds like an accordion when the pupil expands. Because of this accordion-like movement when the pupil constricts, the pleated folds can easily be visualized and in the pleats, the micro-blood vessels that nourish the iris are seen as very small white lines. The radius of the iris is 12 mm on average. From anterior (front) to posterior (back), the layers of the iris are: anterior limiting layer, stroma of iris, iris sphincter muscle, iris dilator muscle (myoepithelium), anterior pigment epithelium and posterior pigment epithelium. Part of the posterior epithelium forms the pupillary ruff, a roughly textured ring encircling the pupil. The iris is divided into two major regions: the pupillary zone is the inner region whose edge forms the boundary of the pupil, and the ciliary zone is the rest of the iris that extends to its origin at the ciliary body. The collarette is the thickest region of the iris, separating the pupillary portion from the ciliary portion and where the sphincter muscle and dilator muscle overlap. The rich texture of the iris, including the presence of patterns, edges, or other complex features, unrelated to color are all important components of the image. In addition to light regulation, the human iris responds to emotional stimuli, cognition, sleep, and arousal. The iris characteristics can be imaged by an eye sensor and used to measure ocular parameters to determine the position, movement, orientation, and functional activity of the eye to determine the human health status, such as normal health, neurologic disorders, physiologic and/or biochemical impairments. Because of the uniqueness of the iris with each individual, scanning iris characteristics can act as a controller to open and operate an electronic device or wearable device and establish or determine which ocular parameter testing or training programs are needed, based on the private information stored in a personal health database.

Kinetosis is defined as the state of being dizzy or nauseated because of motions that occur while traveling in or on a moving vehicle. This can occur with ocean travel (e.g., sea sickness), air travel (e.g., air sickness), or automobile travel (car sickness). Kinetosis describes symptoms related to simultaneous vestibular, visual, and somatosensory stimulation. These symptoms include nausea, dizziness, headache, malaise, increased salivation, vomiting, and drowsiness. The sensory conflict theory suggests kinetosis can be attributed to the conflict that occurs between the visual, vestibular apparatus (e.g., labyrinthine portion of the inner ear) and somatosensory systems resulting from real or virtual motion. Afferents from the vestibular apparatus arrive at the vestibular nuclei of the brainstem, which also receives inputs from the visual and proprioceptive systems. Efferent projections then reach the temporoparietal cortex via the posterolateral thalamus, triggering autonomic reactions and the vomiting center. When there is a discrepancy between actual versus expected patterns of vestibular, visual, and kinesthetic inputs, it initiates the cascade of motion sickness symptoms. Motion sickness can be induced in almost all subjects with a functioning vestibular apparatus given a sufficient provocative environment, and results in vestibular nystagmus. Fixation of gaze or closure of eyes generally prevents visual motion sickness, while vestibular otolithic function is eliminated in microgravity of space, indicating a predominant pathogenetic role for visuo-sensory input. The causes of kinetosis symptoms can be related to subjects with central disorders, such a with migraines, or a cerebrovascular accident such as a stroke or basilar artery occlusion. Labyrinthine impairments can also cause kinetosis symptoms of motion sickness as they can increase visual-vestibular conflict.

A Light sensor is defined as a device used to detect light and comprises many different types of light sensors responsive to different and/or multiple wavelengths or types of light sources and may function in different ways. In the spectrum of electromagnetic waves, the ranges of frequencies which can be detected by light sensors are between infrared, near infrared (NIR), short-wave infrared (SWIR) light, to visible light, and up to ultraviolet light. They can detect and convert the light energy in the form of photons to electrical energy in the form of electrons. They may also be known as image sensors, photo sensors, photo-electric devices, photodiodes, photo transistors, photo resistors, and optical detectors. A commonly used light or image sensor is the camera or video camera. The video camera can also be defined as an imaging device that has at least one opto-electric transducer configured for converting a light signal to an electrical signal. A charged coupled device (CCD) transports electrically charged signals and is used as a light sensor in digital cameras and night-vision devices. Photomultipliers detect light and multiply it. Light sensors can be classed into three types based on the physical quantity that is affected. The main classes are photo resistors, photo voltaic and photo emitters. Photo emitters generate electricity when exposed to light. Photo resistors change their electrical properties when illuminated and photo voltaic generate a potential proportional to the intensity of the light. One such photo-electric device is the photojunction diode which uses light to control the flow of electrons across the junctions. A photodiode is in the class of photojunction device which is essentially a PN junction light sensor. They are generally made from semiconductor PN junctions and are sensitive to visible light and infrared light. When light is incident on a photodiode, the electrons and holes are separated and will allow the junction to conduct.

The limbus is the junction of the white opaque sclera and transparent cornea (e.g., corneal border) and is approximately 1.5 mm wide. Characteristics of the limbus also contains vessels, the anterior ciliary arteries, and important features related to eye functions including fibrovascular ridges radially oriented known as palisades of Vogt that host corneal stem cells for epithelial turnover. The limbus is not symmetrical. The distance from the center of the eye to the upper limbus is shorter than for the remaining sectors. The mean range in horizontal meridian amounts to 12.68 mm and in vertical meridian 11.76 mm. Limbus characteristics can be scanned as image features for eye tracking. The limbus characteristics can be imaged by an eye sensor and used to measure ocular parameters to determine the position, movement, orientation, and functional activity of the eye to determine the human health status.

Linear velocity is defined as the speed and direction of a physical object that is moving in a straight line. It is the rate of change of the object's position with respect to time.

Machine Learning is defined as the science of getting computers to learn and act like humans, and improve their learning over time in autonomous fashion, by feeding them data and information in the form of observations and real-world interactions. Machine learning fundamentally is the technologies and algorithms to parse data, automatically learn insights and recognize patterns from data, and applying that learning to make increasingly better decisions. This entails getting computers to act without being explicitly programmed and is based on algorithms that can learn from data without relying on rules-based programming. Deep learning, an advanced method of machine learning, goes a step further. Deep learning models use large neural networks—networks that function like a human brain to logically analyze data, to learn complex patterns and make predictions independent of human input. Examples of machine learning in embodiments herein can include, but not limited to artificial neural networks, association rule learning, Bayesian networks, classifier learning, decision tree learning, deep learning, inductive logic programming, regression models, reinforcement learning, representation learning, rule-based machine learning, similarity and metric learning, and sparse dictionary learning.

Margin to Reflex Distance is defined as the distance from the eyelid margin to the corneal light reflex. It is measured by having an individual fixate on a light and measuring the distance from the margin of the eyelid to the corneal light reflex. There are two margin-to-reflex distances (MRD), corresponding to the measurement from the upper and lower eyelids. MRD1 is the upper eyelid margin-to-light reflex and is the single most important measurement when evaluating ptosis. MRD2 is the lower eyelid margin-to-light reflex. MRD1+MRD2 provides the palpebral fissure height.

Near accommodative triad is a three-component reflex that assist in the redirection of gaze from a distant to a nearby object. It consists of a pupillary accommodation reflex, lens accommodation reflex, and convergence reflex.

Neurobehavioral disorder is also a neurologic disorder and defined as a behavioral impairment seen in association with brain disease (e.g., stroke, multiple sclerosis, dementia, and neuro-oncological conditions), transient as well as permanent brain impairments (e.g., metabolic and toxic encephalopathies), and/or injury (e.g., trauma, hypoxia, and/or ischemia.

A neurocognitive disorder (NCD) is a neurologic disorder defined as a disorder characterized by a decline primarily in mental function due to a medical disease of the brain caused by a variety of acquired disorders and/or impairments such as cerebrovascular disease, Alzheimer's disease, infections, drug effects, abnormal metabolic and hormonal deficits, and trauma, such as with concussions. It is an acquired condition representing a neurologic disorder and underlying brain pathology that results in a decline in cognitive abilities such as memory, problem solving, executive function, intellect, and perception.

A neurodegenerative disorder is a type of neurologic disorder and is defined by progressive loss of a select vulnerable populations of neurons, which contrasts with select static neuronal loss because of metabolic or toxic disorders. Neurodegenerative diseases can be classified according to primary clinical features (e.g., dementia, parkinsonism, or motor neuron disease), anatomic distribution of neurodegeneration (e.g., frontotemporal degenerations, extrapyramidal disorders, or spinocerebellar degenerations), or principal molecular abnormality. The most common neurodegenerative disorders are amyloidoses, tauopathies, α-synucleinopathies, and TDP-43 proteinopathies. Specific examples of neurodegenerative diseases are Alzheimer's disease, Parkinson's disease, Huntington's disease, amyotrophic lateral sclerosis, frontotemporal dementia and the spinocerebellar ataxias. These diseases are diverse in their pathophysiology, with some causing memory and cognitive impairments and others affecting a person's ability to move, speak and breathe.

A neurologic disorder is defined in this document and embodiments as a disorder or condition that affects the brain, the spinal cord and/or nerves found throughout the human body, resulting in physical dysfunction. Structural, biochemical, physiologic, or electrical abnormalities in the brain, spinal cord or other nerves can result in a large range of symptoms. There are numerous different types of neurological disorders which include, but are not limited to cerebrovascular/stroke impairments, neurodegenerative disorders, neurocognitive disorders, neurobehavioral disorders, demyelinating diseases, brain lesions including tumors, as well as neuro-oncology disorders, and each can affect different areas of the central nervous system. Measures of ocular parameters, such as smooth pursuit, saccades, pupillometry, VOR, VORC, vergence, eye fixation, or nystagmus can be used to detect health-related biomarkers for these different neurologic disorders, based on the neural tract and pathway involvement associated with the disorder.

Nystagmus is defined a general term defined by two oscillatory involuntary eye movements, with a "slow phase" eye movement followed by a second movement (e.g., fast phase or a re-fixation phase or saccade) to stabilize images on the retina. This eye movement can be horizontal, vertical, torsional or a combination. Nystagmus can occur as a result of several factors including: a) vestibular stimulation (e.g., vestibular nystagmus); b) visual stimulation (e.g., optokinetic nystagmus); or c) it can occur without any vestibular or visual stimulation (e.g., spontaneous nystagmus). Vestibular nystagmus can be induced by head and/or body movement and due to stimulation of the vestibular apparatus in the inner ear. Optokinetic nystagmus (OKN) is induced by a visual stimulus moving across the visual field. OKN is also referred to as the optokinetic reflex (OKR). The term "optokinetic nystagmus" is synonymous with "visual nystagmus". Spontaneous nystagmus can occur as a result of an acute labyrinthine impairment, stroke or other lesion in the brainstem or cerebellum. When present, nystagmus can be characterized by eyes that drift slowly in one direction and then jerk back in the opposite direction, called "jerk nystagmus". Alternatively, nystagmus can be referred to as a "pendular nystagmus", characterized by eye motion moving like a pendulum swinging back and forth. Although nystagmus is often described by the direction of its quick phases (for example, downbeat nystagmus), it is the slow phase that reflects the underlying disorder. Generally, vestibular nystagmus, optokinetic nystagmus and spontaneous nystagmus can all be associated with labyrinthine impairments or central nervous system disorders. However, specific features of the nystagmus can help to differentiate central disorders from labyrinthine impairments. For example, spontaneous vertical or pure torsional nystagmus can indicate a central lesion. Central lesions typically have a direction changing, gaze-evoked nystagmus (i.e., left-beating nystagmus on left gaze, and right-beating nystagmus on right gaze) and frequently have decreased fixation suppression. However, suppression of nystagmus with fixation is more typical of labyrinthine impairments. Additionally, the type of nystagmus (e.g., jerk, pendular, etc.) can provide a clue to the origin of the nystagmus. For example, pendular nystagmus can result from a brain disorder, such as with multiple sclerosis, and jerk nystagmus is more often related to a labyrinthine impairment. During nystagmus, vision is reduced or limited. Nystagmus can have variable amplitude and frequency, and can be worsened or improved by gaze position, fixation, vergence, or covering one eye (latent), depending on the cause. The nystagmus intensity is defined as the slow-phase velocity (SPV). Measurements include this SPV and duration as well as binocularity, frequency, and amplitude. Nystagmus can be a valuable ocular parameter to determine human health and help to differentiate disorders, such as stroke or brain lesions from physiologic impairments, including spatial disorientation, and motion sickness.

Ocular Parameters are defined as measurable factors that define and determine the components, actions, processes, behavior and functional ability of the eye, eyeball, and eyelid. Included in ocular parameters are eye position, eye and eyelid movement responses which can be detected or measured, including saccades, vestibulo-ocular reflex, vestibulo-ocular reflex cancellation, vergence, smooth pursuit, nystagmus, dynamic visual acuity, pupil size, eyeblinks and the focused eye position (e.g., eye fixation or gaze point). Reflexes included in the measured ocular parameters or eye movement responses include the pupillary light reflex, pupillary dark reflex, near accommodative triad, corneal reflex, palpebral oculogyric reflex (Bell's reflex) and the optokinetic reflex (OKR). The purpose of having eye movements is to maintain constant foveation of an object of interest or to foveate a target quickly. Measuring movements of eye includes the extraocular muscles (which move/rotate the eye), the ciliary muscles (which helps to focus by changing the lens shape), the levator (which raises the eyelid), and the pupillary muscle (which dilates or constricts the pupil). Measures of ocular parameters can also be referred to as oculometrics, and when used with the discussed platforms discussed herein, such as XR (extended reality) technology, the use of precise health-related biomarkers can be identified to diagnose, quantify, monitor, rehabilitate the progression of neurologic disorders, using artificial intelligence and machine learning to transform clinical diagnostics.

Ocular reflexes are involuntary responses that are usually associated with protective or regulatory functions They require a receptor, afferent neuron, efferent neuron, and effector to achieve a desired effect. Examples of an ocular reflex include those mentioned above including the vestibular-ocular reflex, pupillary reflex, and corneal reflex.

Oculomotor system is defined as the part of the central nervous system (CNS) centers, complex CNS connections or pathways, numerous peripheral inputs, cranial nerves III, IV and VI and the extraocular muscles, which functions mainly in maintaining visual stability, aligning, and controlling eye movements. It is made up of many brain areas that cooperate to stabilize images of interest on the high-acuity part of the retina. Assessment of deficits in oculomotor function is useful to detect visuomotor impairments due to a closed head injury and other neurologic disorders as well as biochemical and physiologic impairments.

An opto-electric transducer is defined as a device that converts an optical signal into an electrical signal. Examples of such a device include photodetectors, photosensors, charge conducting devices (CCDs), complementary metal-oxide semi-conductor devices (CMOS), micro-opto-electromechanical-systems (MOEMS), microelectromechanical system (MEMS), and photodiodes.

Palpebral Fissure is defined by the normal exposed area between upper and lower eyelids. The palpebral fissure vertical height (PFH) is measured between the margin of the lower eyelid to the margin of the upper eyelid. The normal palpebral fissure height is 8-11 mm. This is a key measurement that is needed when assessing ptosis.

Palpebral oculogyric reflex (Bell's reflex): The palpebral oculogyric reflex, or Bell's reflex, refers to an upward and lateral deviation of the eyes during eyelid closure against resistance, and it is particularly prominent in patients with lower motor neuron facial paralysis and lagophthalmos (i.e., incomplete eyelid closure).

Performance enhancement in this document and embodiments is defined as activities to improve a subject's capability to do a task and/or improve health. Performance enhancement can comprise visual rehabilitation and/or visual training. Performance enhancement can be applied to ocular parameters discussed herein, to achieve normal health or supranormal ability.

A photodetector is defined as a device that turns light into an electrical signal. This can be an opto-electric transducer which converts the optical signal into an electrical signal. Multi-element photodetectors can be used for imaging. A non-imaging photodetector is a device that turns light into an electrical signal but has too few elements to produce an image. Thus, a non-imaging photodetector might comprise only one light-sensing element that turns received light into a magnitude based on the intensity of the light received. A non-imaging photodetector might comprise two light-sensing elements that allow the detection of an edge, but not an image, and therefore can be called an edge-detection photodetector. A non-imaging photodetector might comprise a two-dimensional pattern of three or four photodetectors, that allow the detection of an edge in more than one dimension, but not an image. Photodetectors could work with visible light, they could work with invisible light (such as infrared or ultraviolet), or they could work with a combination of visible and invisible light.

Physiologic health impairment is defined as impairment of the normal biological functions of organs, tissues, or cells of humans. It also includes impairments affecting the vital functions, growth and development, the absorption and processing of nutrients, the synthesis and distribution of proteins and other organic molecules, and the functioning of different tissues, organs, and other anatomic structures, such as the pulmonary, cardiac, and neurologic systems. Examples of physiologic health impairments includes, but not limited to, fatigue, post-traumatic stress disorder, motion sickness, dizziness, eye movement disorders, retinopathy, and visual disorders.

The pupil is the black aperture located in the center of the iris of the eye that allows light to strike the retina. In optical terms, the anatomical pupil is the eye's aperture. The pupil appears black because light rays entering the pupil are either absorbed by the tissues inside the eye directly, or absorbed after diffuse reflections within the eye. Pupil size is a typical characteristic of the pupil that can be measured. In this document pupil size can also be the same as pupil diameter. The diameter of the pupil can be modulated by light, cognition, sleep, drugs and arousal Dilation of the pupil is known as mydriasis and contraction as miosis. The size of the pupil, measured as diameter, can be a symptom of an underlying disease. For example, pupils can become mydriatic, or dilate, in response to potential disease, drug toxicity, trauma, increased intracranial pressure, brainstem damage, or nerve damage to cranial nerve II and/or III. Additionally, chromatic pupillometry can be valuable due to its capacity to preferentially separate outer retinal (rod and cone-mediated) and inner retinal (melanopsin) responses in a single, objective, non-invasive pupil measurement. Pupil center corneal reflection (PCCR) can be used as a method for eye tracking, in which the pupil and corneal reflections are measured. Using such measurements, the eye position, point of gaze, orientation, and eye movements can be determined with advanced mathematical analysis.

Pupil performance refers to the response of the pupil to a given stimulus, activity and/or human health status. Pupil performance can be determined by measurements such as changes in pupil size, changes in pupil dilation, pupil response latency, and pupil response duration. Pupil performance measurement can be used to diagnose a neurologic condition. Pupillometry outcomes provide clinical health-related biomarkers of many ophthalmic and systemic diseases.

Pupillary light reflex refers to an autonomic reflex that constricts the pupil in response to light, thereby adjusting the amount of light that reaches the retina Pupillary constriction occurs via innervation of the iris sphincter muscle, which is controlled by the parasympathetic system.

Pupillary dark reflex is defined as the reflex that dilates the pupil in response to dark. It can also occur due to a generalized sympathetic response to physical stimuli and can be enhanced by psychosensory stimuli, such as by a sudden noise or by pinching the back of the neck, or a passive return of the pupil to its relaxed state.

Pupillometry is defined as the measures of pupil size, the (e.g., diameter of the pupil), which includes pupil movement features as a function of time, to determine pupil performance. Pupil size is affected by the level of retinal illumination, the accommodation state of the eye, various sensory and emotional conditions, cognitive and affective information processing as well as neurologic disorders, such TBI, biochemical impairments, such as with drug use and physiologic impairments, such as with alertness. Pupil measures includes movement features of pupil diameter, dilation information including acceleration, latency, duration of changes in size, amplitude changes, and constriction information including latency, duration as well as amplitude changes. It also includes peak and average constriction velocity from the iris sphincter muscle as well as dilation velocities of the dilator pupillae muscle under numerous stimulus conditions, including dim pulse, dim step, bright pulse, bright step, bright red step, and bright blue step. A higher frame rate is desirable to determine time parameters with a higher precision and examine the time dependence of the phase between the pupil and other bio-signals. A higher spatial or linear resolution also can provide information of micro-fluctuations in pupil size. The pupil performance or pupillometry, which results from measures of pupil size and other pupil features described in this document and embodiments, can be an important health-related biomarker for neurologic disorders, biochemical and physiologic impairments.

The retina is the innermost layer of the eyeball that extends from the site of exit of the optic nerve to the posterior margin of the ciliary body and is characteristically comprised of blood vessels, optic nerve, optic disc, macula, the inner neurosensory retina, and the outer retinal pigmented epithelium. The retina is where the image of the viewed environment is converted to the neural impulses that are transmitted to the brain via the optic nerve for interpretation and analysis. The *Macula lutea* is an area at the center of the posterior retinal laver and is a site of the clearest vision, as it contains the highest amount of the photoreceptor cells. The optic disc is located 3 millimeters medially to the *Macula lutea*, and it is a site where the optic nerve leaves the eye. The retinal blood vessels are comprised of branches of the central retinal artery and capillaries from the choroid. These retina characteristics can also be scanned to detect health-related biomarkers of neurologic disorders, including those associated with cognitive impairment.

Saccades are defined as rapid, ballistic movements of the eyes that abruptly change the point of fixation when gazing from one object to another. The eye movements between fixations are generally referred to as saccades. Like fixations, saccades are made up of multiple gaze points and they have a start and end point each with a timestamp. Measures can be made at which point saccades occurred in time and their duration. Whereas VOR, OKN, and pursuit movements all have the function of stabilizing the world, or a particular object image, the saccadic system serves to change our gaze from one point to another. The purpose of saccades is to alter the gaze from one object of interest to another under effort of will (voluntary saccades), to alter the gaze to a sudden event in the periphery (reflex saccades), to reset gaze after VOR or OKN has carried it to an extreme (fast phases of nystagmus), to correct small errors of fixation (fixational microsaccades), and to correct small errors in pursuit (catch-up or back-up saccades). Individuals with an impaired VOR are not able to keep their eyes fixed on a stationary target and have to produce fast eye movements to reposition the eyes on the target, referred to as catch-up saccades. Vision is disrupted during saccades, a phenomenon called saccadic omission. Saccadic omission occurs because of visual masking in which the image seen before the saccade tends to mask the image seen during the saccade. Retinal blur occurs as the images move rapidly across the retina because the retina has limited temporal resolution. Saccade parameters of measurement includes accuracy, amplitude, inhibition, latency, duration, velocity with initial acceleration and peak velocity, frequency, and number over time. These quantitative measurements of saccades are used to assess the function of the oculomotor system, to investigate the effects of drugs or lesions, and to aid diagnosis of neurologic disease or locating brain lesions in the central nervous system.

Saccade accuracy refers to the eye's ability to quickly move and accurately shift from one target fixation to another. Accuracy refers to how well the calculated fixation location matches actual fixation location. This is expressed in degrees of visual angle (a half circle has 180° of visual angle). Saccade adaptation is a process for maintaining saccade accuracy based on evaluating the accuracy of past saccades and appropriately correcting the motor commands for subsequent saccades. An adaptive process is required to maintain saccade accuracy because saccades have too short a duration relative to the long delays in the visual pathways to be corrected while in flight.

Saccade amplitude refers to the size of the eye movement response, usually measured in degrees or minutes of arc. The amplitude determines the saccade accuracy. This is sometimes referred to as gain. It is also described as the angular distance the eye travels during the movement.

Saccade Inhibition refers to an absence or near-absence of saccades initiated around 80-120 msec following a brief visual distracting effect that interferes with the production of scanning saccades.

Saccade latency refers to the time taken from the appearance of a visual target to the beginning of an eye movement in response to that target. Normal saccades have a latency of typically about 200 msec. This is significantly longer than OKN, smooth pursuit or vergence, and more than ten times longer than VOR. Many factors influence saccade latency. Longer latencies occur with weak (dim or low contrast) targets, unpredictable targets, and with older subjects. Shorter latencies occur with brighter visual targets, predictable targets, with auditory stimuli, and with younger individuals.

Saccadometry is defined as the functional evaluation of saccadic eye movements with the neural pathways and frontal, parietal and occipital areas of brain involvement. Saccadometric measures can include accuracy, latency, duration, frequency, and velocity of a saccade or multiple saccades in combination with the position or movement of each eye. The two most common tests are the prosaccade and antisaccade. A prosaccade requires an eye-movement toward target jumps. Specifically, individuals are instructed to look at a center target and then need to direct their gaze toward a target dot appearing at the periphery as quickly and as accurately as possible. After viewing the peripheral target, they then return to the center target dot and wait for the next target jump. By contrast, antisaccade tasks typically require an eye-movement of equivalent amplitude to be executed rapidly, but in the opposite direction. To achieve this, the natural tendency to move the eyes towards the new stimulus has to be overcome in order to direct a voluntary saccade in the opposite direction. The technology discussed herein and in embodiments can utilize saccadometry as a health-related biomarker to enhance the diagnosis and monitoring of neurological disorders, such as traumatic brain disorders.

Saccade velocity is defined as the speed measurement during the eye movement. High peak velocities and the main sequence relationship can also be used to distinguish microsaccades from other eye movements such as ocular tremor, ocular drift and smooth pursuit. Saccades have a very high velocity, up to 800 or even 1000 degrees per second for very large saccades. Saccade velocities follow a very specific, predictable pattern such that the peak velocity of the saccade is dependent on its amplitude. Saccades are reprogrammed after each fixation period. In most cases, if a target moves during a saccade, the saccade in progress is not modified and the next saccade will not occur until one latency period after the end of the first saccade. Therefore, saccades have been called ballistic, meaning that they are determined before they are started and cannot be redirected during movement. Inaccurate control of saccades is termed saccade dysmetria, undershoots are referred to as hypometric and overshoots are termed hypermetric. Peaks corresponding to saccadic movements show a linear relationship between the peak velocity of a particular saccade and the amplitude. Once the peak velocity has been reached, the amplitude of the saccade, and therefore the final position of the eye after the saccade can be determined with a high degree of accuracy. Saccades have fixed relationships between the amplitude, duration, and peak velocity. There are main sequence parameters and relationships. Generally, in normal individuals there is a linear relationship between saccade amplitude and duration.

Sampling rate of eye tracking refers to how many times per second eye position is measured. Common sampling rates are 1,000 Hz, 500 Hz, 250 Hz, 120 Hz, 90 Hz and 60 Hz. During normal adult reading, fixation durations typically vary from about 100-800 milliseconds, with the average being approximately 250 milliseconds. Higher sampling rates produce better temporal accuracy when measuring the duration of fixations and saccades. Specifically, the average temporal error will be approximately half the duration of the time between samples. For example, a sampling rate of 1,000 Hz (sampling eye position every 1 millisecond) will lead to an average error of 0.5 millisecond and a sampling rate of 60 Hz (sampling eye position every 16.7 milliseconds) will lead to an average error of approximately 8 milliseconds.

The sclera is the white portion of the eyeball and its related blood vessels. Characteristically the sclera is comprised of the episclera, an outermost connective tissue layer which is connected superficially to the Tenon's capsule, and its deep surface which overlies the scleral stroma. The anterior part of the episclera also contains a plexus of blood vessels formed by the branches of the anterior ciliary arteries. This plexus is normally not visible, however during inflammation it becomes congested, giving the characteristic appearance of the 'red eyes' in the affected person. It is the scleral stroma, composed of dense irregular connective tissue, which gives the sclera its distinctive white color. The change of scleral color can indicate a pathological process in the body: for example, a yellow sclera may indicate liver diseases such as hepatitis. *Lamina fusca* is the innermost layer of the sclera and receives its name from the large number of melanocytes. Reflections from light sources on the sclera can be used for eye tracking. A glint can be identified as a reflection of light from a sclera characteristic. Glint can be used to measure eye movement, orientation and position of the eye.

Sensor fusion is defined as any stage in an information integration process in which there is a combination (i.e., fusion) of different sources of sensory information into a single sensory signal. In one form, sensor fusion can be an algorithm that combines sensory data or data derived from disparate sources such that the resulting information has less uncertainty than would be possible when these sources were used individually.

Sensor integration refers to the synergistic use of the information provided by multiple sensory devices to assist in the accomplishment of a task by a system. The sensors used for sensor fusion and/or sensor integration can be of the same type (such as opto-electric transducers for a stereoscopic image) or of differing types (such as combining accelerometer and gyroscopic data in a Kalman Filter).

Situational awareness (SA) is defined as being aware of one's surroundings, comprehending the present situation, and being able to predict outcomes. It is a key human skill that can be associated with reducing errors of human performance activities.

Slippage is defined as when an imaging device viewing a subject's eye moves out of phase with the subject's head. The slippage offset is an algorithm that can account for slippage and computes an appropriate value that can be used to synchronize sensor data.

Smooth pursuit is defined as the voluntary movement of the eyes in response to tracking a moving visual object. Such movements are under voluntary control in the sense that the observer can choose whether to track a moving stimulus. These movements are described to be smooth, continuous, conjugate eye movements with velocity and trajectory, determined by the moving visual target. However, the eyes are in continual small-scale motion, showing irregular drift and tremor, interspersed by miniature saccadic movements (less than 0.5 degrees). With the naked eye, smooth pursuit movement appears smooth, but with high-speed eye imaging devices, the movements are not entirely smooth at all, but can have an altered appearance due to the presence of saccades (covert or overt) or saccadic intrusions which can be associated with underlying neurologic disorders or other physiologic or biochemical impairments. There are separate mechanisms of control for horizontal and vertical smooth pursuit tracking. Smooth pursuit eye movement can be divided into two stages: open-loop pursuit and closed-loop pursuit. Open-loop pursuit is the visual system's first response to a moving object we want to track and typically lasts approximately 100 msec. Therefore, this stage is ballistic and visual signals have not yet had time to correct the ongoing pursuit velocity or direction. The second stage of pursuit, closed-loop pursuit, lasts until the pursuit movement has ceased. This stage is characterized by the online correction of pursuit velocity to compensate for retinal slip. In the closed-loop phase, the eye angular velocity and target angular velocity are nearly equal. Pursuit eye movements are initiated within 90-150 msec, while typical latencies for voluntary saccades are in the order of 200-250 msec. The first 100 msec of pursuit is open-loop, and during this period no visual feedback is available because of the delays in the visual system. Thereafter, visual feedback is available to close the loop, and other sources of information are also available to improve performance. These movements are slower tracking movements of the eyes, designed to keep the moving viewed stimulus on the fovea. Measures of initiation parameters can detect information about the visual motion processing required for pursuit. When a bright light appears in the periphery, the fastest it can achieve a smooth pursuit is 30°/second. It first fixes the gaze to the peripheral light and, if not more than 30°/second, will follow the target equally with the movement. Smooth pursuit is an important ocular parameter measurement, and in this document and embodiments, it can be adversely affected by numerous factors including, but not limited to, alcohol, drugs, traumatic brain injury, mental deficits, learning deficits, human performance impairment, neurologic disorders, visual defects, fatigue, alertness, electromagnetic wave energy effects, motion sickness, eye fixation ability, and visual attention. Measurements of this smooth pursuit parameter while following a moving visual target includes acceleration, accuracy, latency, and velocity.

Smooth pursuit acceleration refers to the rate of change of the eye velocity. The first approximately 20 milliseconds of pursuit tend to be the same regardless of target parameters. However, for the next 80 milliseconds or so, target speed and position have a large effect on acceleration.

Smooth pursuit accuracy is defined by the ability of the eyes to closely follow a moving object. The pursuit of visual targets moving with velocities of greater than 30°/s tends to require catch-up saccades. Smooth pursuit accuracy represents how closely the percentage of time the smooth pursuit velocity value remains within the target velocity value.

Smooth pursuit latency is defined by the time from target appearance to the beginning of pursuit. It is measured from traces of eye velocity. It is often calculated by finding the intersection between two regression functions, one fitted to velocity about the time of target appearance, and the second fitted over the initial part of the pursuit response.

Smooth pursuit velocity refers to the speed of the eye movement (velocity) which usually rises to a peak, following pursuit initiation, and then either declines slightly or oscillates around the target velocity. This peak velocity can be used to derive a value for gain (peak velocity/target velocity). It is usually near the velocity of the target. Instead of using peak velocity, measures of velocity at times relative to either target appearance or pursuit initiation can be made. For example, eye velocity up to 100 milliseconds after target appearance can be used as a measure of prediction or anticipation.

Vergence is defined as the simultaneous movement or orientation of both eyes to rapidly obtain or maintain single binocular vision or ocular fusion of the object of interest. To maintain binocular vision, the eyes must rotate around a vertical axis so that the projection of the image is in the center of the retina in both eyes. Vergence measurements can easily be performed. Normally, changing the focus of the eyes to look at an object at a different distance will automatically cause vergence and accommodation, known as an accommodation-convergence reflex. Convergence is the simultaneous inward movement or orientation of both eyes toward each other, usually to maintain single binocular vision when viewing an object more closely. Divergence is the simultaneous outward movement or orientation of both eyes away from each other, usually to maintain single binocular vision when viewing an object which is further away. Typically, vergence velocity responses do not exceed 60 degrees/second. Vergence orientation movements tend to have relatively long latencies, typically on the order of 150-200 msec. Measurements of vergence can be performed while visually following the target element of interest, which moves in a smooth transition to different depths (e.g., dynamic vergence) or in a sequence of steps with the head stationary or head in motion. Such measurements can also include a binocular precision index (BPI) and binocular accuracy index (BAI) to quantify changes of convergence and divergence peak velocity, amplitude, symmetry, and latency. Like other ocular parameters, vergence is an important measure and can be adversely affected by neurologic disorders, biochemical and physiologic impairments.

Version refers to simultaneous movement of both eyes in the same direction: a prefix indicates the direction of the conjugate movement. The muscles in each eye that are the prime movers undergo graded contractions in accord with Hering's Law of innervation, and for each contracting muscle, there is normally a corresponding relaxation of an antagonist (Sherrington's Law). Hering's Law states that the gaze effort command to each eye is the same, if only one eye can see the target, the other eye will receive the same command.

Vestibular apparatus in this document refers to the inner ear balance organs, (also referred to as the vestibular portion of the labyrinth, vestibular portion of the inner ear, labyrinthine portion of the inner ear, and peripheral vestibular system). The vestibular apparatus is comprised of the semicircular canals with sensory elements call crista, which respond to angular acceleration and changes in angular velocity. Additionally, it is comprised of two linear acceleration sensory elements called the maculae, one responsive to movement in the horizontal plane (the utricle) and one responsive to movement in the vertical plane (the saccule). In this document, labyrinthine impairments also refer to impairments of the vestibular apparatus as defined above. The vestibular system refers collectively to the vestibular apparatus of the inner ear, the brain structures, and neural pathways that help control balance and eye movements.

Vestibulo-ocular reflex (VOR), is defined as a gaze reflex or reflexive movement of the eye, which enables an individual to maintain visual fixation on a stationary target while the head is in motion. This reflex keeps the visual image stable on the retina, by producing an eye movement in the direction opposite to the head movement, thus preserving the visual image in the center of the visual field. While viewing a stationary visual target, this reflex is initiated by rotational head movement in one direction, and information from the inner ear organs (e.g., vestibular portion of labyrinth) generates the eye response of movement in the opposite direction. Healthy individuals are able to keep their point of gaze on the target during a head rotation activity due to the VOR. It is a short latency reflex system, which generates a rotation of the eye with an amplitude equal and opposite to the direction of a head movement because of vestibular stimulation, namely the semicircular canals, utricle, and saccule. In this document vestibulo-ocular reflex is synonymous with vestibular ocular reflex. The VOR is valuable in determining the human health status including neurologic disorders, biochemical health impairments, physiologic health impairments, and/or normal health. Measurements of the VOR include accuracy, gain (amplitude ratio of eye to head movement, ratio of eye to head angular velocity, or peak slow phase eye velocity/peak head velocity), phase (the timing response between the head movement and the reflexive eye response), symmetry (slow component of eye response when head is rotated to one side compared to rotation to the other side), and saccades (overt and covert). Gain of the VOR is also defined as the change in the eye angle divided by the change in the head angle during the head rotation. Gain or velocity gain can be measured over a time range/period or at specific time points after the initiation of head movement, such as 40 ms, 60 ms. Another possibility to evaluate gain is a linear regression of eye and head velocity (e.g., regression gain), which compares the slopes between head and eye velocity around peak head acceleration (ratio of velocity slopes using regression around peak acceleration). Still another method is calculating gain as the ratio of the areas under the curve (AUC) after removing saccades from eye and head velocity curves (referred to as position gain), which compares eye and head position (ratio of area under the curves after removal of saccades from the whole slow phase VOR trace). In this document and embodiments, VOR measurements can including any of the above methods of calculation for analysis. The VOR can be a valuable measure for detecting a neurologic disorder, such as traumatic brain injury, or biochemical and/or physiologic impairment.

Vestibulo-ocular Reflex Cancellation (VORC) is defined as an ocular parameter measurement used to assess visual motion sensitivity and suppresses the VOR during combined eye and head tracking. It is initiated by a moving visual target, and the head moves in the same direction to follow the visual target. Measurements of the eye movement are correlated with the head orientation information. It is also referred to as vestibulo-ocular reflex suppression (VORS) in this document. Specifically, an individual is asked to rotate the head and eyes together while following a moving target, or visual element of interest, while the target moves side to side, up and down, and/or in diagonals. The VORC compensates for head movement to permit the eyes to maintain foveal fixation on moving objects in the environment. Moving objects in the environment are often tracked with head movement during which the eyes are held stable relative to the head. Under these conditions, the VOR must be suppressed to prevent loss of visual fixation on the target. Healthy individuals with VOR suppression/cancellation with impulse rotation of the head produce saccades since the VOR drives the eyes in the opposite direction of the head impulse, while the target is moving synchronously with the head. Individuals with an absent VOR do not have to produce saccades during VOR suppression/cancellation with impulse head rotation, since their eyes are already moving along with the head during the head impulse, keeping them on the target. Vestibulo-ocular reflex cancellation is an important ocular parameter measurement used to detect neurologic disorders, such as TBI and other physiologic health impairments.

Virtual reality (VR) is defined as near-reality and describes an artificial three-dimensional, computer-generated environment which can be explored and interacted with a person. Individuals using virtual reality become part of the virtual world or are immersed within the environment and while there, can manipulate objects or perform a series of actions in that 3-D space.

Visual-Oculomotor-Vestibular (VOV) Rehabilitation refers to rehabilitation training therapy designed to improve the health status of individuals with neurologic disorders or other impairments which affect the vision, oculomotor and/or peripheral vestibular system (e.g., inner ear or labyrinthine impairments). Affected individuals have deficits affecting the ocular parameters due the involvement of the central nervous system and/or vestibular neural pathways. In this document and claims, visual-oculomotor-vestibular rehabilitation is a system for improving human health using a display with visual training information and will be used synonymously with visual rehabilitation. Habituation therapy, gaze stabilization, and balance exercises using a visual display are three examples of types of visual-oculomotor-vestibular rehabilitation training. In this document and embodiments, rehabilitation is the same as visual rehabilitation or visual-oculomotor-vestibular (VOV) rehabilitation and refers rehabilitation using a display or viewed image.

A waveguide is defined as a device that directs the light wave's transference so that the light wave transmits only in a certain direction. With this device, there is minimal loss of light by restricting the transmission of the light wave to one direction.

Figures Describing Ocular Parameter-Based Human Health Determination

Referring now to the figures, FIG. 1 shows a generalized method for observing eye and head information to measure ocular parameters, determine human health status, and train for performance enhancement or use for rehabilitation. The method starts by establishing a wearable device 602. Next, an eye imaging device (e.g., module) 608 is established on the wearable device. Optionally, a head-orientation sensor can be established on the wearable device, as shown at 606. Also optionally, a display can be established, as shown at 618. This display, if established, could be either on the wearable device or external. If a display is established (step 618), this display can be used to provide visual motion, physical movement, or another stimulus as appropriate for what is being assessed, as shown at step 690, and this process shown at 690 can be varied and repeated as needed.

The wearable device 602 can provide a visual stimulus from the stimulus produced at step 690: eye responses that can be measured by the eye imaging module 608: and head movement responses that can be measured by the head orientation sensor 606. The eye imaging module 608 can image an eye characteristic, as shown at 692, allowing eye response information to be measured and recorded, as shown at step 642. The eye characteristic being measured can comprise a characteristic of the retina, sclera, cornea, limbus, or pupil. The eye information can comprise eye position information, horizontal eye movement information, vertical eye movement information, pupil size information, and eyelid information (and more specifically eyeblink information). Head movement responses can be measured and recorded as shown at step 640. This head movement response can comprise head orientation change information such as pitch and yaw of a person's head, where pitch represents rotation about a first axis representing up and down movement of the person's face when the rear of the person's head moves in the opposite direction, and yaw represents horizontal movement of the person's face when looked at from the person's front about a second axis wherein the second axis is vertical, substantially aligned with the person's spine, and perpendicular to the first axis.

The eye information from step 642 and the optional head information from step 640 can be used to measure ocular parameters, as shown at step 694. Examples of ocular parameters that embodiments of the invention can be configured to measure can include saccades, vestibulo-ocular reflex, vestibulo-ocular reflex cancellation, vergence, smooth pursuit, nystagmus, dynamic visual acuity, eye fixation or gaze point and/or eyeblinks.

Further referring to FIG. 1, the ocular parameters measured in step 694 can be compared to baseline values (i.e., normal values), as shown at step 800, to detect abnormal ocular parameters 840. These abnormal ocular parameters 840 can be combined with physical exam information 812 and health history (which includes prior laboratory, imaging and signs) 810 to detect health-related biomarkers as shown at 860. This health status differences can then optionally be categorized as shown at step 697. Among the health categories this health status and detected health-related biomarkers can be categorized into can include:
 a) Normal health status, shown at 802;
 b) Neurologic disorders, shown at 804;
 c) Biochemical health impairments, shown at 806; and
 d) Physiologic health impairments, a shown at 808.

The comparisons made with 802, 804, 806, and 808 can then be used to generate a categorized human health status, as shown at 698. The determination of human health status from 698 can then be used to train, treat, and/or rehabilitate as possible and/or necessary, as shown at 820. This training, treatment, and/or rehabilitation will be further described with reference to FIG. 32. Some of the abnormal ocular parameter measures can be associated with physiologic impairments, such as fatigue, inattentiveness, and cognitive decay. A cognitive rehabilitative program can be used with specific identified cognitive conditions.

When assessing cognitive deficits for human health disorders or impairments, numerous visual tasks can be performed with visual targets on a display. For example, ocular parameter measurements, including smooth pursuit, vestibulo-ocular reflex cancellation, pupillometry, eyeblink information, and dynamic visual acuity, use visual targets for testing and all provide information about cognition and inattentiveness. There are other visual cognitive function tests which can be viewed on a display and detect cognitive deficits. These tasks can be used as visual cognitive function tests, that will be further described with reference to FIG. 35.

Embodiments of the inventions described herein can also provide supernormal enhancement of the ocular parameters discussed, where no balance disorder exists, for enhancement of athletic and vocational abilities. Embodiments can enable individuals to reach a higher level of performance in their occupation, enable them to have increased ocular performance functions when participating in their usual occupational or play activities as well as enabling cognitive training and rehabilitation.

Regarding 810 (health history), diagnosis of health status has been described as both a process and a classification scheme, or a pre-existing set of categories agreed upon by the medical profession to designate a specific condition. The working diagnosis may be either a list of potential diagnoses (a differential diagnosis) or a single potential diagnosis. Generally, there are four types of information-gathering activities in the diagnostic process: 1) taking a clinical history and interview, 2) performing a physical exam; 3) obtaining diagnostic testing; and (4) sending a patient for referrals or consultations. A subject's clinical history includes documentation of the current concern, past medical history, family history, social history, symptom history, and other relevant information, such as current medications (prescription and over the counter) and dietary supplements. An accurate history facilitates a more productive and efficient physical exam and the appropriate utilization of diagnostic testing. The medical history of a patient is the most useful and important element in making an accurate diagnosis, much more valuable than either physical examinations or diagnostic tests. The medical interview is the process of gathering data that will lead to an understanding of the disease and the underlying physiological process. A common maxim in medicine attributed to William Osler is: "Just listen to your patient, he is telling you the diagnosis."

Figure 8:
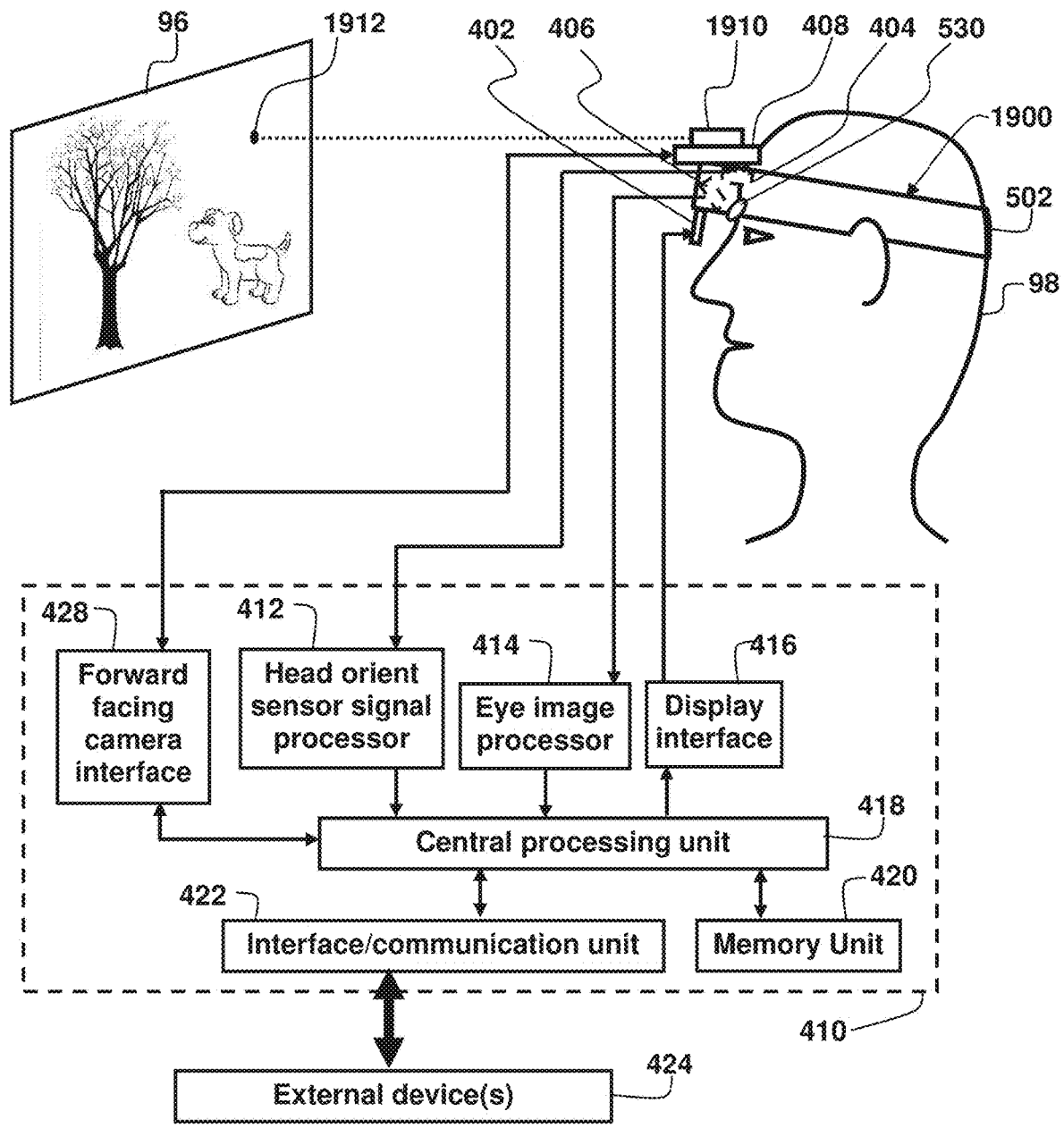
FIG. 8 shows an embodiment similar to FIG. 2 and FIG. 3, that further comprises a forward-facing camera and a light beam projector.
Figure 9:
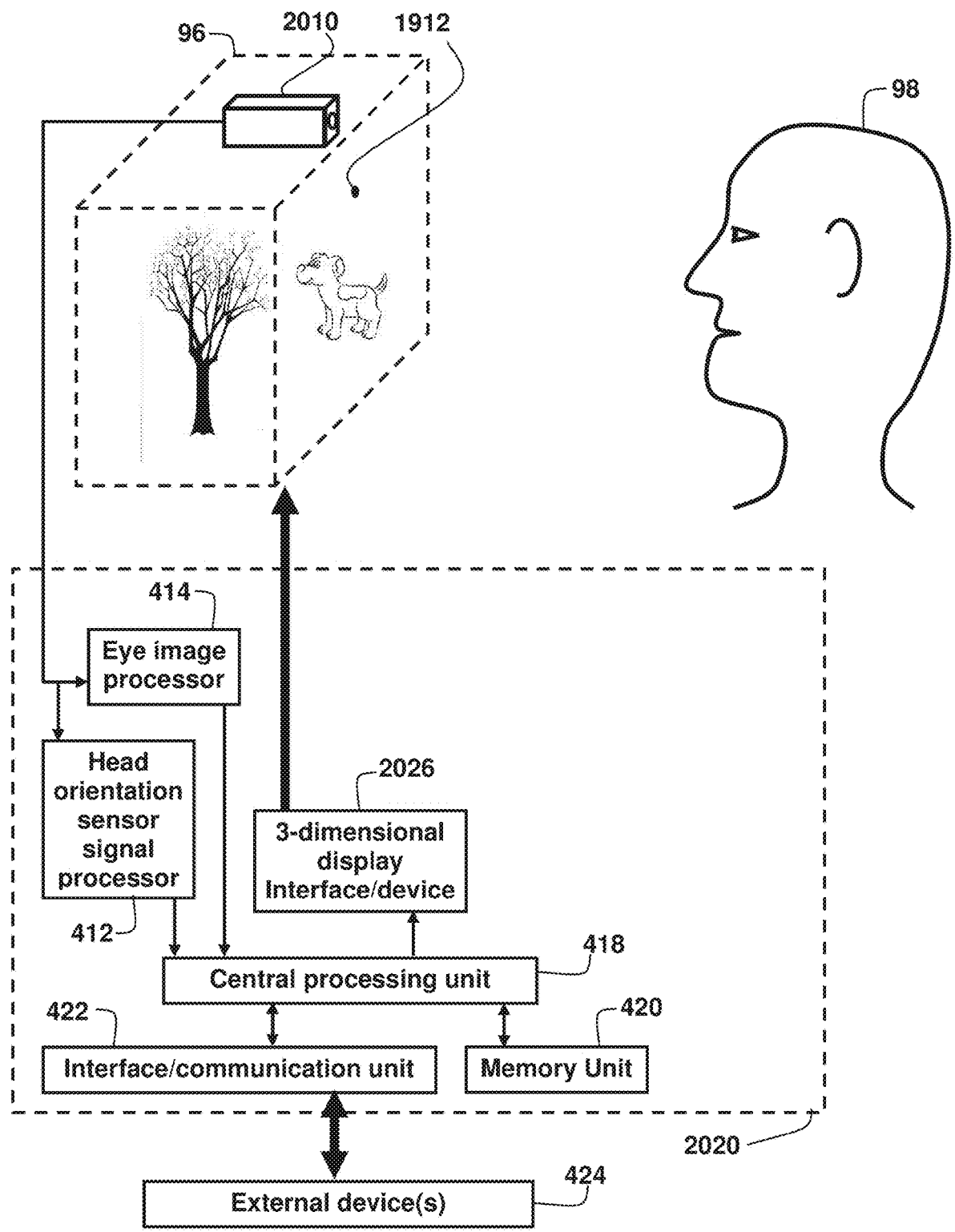
FIG. 9 is a system with an external eye imaging device and head orientation sensor.
Figure 10:
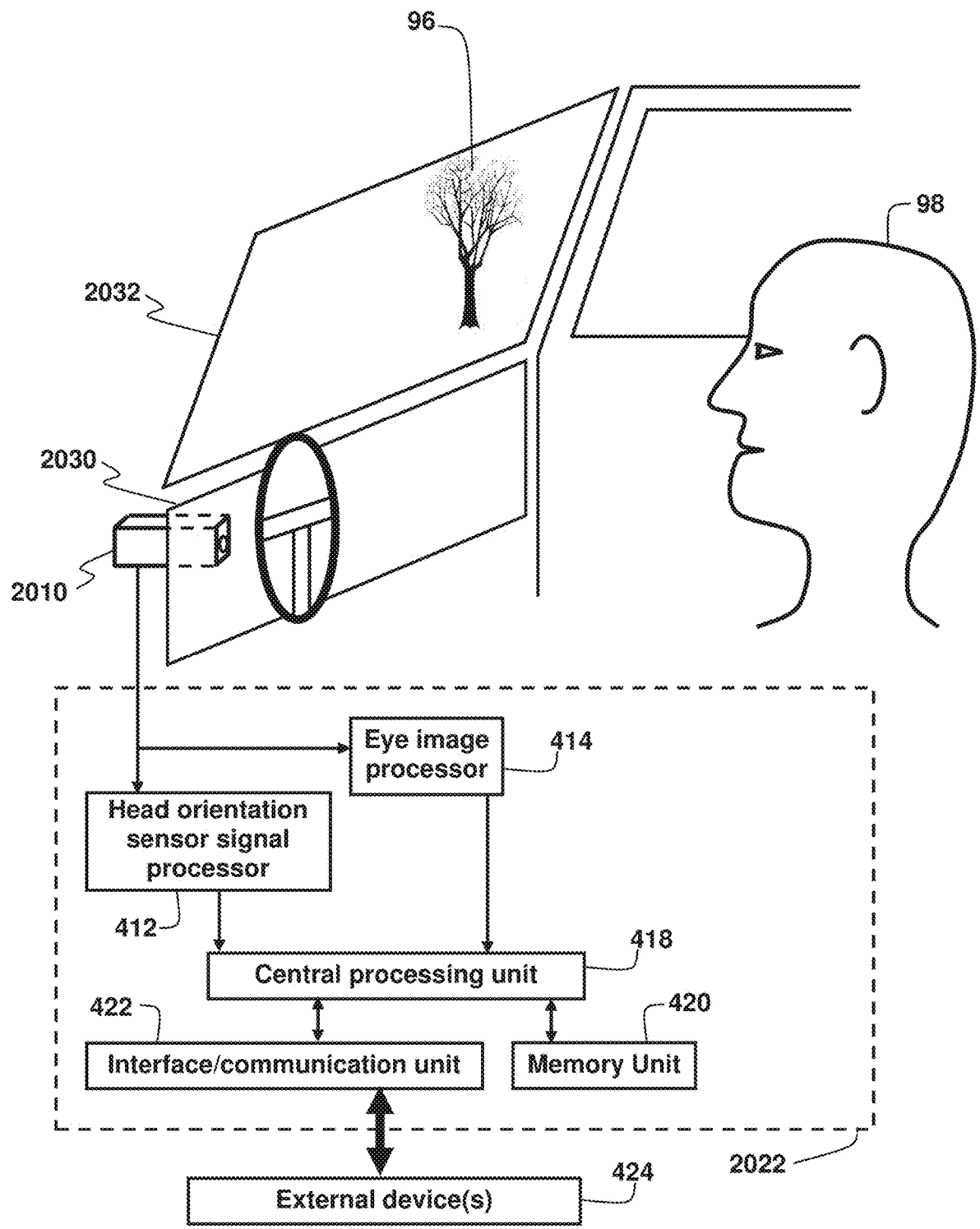
FIG. 10 shows an embodiment similar to FIG. 9 mounted in a vehicle.

FIG. 2, FIG. 3, FIG. 4A, FIG. 4B, FIG. 4C, FIG. 5, FIG. 6A, FIG. 6B, FIG. 7A, FIG. 7B, FIG. 8, FIG. 9, and FIG. 10 illustrate examples of systems for observing eye and head information, comparing this information to measure ocular parameters, and determining human health, such as a neurologic condition, using the method that was shown in FIG. 1. In these systems, the head information is compared to the eye information. In embodiments, the left eye information can be compared to the right eye information. In these systems, eye observation can be used to determine eye position, eye movement, pupil size, and/or eyeblinks. The eye information is collected from an eye sensor which can be of any type as described herein. Such eye information can be determined from sensing characteristics of the eye. The system can comprise any wearable platform (e.g., apparatus) of the types described herein, or capable of being understood by anyone skilled in the art. FIG. 9 and FIG. 10 show that it is also possible to have embodiments that do not comprise a wearable apparatus. Such embodiments can include but are not limited to an external device embedded with eye imaging and head orientation sensors from the group of smart phone, or nearby electronic device or vehicle which can view and record subject's eyes and head information.

Figure 2:
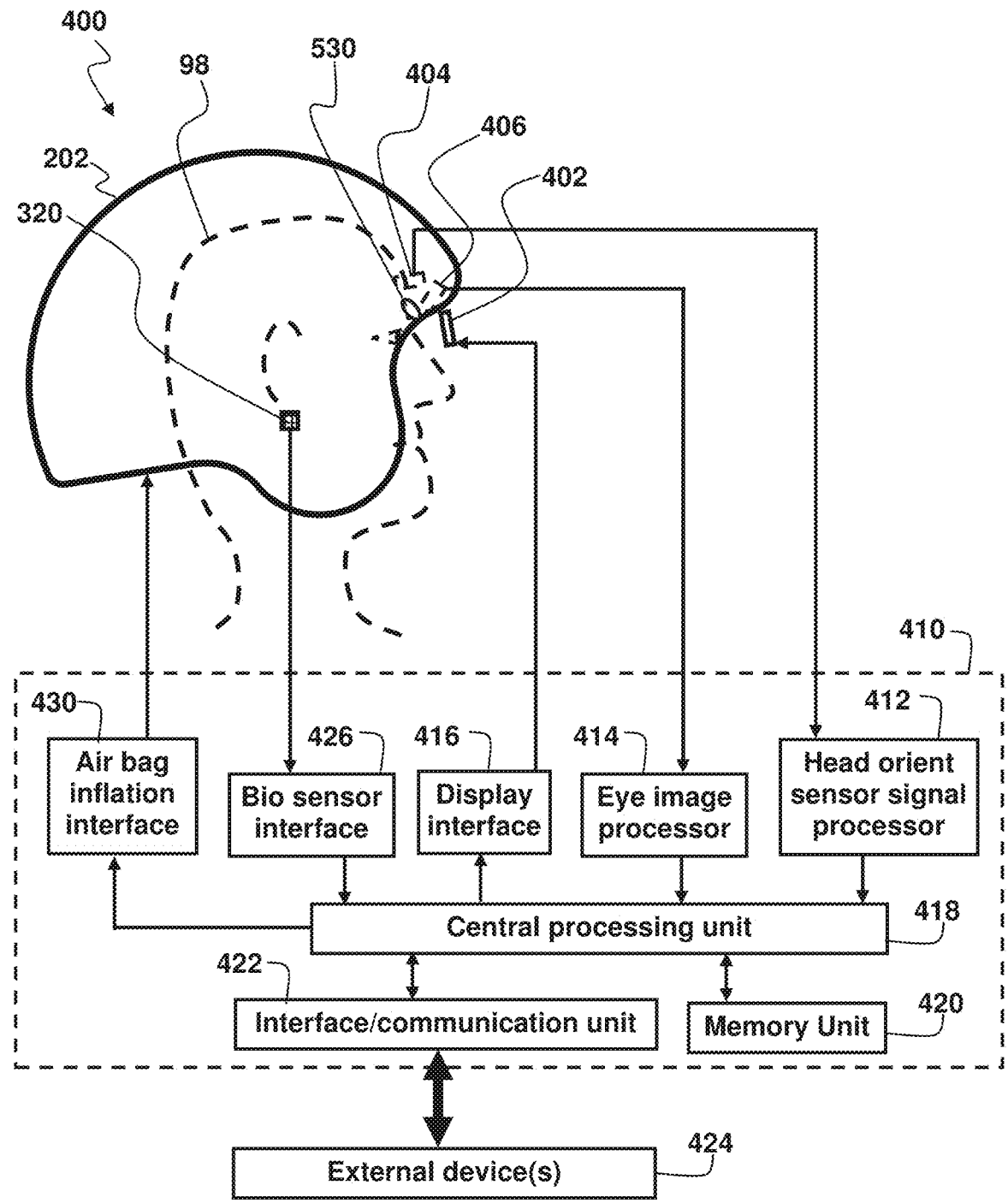
FIG. 2 is a helmet comprising an ocular parameter measuring system with display.

FIG. 2 shows a helmet, that comprises an ocular performance-based measuring system. Referring in more detail to FIG. 2, the helmet comprising an ocular performance measuring system 400 is shown on the head 98 of a person. The ocular performance measuring helmet 400, can comprise a helmet outer shell 202, a see-through display 402, which could also represent a visor or augmented reality display system, a head orientation sensor 404, an eye imaging device 406, and an illumination source 530. The ocular performance measuring helmet 400, is designed to fit snugly on the head of the person 98 so that all changes in head orientation result in equal changes in orientation of the helmet 400. The head orientation sensor 404, is rigidly attached to the helmet 400. In at least one embodiment, the head orientation sensor 404, senses (is responsive to) pitch, roll, and/or yaw. Pitch can be described as upward or downward movement of the face. Roll can be described as rotation of the face when viewed from the front. Yaw can be described as leftward and rightward movement of the face when viewed from the front. The head orientation sensor 404, can be constructed from one or more elements or it can be monolithic. The head orientation sensor 404, can comprise an inertial measurement unit (IMU or "tracker") comprising one or more accelerometers, gyroscopes, magnetometers, or any other relative or absolute position, velocity, or acceleration sensing device capable of being understood by anyone skilled in the art. In one embodiment, the orientation sensor comprises a micro-electro-mechanical system (MEMS) integrated circuit. The IMU can be configured to measure one or more DOF (such as position, velocity, orientation, and/or gravitational force, by using one or more sensors. A MEMS (micro electro-mechanical system) gyroscope, a MEMS accelerometer, and a MEMS magnetometer can be used as complementary and/or redundant sensors to accurately support a full range of motion in a three-dimensional space, measuring nine degrees of freedom (DOF). The input signals from the accelerometer(s), magnetometer(s), and gyroscope(s) in these nine DOF IMUs can be processed using a Kalman or a Madgwick filter located in a head orientation sensor signal processor 412 to provide output signals that have been optimized for accuracy, stability, and response rate.

The ocular performance-based measuring system 400 can be mounted to the helmet 202, or any other head worn device in numerous configurations. When used with display systems discussed in this document, the display 402 can refresh on-screen images at a rate of 60 Hz-360 Hz. Reducing the lag between head movement and the headset response will mitigate symptoms of motion sickness or visually induced motion sickness. The resolution use can be variable depending on the application or platform used but may be chosen as 1080×1200 or 2160×1200-2560×1440 or higher and the latency between images should be short (20 milliseconds or less). The sampling frequency of eye imaging device (tracking system) 406 can be 60 Hz-5000 Hz (e.g., frames per second). For performing some tests, such as the head impulse test, a sample rate or refresh rate of 250 Hz or higher might be necessary to capture the subtle eye movements, such as overt and/or covert saccades.

Further referring to FIG. 2, in one embodiment, the eye sensor 406, is more specifically an eye imaging device, comprised of at least one opto-electrical transducer that receives visual information from at least one of the eyes of the person. The eye sensor 406, can be responsive to any eye position, including vertical movement of the eyes (which represents pitch), rotation of the eyes (which represents roll), and horizontal movement of eyes (which represents yaw). It can also be responsive to eyeblinks (e.g., closing, and opening eyelids). There can be one eye imaging device 406, that monitors only one eye, one eye sensor camera 406, with a wide angle, that can monitor both eyes or two imaging devices, one to monitor each eye. There can also be multiple eye imaging devices, to monitor different areas of each eye (e.g., eye response sensors tracking pupil features and corneal reflection surfaces). The eye imaging device 406, can be positioned anywhere around the eye, and can utilize visible or invisible light, such as infrared light. In one embodiment, the helmet system shown at 400 further comprises an illumination source to help illuminate the eyes of the person, and this illumination source 530 could project infrared light, near infrared light, or visible light in the direction of the person's eyes to help improve the sensitivity of the eye imaging device 406 and make it less sensitive of other light sources, which may produce noise and/or glint. An example, and further description of such an illumination source, is shown at 530 in FIG. 2, and further described with reference to FIG. 4B and FIG. 8 but could be used with any of the embodiments described herein. Furthermore:

(a) The eye imaging device (sensor) 406 or devices, in the embodiments shown in FIG. 2, FIG. 3, FIG. 4B, FIG. 5, FIG. 6A, FIG. 8, as well as seen with 2010 in FIG. 9, FIG. 10 and described in this document, could be configured to operate at a high frame rate for measurement of any ocular parameter and used with any of the embodiments described herein. It is desirable for the eye sensor or sensors to have a sampling rate at least 90 frames per second (90 Hz) and preferably at least 120-500 Hz. More typically a sampling rate at 120 Hz-5000 Hz or higher may be needed to capture fixation of ocular parameter movements or correctly measure other saccade dynamics or capture the detail of the very rapid eye movement.

(b) The eye imaging device 406 or sensors could be configured for receiving a reflected signal, such that the magnitude of electrical signal is based on reflected light intensity.

(c) The eye imaging device 406 or sensors can include more than one detection region and provide more than one electrical output signal.

(d) To determine the characteristics of the eye or surface features of the eye, such as the cornea, limbus, sclera or pupil, the eye imaging device 406 or sensors should be positioned below the plane of upper lid margin, in order that the reflected light is tracked and not obstructed by the overhanging upper eyelid.

(e) The eye imaging device 406 or sensors can be configured to detect reflections/glints, textural patterns, and/or blood vessels from the characteristics of eyes (cornea, iris, limbus, sclera, pupils, blood vessels of the retina).

(f) The eye imaging device 406 or sensors could be comprised of reflecting elements, such as mirrors, or diffracting elements such as lenses, prisms, diffraction gratings, beam splitters, scanners, and/or opto-micro-electro-mechanical system (MOEMS).

(g) If multiple eye imaging devices are used, each eye imaging device 406 could be configured to estimate the gaze independently.

(h) The system could use eye imaging devices that track different locations on the surface of one or both eyes to determine gaze-tracking locations, utilizing multiple illumination sources and/or sensors to generate and observe glint/reflections from multiple directions which can be used improve the accuracy of gaze tracking.

(i) The eye imaging device 406 or sensors could be used to obtain anatomic structures and characteristics of the eye, movements of the eye and eyelids, responses and reflexes of the eyes and eyelids.

(j) The eye imaging device 406 or sensors could have an angular precision of smaller than one degree.

(k) Eye tracking using binocular horizontal and vertical eye position estimates can be derived from the relative positions of multiple corneal reflections, the limbus, and/or the pupil.

(l) Using an algorithm, the three-dimensional eyeball position can be estimated by one or more corneal surface reflections (or glints).

The eye imaging device 406 or sensors could be a video camera or cameras. It can be appreciated and understood by those skilled in the art that a video camera is an imaging device that has at least one opto-electric transducer configured for converting a light signal to an electrical signal. In the case of professional video cameras in common use from the 1930s to the 1990s, this involved the use of a scanner to sequentially scan a projected image of a scene and record it using a single opto-electric transducer. Many modern video cameras apply this same concept by using multiple opto-electric transducers in an array (typically a charge conducting device or CCD). The scanning technology in the video cameras is like the scanning technologies that use a single beam light source that is scanned across the eye, either by moving the beam source or by using a mirror to move the point at which the beam is pointing. If a mirror is used, it could be mechanically moved by a system such as a micro-electronic mechanical system (MEMS) device. The resulting scanned reflection off the eye can then be detected using a photodetector, which is an example of an opto-electric transducer that converts an optical signal into an electrical signal.

In the embodiment shown in FIG. 2, the see-through display 402, head orientation sensor 404, and eye imaging device 406, are connected to an electronic module 410. The electronic module 410, comprises a head orientation sensor signal pre-processor 412, that is connected to the head orientation sensor 404, an eye image processor 414, that is connected to an eye imaging device 406, and a display interface 416, that is connected to the display 402. Inside the electronic module 410, the head orientation sensor signal processor 412, the eye image processor 414, and the display interface 416, are connected to a central processing unit 418. Also connected to the central processing unit 418, is a memory unit 420, and an interface and/or communications unit 422. The memory unit 420, can store multiple readings and results, which can be used for data logging, tracking of multiple users, and tracking of performance at various times. The interface and/or communications unit 422, can be connected to an external device 424. Transmission of signals between the communications unit 422, and the external device can be through a wired connection or a wireless connection using any connection method and/or protocol capable of being understood by anyone skilled in the art, including, but not limited to a serial protocol (such as USB), an ethernet protocol (such as TCP/IP), and a cellphone protocol (such as LTE). Additional elements that are not shown but might be included in the electronic module 410 can be a battery, a battery charge level indicator, and a power management module. The worn device can contain a dual-purpose charging/connection port and this port could comprise a universal serial bus (USB) connection. It could be wirelessly charged, or it could use any other connection capable of being understood by anyone skilled in the art. The connector on the other side of the charging cable could be a standard rectangular USB connector. The connection could be USB 3.0 or better. Communication between the electronic module 410, and the wearable device can be through a wired connection or a wireless connection using any connection method and/or protocol including, but not limited to those described for the connection between the interface/communication unit 422, and the external device 424.

Note that the embodiment of the helmet shown at 400 in FIG. 2 could also comprise one or more additional sensors, such as the additional sensor shown at 320. Such an additional sensor 320 or sensors, could detect biometric, physiologic and/or biochemical parameters of the wearer of the helmet. The additional sensor(s) 320 could be connected to the electronic module 410, and more specifically to a biosensor interface 426, that communicates with the central processing unit 418, and the other parts of the system described herein.

In embodiments, biochemical sensors and/or physiologic sensors in contact with the skin can provide human health information that can be correlated with ocular parameter measurements to detect the specific biochemical or physiologic abnormality. These specialized sensors can communicate with the display system to provide specific information regarding the biochemical or physiologic health status. These sensors can also be attached to the display device, in contact with the skin, and on other specific anatomic areas of the body. These sensors can be strategically placed on anatomical structures for the parameter they were designed to detect and measure. As an example, when measuring the pulse rate or blood pressure the sensors are placed over a major artery (such as the superficial temporal or occipital artery). As another example, sweat provides a significant amount of information about a person's health status and is readily accessible, making it suitable for wearable, noninvasive biosensing. Sweat contains important electrolytes, metabolites, amino acids, proteins, and hormones, which allows monitoring of metabolic diseases, or a person's intoxication level. Some anatomic areas of the body have a higher concentration of eccrine sweat glands, such as on the forehead, temporal area and back of the neck. Skin sensors strategically placed on these anatomic areas of increased sweat glands are ideal for measuring dilute electrolyte solution with primary components of bicarbonate, potassium, and sodium chloride, glucose, pyruvate, lactate, cytokines, hormones such as cortisol and immunoglobulins. The skin sensors can detect abnormal biochemical measures including simple monosaccharides (sugar) or dextrose, metabolites, proteins, and electrolyte abnormalities which can be correlated with eye and head tracking measurements to provide information about the health of the individual. Additionally, sensors used to detect and measure other physiologic properties of the user, can be anatomically positioned for the intended specific physiologic measures. These sensors can detect such abnormal physiologic measures as arterial pressure, thermal changes, changes in cardiac activity, such as arrythmia, atrial fibrillation, atrial flutter, cardiac arrest, or the rate of inhalation and expiration. Other sensing elements/transducers, in contact with the scalp or using evoked Potentials (EP), can detect and measure abnormal changes in cranial, motor, or sensory function, mental status, non-focal and focal neurologic changes, abnormal waveform frequency of the cerebral cortex, spike analysis, and electrophysiologic measurement of cerebral activity. These sensors can also communicate with the display system and can be correlated with the ocular parameter measurement to detect abnormalities of the human health.

The embodiment of the helmet shown at 400 in FIG. 2 could further comprise an airbag, such as an airbag. FIG. 2 does not specifically show an airbag (in order to keep this illustration simpler), but it can be understood that such an airbag would typically be located outside of the shell 202, which is shown in FIG. 2. The airbag would require an inflation interface, which is shown at 430 in FIG. 2. The inflation source is responsive to the central processing unit 418. The airbag inflation interface 430 could inflate the airbag in response to the detection of an impact by the head orientation sensor processor 412, or in response to an infrared sensor, an acoustic sensor, or other device configured for sensing an impact before it occurs, such as a proximity detector, video camera, or information from the helmets of other players on a sports field.

Figure 3:
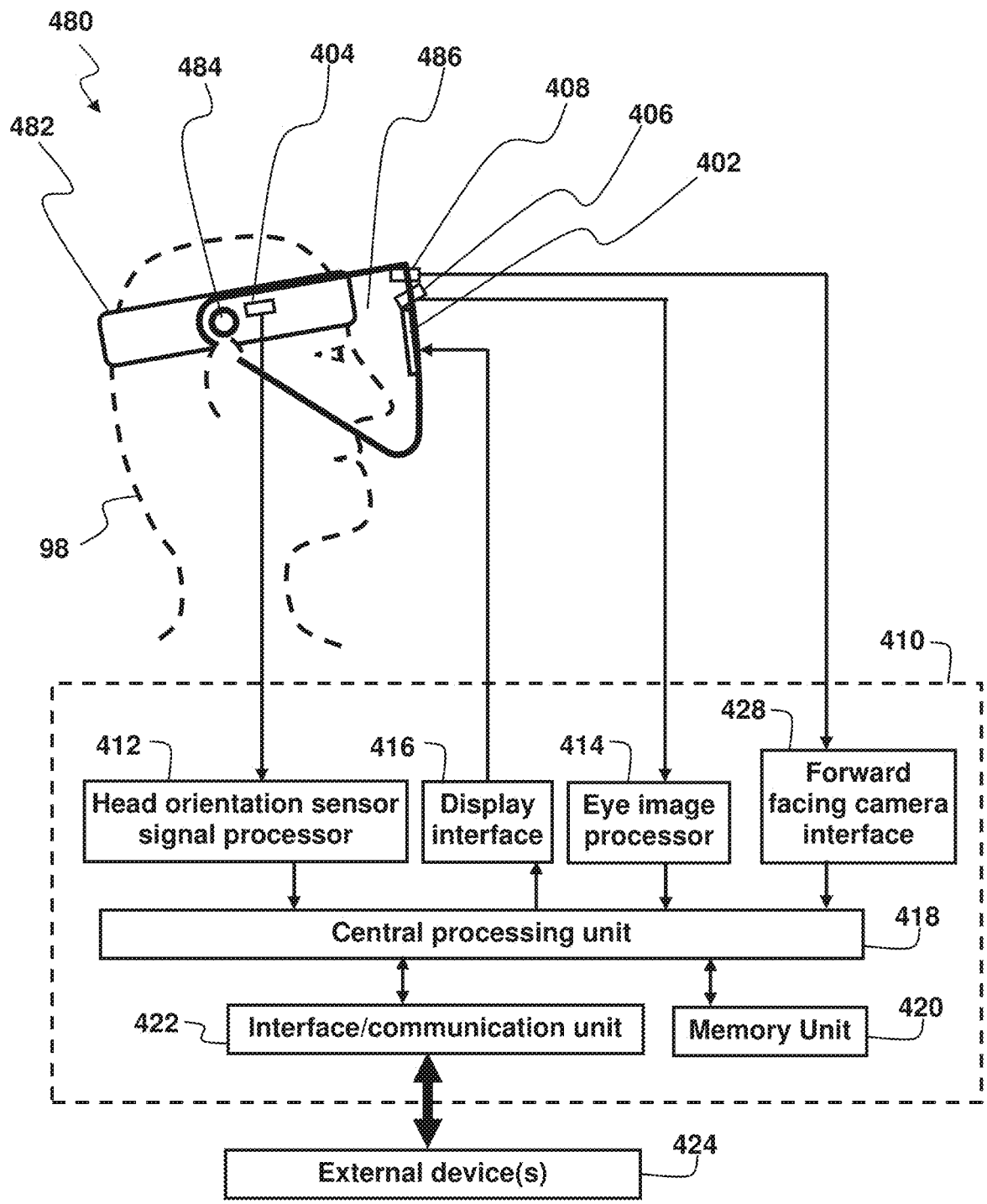
FIG. 3 shows a visor or face shield-based ocular parameter measuring system.

Features of the system and methods described herein could also be used in a face shield-based embodiment, such as the face shield system shown at 480 in FIG. 3. This embodiment could also comprise an augmented reality display. In this embodiment, a head attachment member for the face shield is shown at 482. The head attachment member 482 could be rigid. The head attachment member 482 can be attached to a see-through shield 486 using pivotable linkages 484 on each side of the head attachment member 482 to allow the shield 486 to be rotated up out of the line of sight. The see-through shield 486, could comprise transparent or translucent materials. The face shield system 480 can comprise eye imaging elements and/or transducers for detecting and measuring eye position and eye movements and a head orientation sensing element/transducer and circuitry to the electronic elements such as:

the head orientation sensor shown at 404, connected to the orientation sensor signal processor 412;

the eye imaging device 406, connected to the eye image processor 414; and the central processing unit 418, memory unit 420, and interface/communication unit 422 for communicating with an external device 424.

The face shield-based system 480 of FIG. 3, could have other biochemical or physiologic sensors (320 in FIG. 2) interfaced with the electronic module 410, in the same way as was described for the helmet-based system in FIG. 2, to detect biochemical and/or physiologic impairments. In another embodiment, the face shield-based system 480, could have a display 402 and display interface 416 implemented in the same way as was described for the helmet-based system of FIG. 2. The display could be a see-through display and could be used for augmented reality. As an alternative, the face shield-based system 480, of FIG. 3 might have a forward-facing camera 408, that communicates with a forward-facing camera interface 428, in the electronic module 410. The eye imaging device 406 can be responsive to the forward-facing camera 408 to measure the ocular performance. In this case, the central processing unit 418, or the external device 424, could combine the information from the head orientation sensors 404, the eye imaging device 406, and the forward-facing camera 408, to determine one of the ocular performance parameters described herein. The face shield-based system could also comprise an illumination source similar to the illumination source shown and described with reference to 530 in FIG. 4B. This illumination source could project infrared light, near infrared light, or visible light in the direction of the person's eyes to help improve the sensitivity of the eye imaging device 406 and make it less sensitive of other light sources, which may produce noise and/or glint.

Figure 4A:
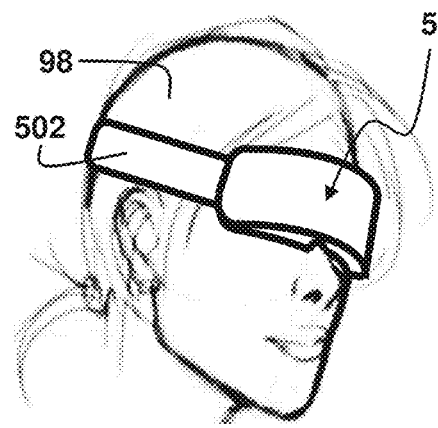
FIG. 4A shows a goggles embodiment of a wearable virtual reality device.
Figure 4B:
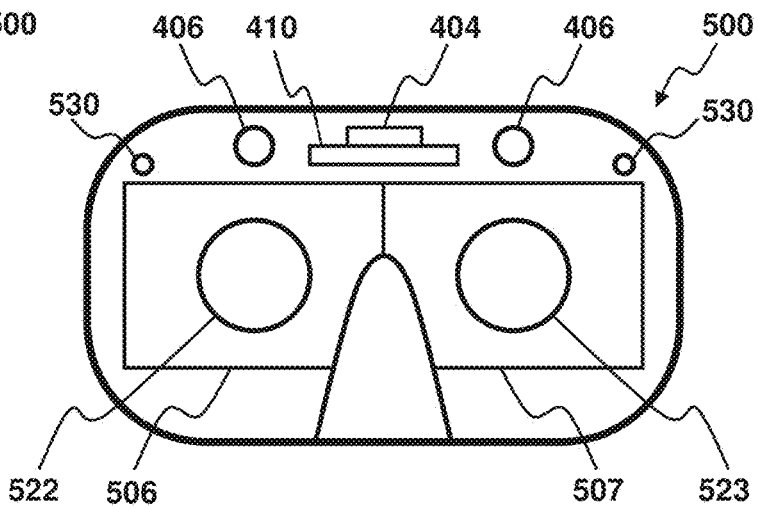
FIG. 4B shows the device of FIG. 4A when viewed from inside the goggles looking out.

FIG. 4A and FIG. 4B show virtual reality (VR) goggles embodiment of a wearable device for measuring human ocular parameters. FIG. 4A shows the wearable device 500, attached to a person's head 98, with a strap or headband 502. In the device shown in FIG. 2, the display (402) was a see-through display and it only covered one eye or part of an eye. In the device of FIG. 4A and FIG. 4B, shown at 500, the left virtual reality display, shown at 506 and right virtual reality display 507, are opaque and the person is typically completely immersed in the scene being displayed. Other than the difference in displays, the VR goggles embodiment in FIG. 4B, can have many of the same elements and configurations that were described with respect to FIG. 2 and FIG. 3, including but not limited to the head orientation sensor 404, the eye imaging device(s) 406 (of which there can be one for the left eye and one for the right eye), and the electronic module 410. For the person's eyes to be able to focus on the displays (506 and 507), there are typically two lenses 522 (left eye lens) and 523 (right eye lens) between the person's eyes and the displays, 506 and 507, when the VR device 500, is worn normally by the person. Because the interior of the VR device 500 is not exposed to external light, there can be one or more illumination source(s) 530, to provide light that can be used by the imaging device(s) 406 to sense ocular parameters such as eye position, or pupil size, and/or eye or eyelid (e.g., eyeblink) motion or any of the other ocular parameters described in other parts of this document. The illumination source or sources 530, can use infrared, near infrared, or visible light. Ideally, the eye imaging sensor 406 would be below the upper lid margin of the user's eyelid to best capture the characteristics of the eye, and the illumination source 530 should be below the eye imaging sensor 406. Other attributes of the illumination source (light source) can include:

(a) The light source 530 may be positioned along an optical axis that is centered when the pupil is looking straight or off the optical axis.

(b) The light source 530, or sources can generate infrared (IR) light, short-wavelength infrared (SWIR), near-infrared light (NIR), NIR-filtered broadband light, visible light, light-emitting diodes (LEDs), red, blue, and green (RBG) lasers, diode lasers and/or fiber lasers.

(c) The light emitted by the light source 530 can be continuous or pulsed or used in any combination with the different light sources.

(d) The light source 530 can comprise a light collimator.

(e) The system can also scan different resolutions of infra-red light to different portions of the eye.

Referring specifically to the left and right eye imaging device(s) 406 in FIG. 4B, these eye imaging devices (more generally eye sensors) can be used for more than just the tracking of eye position and eye movement in response to head movement. The eye sensors 406 can also be used to perform the following functions:

(a) The eye sensors could be used to provide control information. For example, the position of one or both eyes (or the orientation or movement of the eyes and/or eyelids) could be used to determine which of a plurality of choices a user has selected in a menu of options presented on a display. This selection could be to change the scene being displayed to the user. This selection could be used to turn something on or off.

(b) The eye sensors could be used to image one or both retinas of the person, to capture anatomic characteristics of a retina, to capture motion and/or orientation of a retina, and/or to determine retina image stability and/or foveal fixation.

It should be noted that embodiments of the present invention can be implemented using video cameras for the imaging devices, shown for example at 406 in FIG. 2, FIG. 3, and FIG. 4B, or imaging devices which are not video cameras. Examples of non-video camera eye imaging sensors can include opto-electrical transducers, photodiodes, photodetectors, and electromagnetic trackers. Embodiments of the present invention could also be implemented with the use of a virtual retinal display providing an image directly on the retina of the user's eye.

Figure 4C:
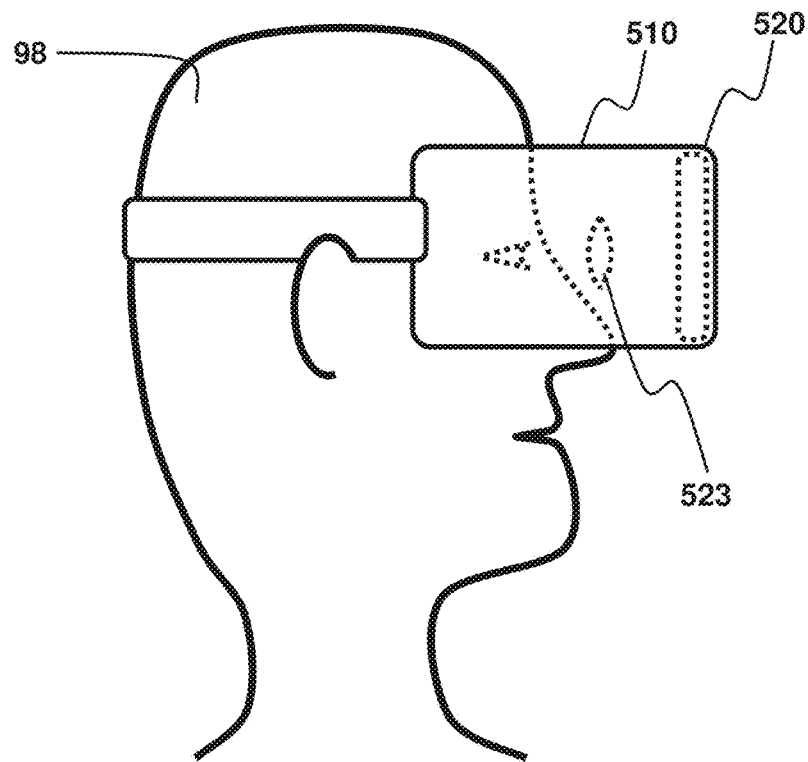
FIG. 4C shows wearable virtual reality goggles comprising a smartphone.

FIG. 4C shows wearable virtual reality goggles 510, comprising a smartphone 520. These goggles 510, use the smartphone 520, to provide the display, the eye imaging device (in the form of a user-facing camera), and the head tracker functionality, and doing many or all of the functions of the electronic module. To help the person's eyes focus on the display of the smartphone 520, these virtual reality goggles further comprise one or two lenses 522 and/or 523, that sit between the eyes of the person's head 98, and the smartphone 520. In the embodiment shown in FIG. 4C, the smartphone 520 can contain embedded software to perform all the necessary functions of measuring all eye movements and/or ocular functions as well as measuring head movements. As an example, head orientation and eye position and movements can be detected and measured to perform the ocular parameter measurements discussed in this document. Instructional signals, such as when to rotate the head while looking a visual target, can be random to prevent the subject from anticipating the timing, in the form of visual cues, auditory signals or a haptic signal. Calibration and other specific ocular parameters test measures can similarly be performed with the smart phone application. Data obtained can be logged and transmitted wirelessly to another smart device.

Figure 5:
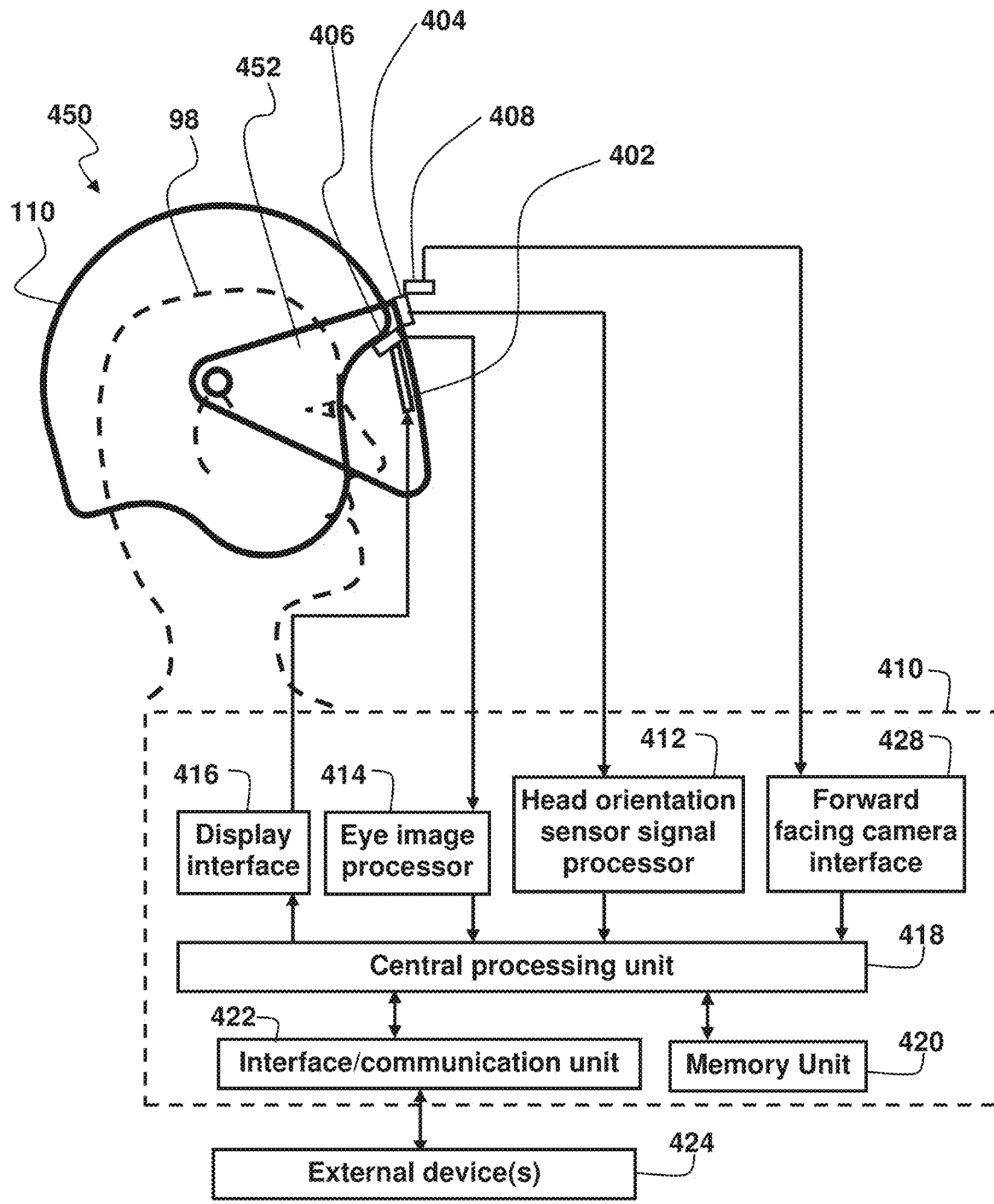
FIG. 5 shows a face shield that comprises an ocular performance measuring system.

FIG. 5 shows a face shield or visor embodiment of an ocular performance measuring system wearable augmented reality device 450. The face shield system 450, shown in FIG. 5 is similar to the helmet system. 400 in FIG. 2, and the see-through display, 402 in FIG. 5 and could have any of the features and attributes of these other embodiments. The face shield system 450, could be electronically coupled to the electronic module 410, and this electronic module 410, could be part of the face shield system 450, or the electronic module 410, could be external to the face shield system 450, and communicate through a wired or wireless connection.

The electronic module 410 shown in FIG. 5 can comprise a display interface 416, an eye image processor 414, a head orientation signal processor 412, a forward-facing camera 428 interface, a central processing unit 418, a memory unit 420, and an interface and/or communication unit 422 as shown and configured in FIG. 5. The electronic module 410 can be configured to communicate with an external device (or devices) 424 using any of the methods and systems described herein.

Figure 6A:
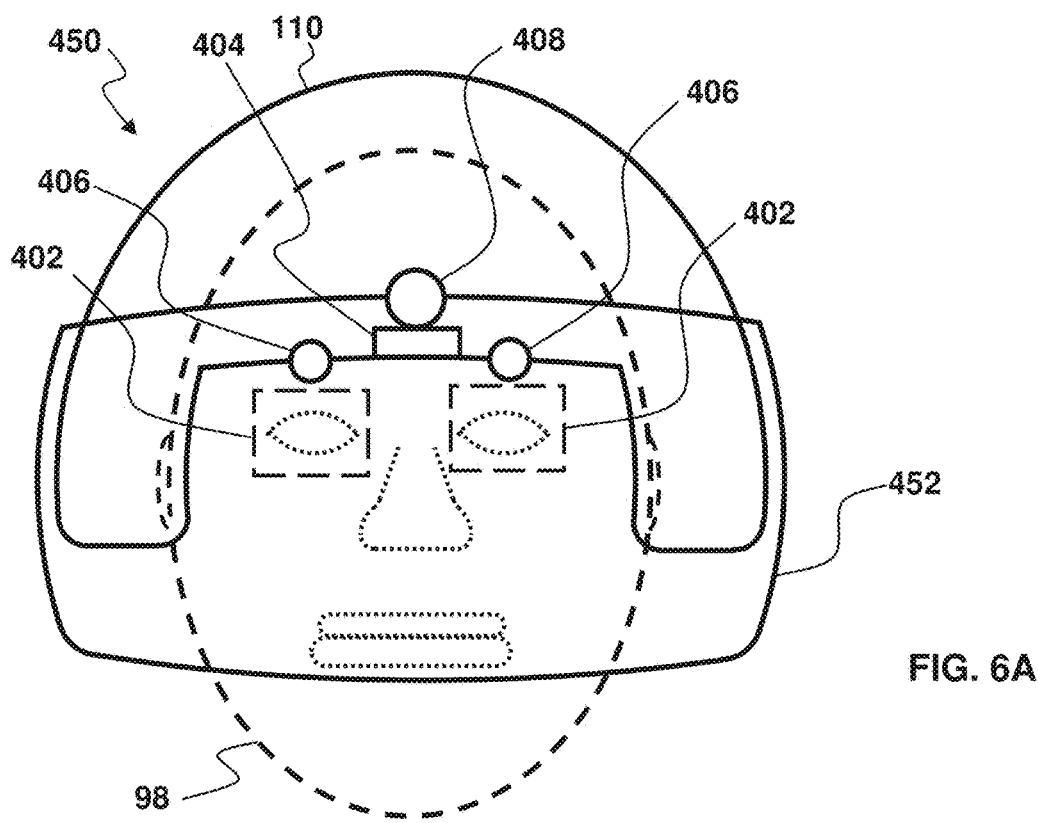
FIG. 6A shows a face shield having light emitting diode see-through display panels.

FIG. 6A shows a front view of the face shield system 450 of FIG. 5, without the electronic module. The face shield system 450 in FIG. 5 and FIG. 6A, could be used for measurement of any human ocular performance parameter described herein. The face shield system 450 shown in FIG. 5 and FIG. 6A is configured to be worn on a person's head 98. The face shield system 450 can comprise: a see-through display 402: a head orientation sensor (head tracker) 404: an eye imaging device 406, which could more specifically be an eye imaging device with opto-electric transducer and photodetector; a forward-facing camera 408; a face shield or visor 452, and a helmet 110. The helmet 110 in FIG. 5 and FIG. 6A could be a helmet of the embodiment shown at 202 in FIG. 2. The helmet 110 in FIG. 5 and FIG. 6A could be any other helmet (hard or soft) capable of being understood by anyone skilled in the art. Ideally, the eye imaging sensor 406 would be below the upper lid margin of the user's eyelid to best capture the characteristics of the eye.

Figure 6B:
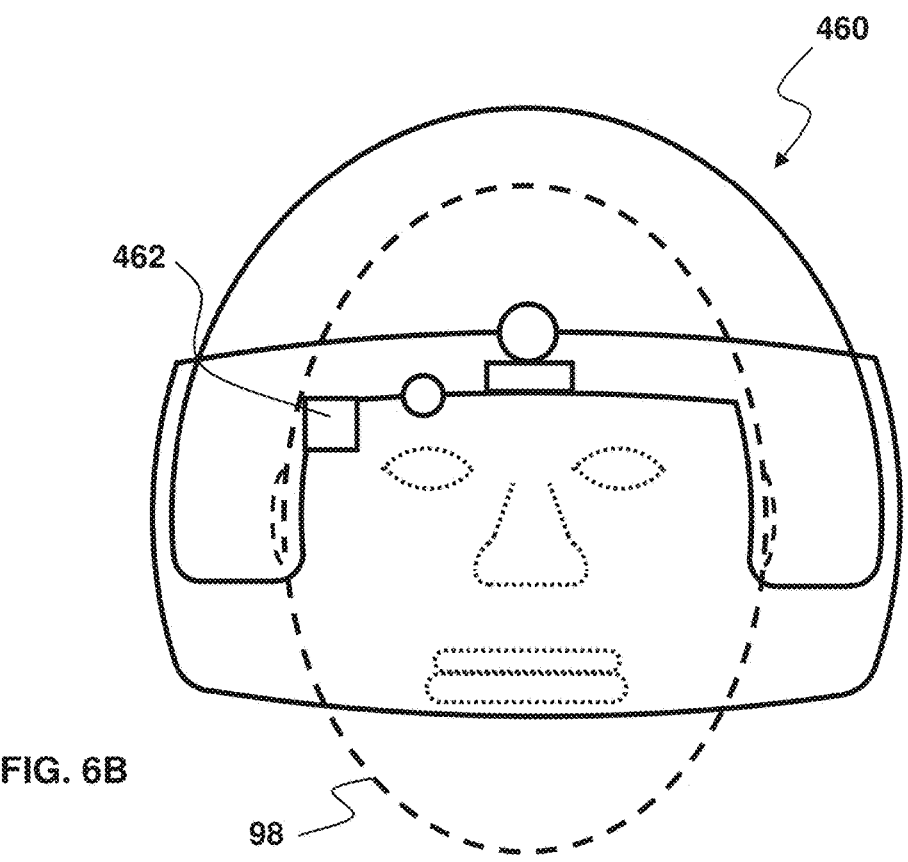
FIG. 6B shows a face shield comprising an augmented reality see-through display.

FIG. 6B shows an alternate embodiment of the system shown in FIG. 5 and FIG. 6A. This alternate embodiment could more specifically be called a face shield based augmented peripheral vision ocular performance measuring system 460. The augmented peripheral vision system 460 in FIG. 6B differs from the see-through-display-based system 450 in FIG. 6A by having a peripheral vision display element 462 in FIG. 6B instead of the see-through display (or augmented reality display) 402 in FIG. 6A. The peripheral vision display element 462 can be implemented in any way capable of being understood by anyone skilled in the art. The advantage of a peripheral vision display element 462 is that it reduces visual clutter, because it is in a person's peripheral vision and, the display element does not need to be see-through.

It is possible to have other embodiments of ocular performance-based measurement systems and methods that use some of the elements shown in FIG. 5, FIG. 6A, and FIG. 6B. An example of such an alternate embodiment would be an ocular performance-based measurement system (or method) that uses a virtual retinal display, as described in U.S. Pat. No. 5,659,327, instead of the see-through display (402 in FIG. 5 and FIG. 6A) or the peripheral vision display element (462 in FIG. 6B). Such an alternate embodiment could further include having an augmented reality display or displays in any configuration capable of being understood by anyone skilled in the art.

Figure 7A:
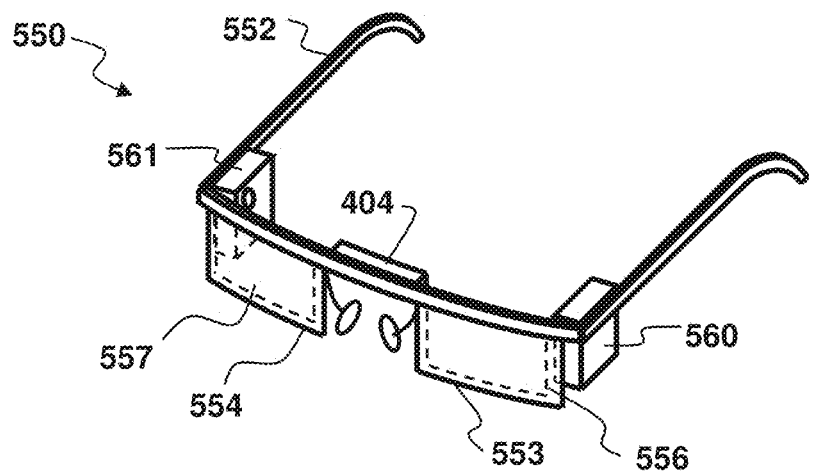
FIG. 7A shows an eyeglasses embodiment of a wearable augmented reality device.

FIG. 7A shows an eyeglasses embodiment of a wearable device for measuring human ocular performance 550 to determine human health. The eyeglasses device 550, shown in FIG. 7A is like the helmet-based device 400, shown in FIG. 2, the goggles-based device in FIG. 4B, and the face shield device 450 in FIG. 5 and could have any of the features and attributes described and shown with these other embodiments. The eyeglasses device 550 in FIG. 7A, could be electronically coupled to an electronic module 410, and this electronic module 410 could be part of the eyeglass's device 550, or the electronic module 410, could be external to the eyeglass's device 550, and communicate through a wired or wireless connection. The eyeglasses device 550, comprises a spectacles frame 552, which is attaches the eyeglasses device 550 to a person's head. The eyeglasses device 550 also comprises a left eyeglass 553, and a right eyeglass 554. The left and/or right eyeglasses could be lenses, they could be clear windows, or they could be translucent windows. Also shown are a left display 556, and a right display 557. In the embodiment shown in FIG. 7A, the displays, 556, and 557, are see-through displays that are located between the left and right eyeglass, 553, and 554, and the eyes of the person. When the displays, 556, and 557, are in this location, it is not as obvious to an outsider that the device 550 is a wearable system for measuring ocular performance. The displays, 556, and 557, could also be external to the left and right eyeglasses 553, and 554. In another embodiment, the displays. 556, and 557, could be located within the eyeglass device, 554, and 555. There could be only one display, 556, or 557. The display could be off-bore and only visible in a person's peripheral vision, such as the embodiments shown in U.S. Pat. No. 9,075,249.

Further referring to FIG. 7A, the eyeglasses device also comprises a head orientation sensor located in the bridge 404, a left eye imaging device 560, and a right eye imaging device 561. All these components can be connected similarly and, in any configuration, and combination to other embodiments described herein. The embodiments shown in FIG. 2, FIG. 5, FIG. 6A, FIG. 6B, and FIG. 7A can be considered augmented reality implementations. In these augmented reality devices, the display could be see-through or opaque. If it is opaque, it could cover part or all the field of view. If it is see-through or opaque and covers only part of the field of view, it could be in one eye or both eyes. If it is opaque and covers the entire field of view, it can only be in one eye. The augmented reality display(s) in these embodiments can provide an image of interest or a target for the user to focus on. This image of interest (or target) could be a circular object, such as a pool ball. This image of interest or target could be static (not moving) in the field of view, or it could be dynamic (i.e., moving in the field of view). In this document the visual element has the same meaning as the target visual element, visual target and/or target element.

Figure 7B:
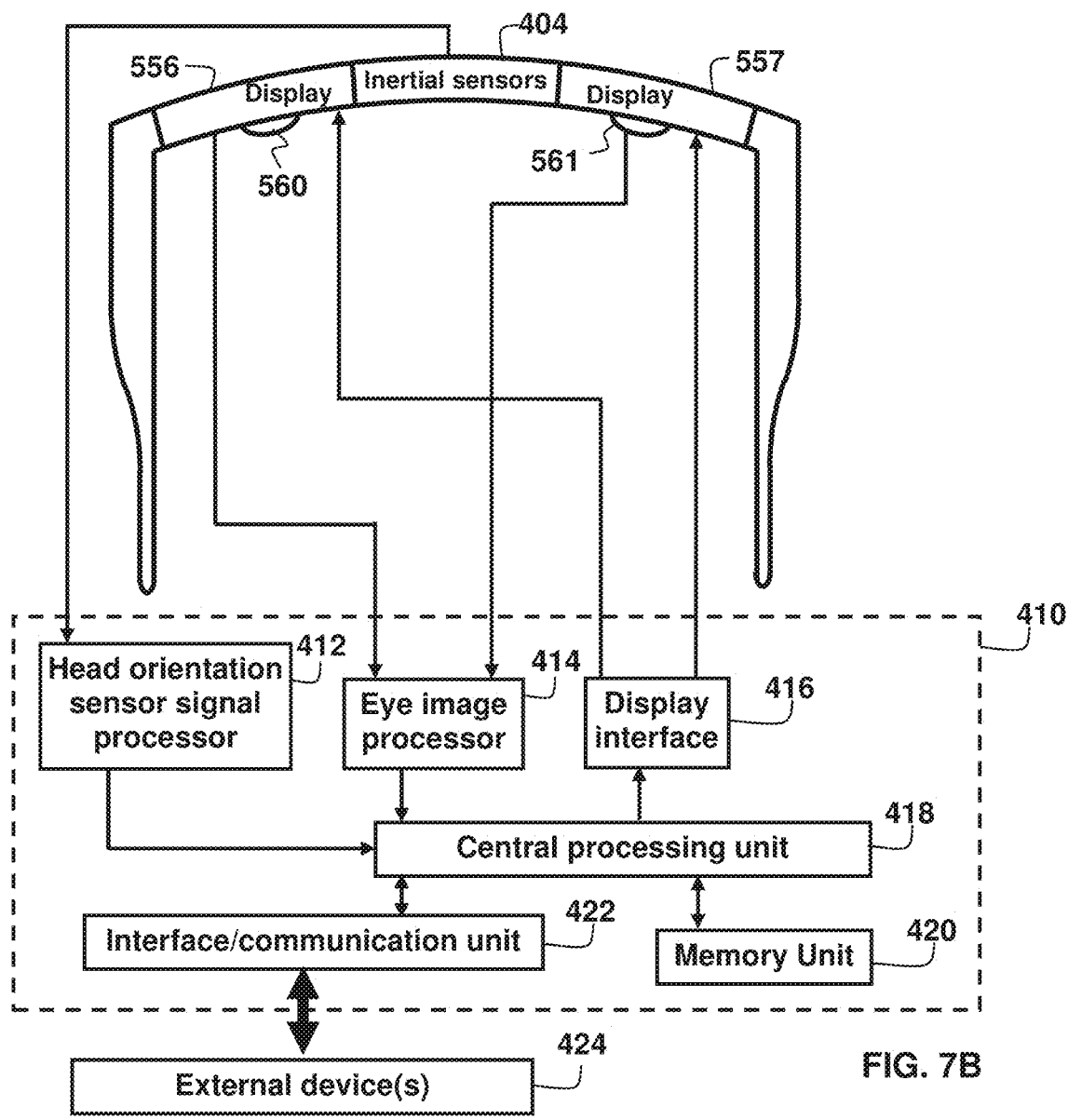
FIG. 7B shows atop view of an augmented reality or virtual reality system.

FIG. 7B shows a top view of an augmented reality or virtual reality system that also includes the main elements that were shown in the systems of FIG. 4A to FIG. 7A, including a head orientation sensor 404, a left display 556, a right display 557, a left eye imaging device 560, a right eye imaging device 561, an electronic module 410, an orientation signal processor 412, an eye image processor 414, a display interface 416, a central processing unit 418, a memory unit 420, an interface/communication unit 422, and an external device 424. An alternate embodiment can include a forward-facing camera 408, like that previously described in FIG. 9, that communicates with a forward-facing camera interface 428, in the electronic module 410. The forward-facing camera 408, can be responsive to the eye sensors to measure the ocular performance.

It should be noted that the AR and VR embodiments of the inventions disclosed herein can also be implemented using computer-generated 3-dimensional synthetic information instead of the monoscopic or stereoscopic "reality" information used for the augmented reality (AR) and virtual reality embodiments discussed herein.

Embodiments of the invention can add an image or reference marker to a scene to measure ocular parameters of the types that have been discussed previously in this document. FIG. 8 and FIG. 9 show two configurations that can be used for doing this type of measurement.

FIG. 8 shows an augmented reality system in 1900. The augmented reality system 1900 is like the embodiments described with reference to FIG. 2, FIG. 5, FIG. 7A, and FIG. 7B. The embodiment shown in FIG. 8 uses a head band 502 as the structure for head attachment and has many other components like the systems described in FIG. 2, FIG. 3, FIG. 5, FIG. 7A and FIG. 7B with the same numbers in FIG. 8 referring to the same elements, features, or attributes. The augmented reality system 1900 shown in FIG. 8 can be used for ocular parameter tests as described in other parts of this document. FIG. 8 also shows a scene 96 that is visible to the user 98. The scene example 96 shows a tree and a dog. The scene 96 can be blank. The scene 96 could be comprised exclusively of static images, such as the tree. The scene 96 could include dynamic (i.e., moving) images, such as the dog.

In addition to all of the items described with regard to FIG. 2, FIG. 3. FIG. 5, FIG. 7A, and FIG. 7B, the embodiment of the augmented reality system 1900 shown in FIG. 8 further comprises a light beam projector, shown in 1910, and a forward-facing camera, shown at 408, responsive to eye sensors to measure various ocular parameters. The light beam projector 1910, can be a laser pointer or any other source of a light that can be projected from the wearable device into the user's field of view, as depicted by the scene 96. The projected light can produce a spot or shape in the user's field of view that can serve as a reference point, a projected object that the user can focus on, as shown in 1912. The reference point or projected object generated by the light beam projector 1912, can be used as a target that the user is asked to follow or focus on as part of an ocular performance test. This reference point or projected object 1912, can be in addition to any information presented by the AR display 402, (also called a see-through display), or it can substitute for one or more of the functions of the AR display 402. For clarity, no connection has been shown between the light beam projector 1910, and the electronic module 410. However, it should be clear to anyone who understands the art that the light beam projector 1910 could be responsive to communication from the electronic module 410. Signals from the electronic module could travel to the light beam projector via a wired or a wireless connection. Such signals could control light intensity, size, shape, color, location, depth, and motion of the object 1912, generated by the light beam projector 1910, or any other parameter of the object capable of being understood by anyone skilled in the art.

Regarding the forward-facing camera, shown at 408 in FIG. 3, FIG. 5, FIG. 6A, and FIG. 8, it should be noted that this forward-facing camera 408 can be configured to record an image of the gaze point. The head orientation sensor 404, the eye imaging device 406, and forward-facing camera 408 can all communicate with each other and the electronic module 410. In the embodiments discussed herein, the forward-facing camera 408, with the eye imaging device 406, can be configured to determine, measure and log where the eyes of an individual are looking. The combination of the forward-facing camera 408 and eye imaging device 406 can be used to measure the duration of time an individual is visually focused on an object or target of interest. The combination of the forward-facing camera 408 and eye imaging device 406 can be used for measuring reaction times. The ability to focus on an object correlates with the ability to more accurately anticipate and more precisely predict movements, and therefore the ability to perform certain activities.

Further referring to FIG. 3, FIG. 5, FIG. 6A, FIG. 8, and other embodiments discussed herein, the forward-facing camera 408, can be configured to adjust its field of view, focal length, or to zoom in or out in response to an eye sensor. The electronic module 410, using the central processing unit 418, could control the forward-facing camera 408. This control of the forward-facing camera 408, could be through wired or wireless electronic signals. The forward-facing camera 408, could transmit video information to the electronic module 410, and this video information could be analog or digital information and could be transmitted through a wired or a wireless connection. Any other component in the augmented reality system shown in 1900, could also be controlled through the forward-facing camera 408. The information collected and/or recorded by the forward-facing camera 408, could also be used, in conjunction with other information collected by the augmented reality system 1900 in FIG. 8, for capturing visual images of the user's surroundings, or activate a photo or video feature of the scene 96 and determine the intended focal point of the use. As discussed previously, this determined intended focal point can be measured and correlated with the fixation accuracy of the eye tracking sensors. The user can also perform a predetermined action with the eye(s) by focusing on a specific image or orienting the eye in a specific manner as an input control. Data collected can be uploaded and transmitted to a remote or external device.

FIG. 9 shows an embodiment of a system and method that is similar to the embodiments shown previously with the functions described being performed without a wearable device. In the embodiment shown in FIG. 9, the scene 96, is produced using an electronic module 2020, that comprises a 3-dimensional (3D) display interface and/or device 2026. This 3D display interface/device 2026, could use any 3-dimensional display technology capable of being understood by anyone skilled in the art or described herein. Examples of 3D display technologies include holography and volumetric displays. Due to the realism available with 3D display technologies, the person (or subject, or user), feels that he/she is immersed in the scene 96. Non-user-worn eye tracking and head tracking can be accomplished using any of the technologies discussed in other parts of this document. The use of a video camera located above the scene 2010, is one example of such an eye tracking and head tracking technology. In this case, the eye tracking and head tracking functions are integrated in the same device. This could also be accomplished by using two separate cameras and any combination of any of the technologies discussed in this document. Non-user-worn head and eye tracking could be also accomplished using lasers, such as the use of LiDAR sensing or any of the other technologies discussed in other parts of this document. An integrated eye imaging device and head orientation sensor 2010, could be connected to an eye image processor 414, and a head orientation sensor signal processor 412, both of which can be connected to a central processing unit 418, in the electronic module 2020. The visual object 1912, which can serve as a target, as described with reference to FIG. 8 can be generated as part of the natural appearing scene 96. This target 1912, could be stationary (static) or it could be dynamic (moving). The 3-dimensional display interface 2026 in the electronic module 2020 can be configured to control the projected visual object(s) 1912 in the scene 96. The electronic module 2020 can further comprise a memory unit 420, which can be used to record display information, head orientation information, and eye information to keep a record of a test for subsequent analysis. The system shown in FIG. 9 can further comprise an interface and/or communication unit 422, which can be configured to communicate with an external device or remote devices 424. The system shown in FIG. 9 can use any of the methods described in other parts of this document to perform the ocular performance measurements that have been described in this document.

Further referring to FIG. 9, ocular parameters can be measured using static or dynamic images projected in the display scene 96, either with the head motionless or moving, or in any combination. The 3-dimensional scene can comprise a solid unobtrusive background or a background resembling typical natural activity. Any of the visual targets or visual elements previously discussed can be applied to the embodiment shown in FIG. 9. The 3-dimensional background scene, provided by the 3D display, can be limited or fully immersive with images that extend around 360-degrees around the subject as well as above the subject in a full hemispherical configuration that surrounds the subject.

Any ocular parameter that was shown and described with reference to FIG. 11, FIG. 12, FIG. 13, FIG. 16, and/or FIG. 1 can be measured using the scene 96 shown in FIG. 9. The measured visual target 1912 being viewed can be projected from the 3-dimensional display interface 2026 while the user is seemingly immersed in the scene of the holographic imaging or a volumetric display. A forward-facing camera (not shown) can be oriented to capture visual images of the user's surroundings or activate a photo or video feature of the synthetic 3-D scene and determine the intended focal point of the user. This determined intended focal point (gaze position) can be measured and correlated with the fixation accuracy of the eye tracking sensors. The user can also perform a predetermined action with the eye(s) by focusing on a specific image or orienting the eye in a specific manner as an input control.

FIG. 8 and FIG. 9 show two systems for measuring ocular parameters using a visual target in the form of a dot 1912. This target 1912 could be any other visual target of interest in the subject's field of view, such as a baseball. The target 1912 could be projected from a light beam projector 1910, as shown in FIG. 8, or could be part of the 3D scene 96, as shown in FIG. 9.

(a) The configurations shown in FIG. 8 and FIG. 9, could be used for testing vestibulo-ocular reflex (VOR), for example, by having the baseball target motionless in the center of a field and asking the user to move the head horizontally or vertically. In a similar manner, smooth pursuit can be tested by moving the baseball through space, w % bile the user's head is motionless.

(b) Alternatively, VORC can be measured when the head is moving in the same direction as the baseball movement with the same velocity.

Figure 14:
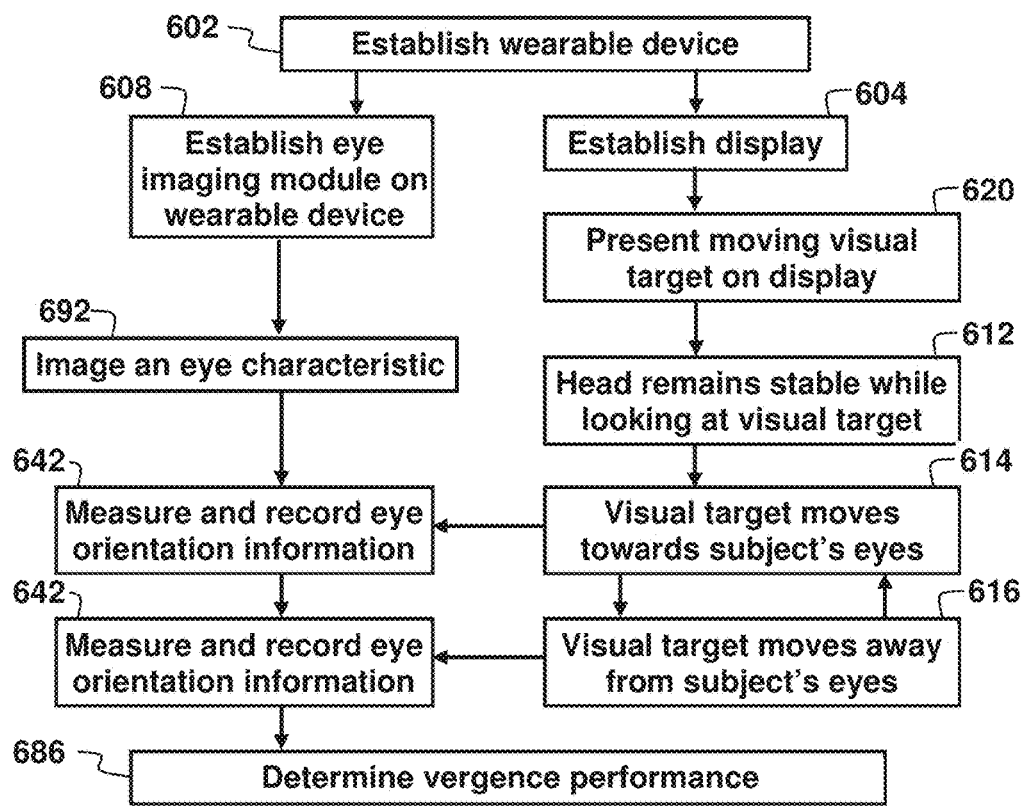
FIG. 14 shows a method for determining vergence performance.

(c) Vergence can be measured as described in FIG. 1, and FIG. 14 with FIG. 8, and FIG. 9. For example, the image of a ball can appear in the center of the scene at a distance. The ball can be moving in a straight path toward the subject or have a sinusoidal path like that in FIG. 28. As the ball appears to move closer to the subject's eyes, the ball can change in appearance, such as becoming smaller to cause convergence of the eyes. The subject's head can be stationary and only the eyes would move as while following the ball. To maintain fixation while the head is stationary, the eyes would also rotate to keep the gaze constant. As an alternative, vergence measures can be performed with the subject's head in motion as it follows the direction and speed of the ball as it appears to get closer to the eyes. As the ball appears near the head, it can move in any direction (e.g., horizontally, vertically, or at another angle and the subject's head would move in the same direction as it follows the visual target. As the ball or visual target appears to get closer to the head, there can be greater motion of the head to keep the eyes focused on the visual target. The ball could also move in a circular or rotary pattern and alter in appearance at it comes closer to the subject's face, resulting in pupillary and orientation changes of the eyes.

FIG. 10 shows an embodiment similar to FIG. 9 with the integrated eye imaging device and wearable sensor mounted in a vehicle. Referring to FIG. 10, the integrated eye imaging device and head orientation sensor shown in 2010 in FIG. 9 has been mounted into a vehicle dashboard 2030 in FIG. 10. The scene 96 of FIG. 8 is a natural scene in FIG. 10, as viewed by the person (e.g., human subject) 98 through a vehicle windshield 2032. The head orientation sensor signal processor 412, eye image processor 414, central processing unit 418, memory unit 420, and interface/communication unit 422 can have the same functions as similarly numbered elements in previous figures and can be integrated into a vehicle-mounted electronic module 2022, which can communicate with an external device or devices 424.

Figure 11:
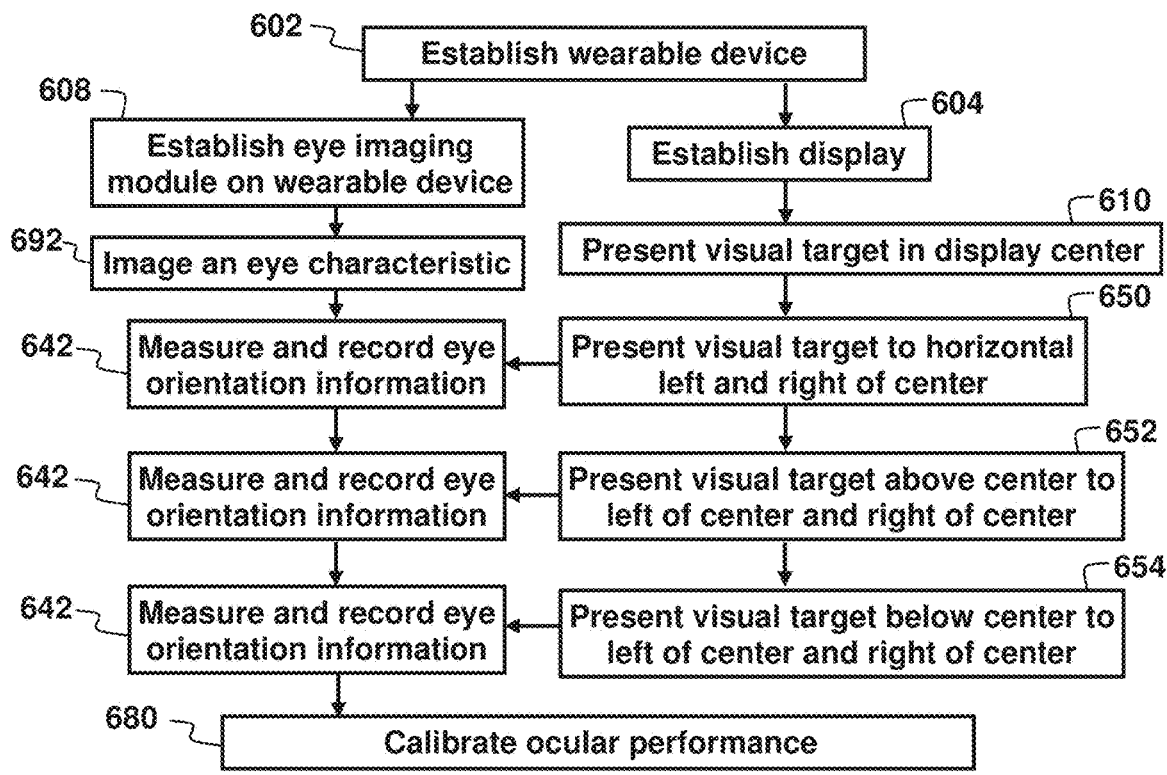
FIG. 11 shows an example of an ocular performance calibration method.

FIG. 11 shows an example of an ocular performance calibration method that can be implemented using the systems and devices illustrated in FIG. 2, FIG. 3, FIG. 4A, FIG. 4B, FIG. 4C, FIG. 5, FIG. 6A, FIG. 6B, FIG. 7A, FIG. 7B, FIG. 8, FIG. 9, and FIG. 10. It is also a more specific method than the generalized method shown in FIG. 1. This test comprises the following configuration and steps:

A wearable device 602, that comprises an eye imaging module 608 and a display 604 is established. The display background is typically subdued, plain, solid, and/or non-distracting in an ocular performance calibration test. A head orientation device 606 (not shown) can also be established on the wearable device for calibration of the ocular performance, to measure any head orientation changes, and to be sure the head remains motionless during the calibration.

Head: In this test, the subject is asked to keep his/her head motionless, or the head is constrained to keep it motionless.

Eyes: The subject is asked to track a visual target of interest by moving his/her eyes. The eye imaging module 608 on the wearable device images an eye characteristic 692 and measures the subject's eye movement 642, as visual targets are displayed.

A visual target is presented in the center of the display, as shown at step 610. The visual target 610 could be a colored dot on a solid-colored wall, for example. The visual target then behaves in the following way:

1. The visual target is initially displayed centrally as shown at step 610.
2. The visual target is then displayed off center on a first side (left or right) of the display center (typically about 20 degrees off center) as the central image is dimmed. It is then displayed off center on the opposite (or second) side of the display center as the previous image to the first side is dimmed. This is also typically about 20 degrees off center. This procedure is shown at step 650.
3. The visual target is then displayed to a center point above the middle center of the display and then displayed off the upper center point on a first side (left or right) of the display center (typically about 20 degrees off center) as the upper central image is dimmed. It is then displayed on the opposite (or second) side of the upper display center as the previous image to the first side is dimmed. This is also typically about 20 degrees off center. This step in the procedure for displaying the target in the upper central, right and left corners is shown at step 652.

4. The visual target is then moved below the initial center of the display to a lower center point, then displayed off the lower center point on a first side (left or right) of the display center (typically about 20 degrees off the lower center point) as the lower central image is dimmed. It is then displayed on the opposite (or second) side of the lower display center as the previous image to the first side is dimmed. This is also typically about 20 degrees off the lower center point. This step in the procedure for displaying the target in the lower central, right and left corners is shown at step 654.

Measurement and recording of eye movement and/or eye position and/or eye orientation changes occurs 642 after each of steps 650, 652, and 654. These measured and recorded eye movement and/or eye position and/or eye orientation changes are then processed to calibrate nine (9) separate points for ocular performance, at step 680.

Figure 12:
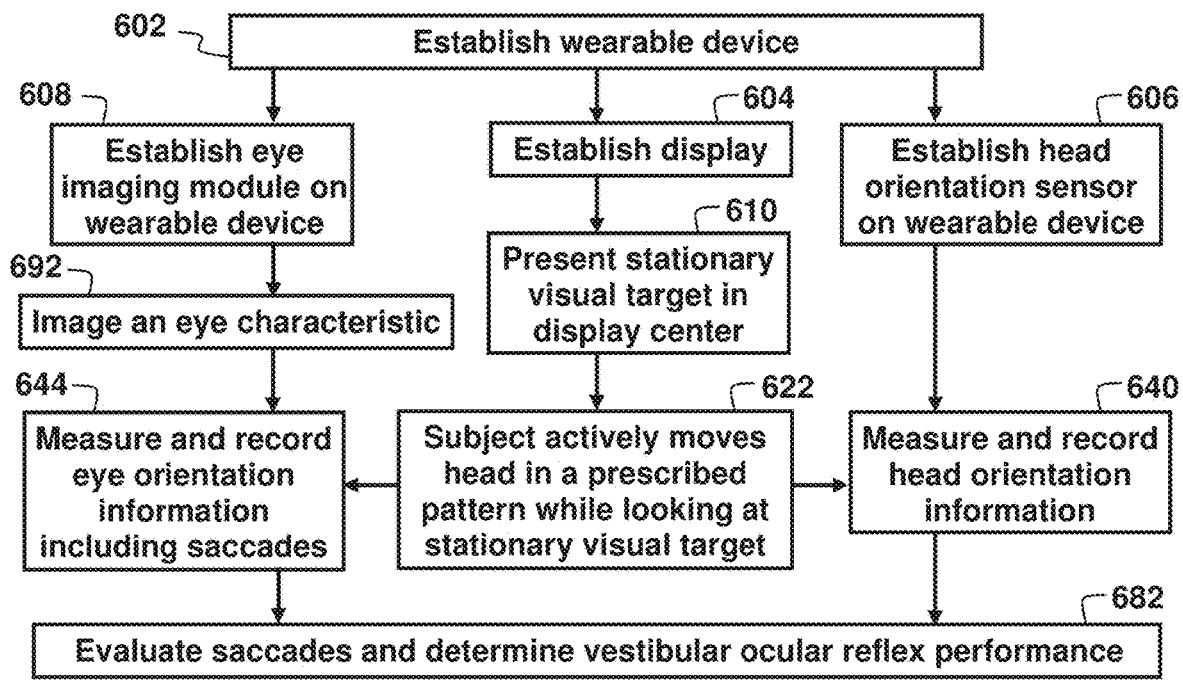
FIG. 12 shows a method for evaluating saccades and determining vestibulo-ocular reflex.

FIG. 12 shows an example of a vestibular ocular reflex test that also evaluates saccades. This test comprises the following configuration and steps:

This test uses a wearable device 602 that comprises a display 604, a head orientation sensor 606, and an eye imaging module 608, which images an eye characteristic 692.

Display: In this test, the display is static—neither the background nor the visual target of interest moves or changes in any way. The display comprises a subdued background and a centered white circular dot or other visually enhanced visual target, as shown at step 610.

Head: In this test, the subject is asked to actively move his/her head, in a prescribed pattern at varied velocities, each time he/she is given a cue signal, as shown at step 622. Each semicircular canal can be separately evaluated for vestibular ocular reflex by having the subject rotate the head in a specific prescribed pattern.

Eyes: The subject is instructed to keep his/her eyes focused on the stationary visual target as the head is moved in a prescribed pattern by the subject. The eye imaging module measures eye movement, in the opposite direction as the head movement, at step 644. This eye movement measurement in step 644 includes the measurement of overt and covert saccades.

Cues are provided to tell the subject when to move the head. These cues can be audio cues. The cues could be haptic (i.e., vibration on the side of the person's head). The cues could be visual (i.e., change of color or intensity of the visual target of interest). The cues are typically timed randomly so the subject doesn't try to anticipate the timing.

The test sequence is as follows:
1. A stationary visual target is established on the display, as shown at step 610.
2. The subject first moves the head slowly back and forth (typically sinusoidally) in the plane of the horizontal and vertical canals to be tested, while the subject fixates on the visual target for calibration, instructing the subject on the positions for testing and ensure that the head velocity and eye velocity are equal.
3. The subject actively moves the head in a prescribed pattern while looking at the stationary target, as shown at step 622. Examples of prescribed patterns, for assessment of each semicircular canal, can include.
   a. For horizontal canal testing, the subject should tilt the head downward typically 20-30 degrees, and with the head in this downward orientation, the subject should move the head typically 10-20 degrees left of center and 10-20 degrees right of center, alternating sides while continuously looking at the stationary visual target. This sequence can be repeated as many times as needed and at varying speeds.
   b. For testing of right vertical (anterior) canal, the subject should rotate the head left typically 45 degrees from center, and with the head in this leftward orientation, move the head downward typically 10-20 degrees and upward 10-20 degrees, alternating up and down, while continuously looking at the stationary visual target. This sequence can be repeated as many times as needed and at varying speeds.
   c. For testing of the left vertical (anterior) canal, the subject should rotate the head right typically 45 degrees from center, and with the head in this rightward orientation, move the head downward typically 10-20 degrees and upward 10-20 degrees, alternating up and down, while continuously looking at the stationary visual target. This sequence can be repeated as many times as needed and at varying speeds.
   d. For testing of the left posterior canal, the subject should rotate the head right typically 45 degrees from center, and with the head in this rightward orientation, the head is rotated typically backward 10-20 degrees and upward 10-20 degrees, alternating backward and upward, while continuously looking at the stationary visual target. This sequence can be repeated as many times as needed and at varying speeds.
   e. For testing of the right posterior canal, the subject should rotate the head left typically 45 degrees from center, and with the head in this leftward orientation, the head is rotated backward typically 10-20 degrees and upward 10-20 degrees, alternating backward and upward, while continuously looking at the stationary visual target. This sequence can be repeated as many times as needed and at varying speeds.
4. While step 622 is being performed by the subject, eye movement, and/or eye position and/or eye orientation changes, including overt and covert saccades are recorded, as shown at step 644.
5. Also, while step 622 is being performed by the subject, head orientation changes are being recorded, as shown at step 640
6. Responses from each eye and head orientation changes are compared and the vestibular ocular reflex performance is determined, as shown at step 682.

Processor: The processor in the system compares the head orientation changes from step 640 to the eye movement and/or eye position and/or eye orientation changes, of each eye, from step 644 to determine vestibulo-ocular reflex performance and to evaluate saccades, as shown at step 682. Performance can be measured as accuracy, gain (amplitude ratio of eye to head movement), phase (the timing response for the eye and head position), symmetry, eye, and head velocity, and/or saccade movement (overt and covert). Saccade movement can be measured as amplitude, accuracy, latency, and velocity.

Figure 13:
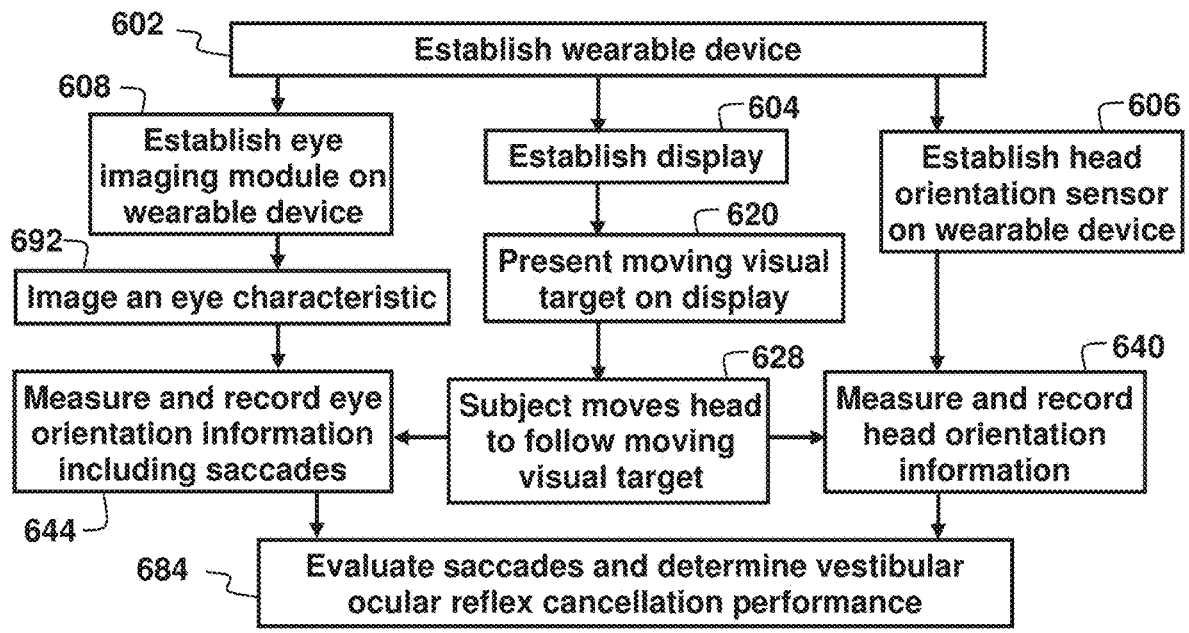
FIG. 13 shows a method for evaluating saccades and determining vestibulo-ocular reflex cancellation performance.

FIG. 13 shows an example of a vestibulo-ocular reflex cancellation test that also evaluates saccades. This test comprises the following configuration and steps:

This test uses a wearable device 602 that comprises a display 604, a head orientation sensor 606, and an eye imaging module 608, which images an eye characteristic 692.

Display: In this test, the visual target being displayed can be similar in appearance to the test described with reference to FIG. 11 and FIG. 12, but as shown at step 620 of FIG. 13, the visual target for vestibular reflex cancellation is moving (instead of static). The motion of the visual target can be horizontal, vertical, rotary, sinusoidal or a combination of any motion.

Head: In this test, the subject's head is moving with the visual target in the same direction. The intent is to maintain fixation of the eye while the visual target and head are both in motion (e.g., in the same direction and having the same speed), as shown at step 628. The head orientation sensor measures changes in head pitch, roll, and/or yaw 640.

Eyes: The subject is instructed to keep his/her eyes focused on the moving visual target as the head moves. The eye imaging module measures eye movement at step 644.

This eye movement measurement in step 644 includes the measurement of overt and covert saccades.

The test sequence is as follows:
1. The visual target initiates movement on the display in a selected pattern of motion, as shown at step 620.
2. The subject is instructed to move the head in the same direction as the visual target in order to follow the visual target at the same velocity and time, as shown at step 628.
3. The process can be repeated as needed, and at varying speeds.
4. This test can be conducted in the vertical, horizontal, rotary, sinusoidal or a combination of directions.

Processor: The processor compares the head orientation changes from step 640 to the eye movement and/or eye position and/or eye orientation changes, of each eye, from step 644, relative to the visual target motion, to determine vestibulo-ocular reflex cancellation performance and to evaluate saccades, as shown at step 684. Performance can be measured as accuracy of eye movement/position to target movement/position, gain (amplitude ratio of eye to head movement), phase (the timing response for the eye and head position relative to target motion), symmetry of both eyes following the moving target, eye and head velocity compared to target velocity, and/or saccade movement. Saccade movement can be measured as amplitude, accuracy, latency, and velocity.

FIG. 14 shows an example of a vergence test method. This test comprises the following configuration and steps:

This test can be performed using a wearable device 602 that comprises a display 604, and an eye imaging module 608, which images an eye characteristic 692. A head orientation device 606 (not shown) can also be established on the wearable device for calibration of the ocular performance, to measure any head orientation changes, and to be sure the head remains motionless during assessment of vergence.

Display: Like the test described with reference to FIG. 13, the vergence test method shown in FIG. 14 uses a moving visual target, as shown at step 620. The visual target appears to have motion toward and away from the subject's eyes. The visual target can move in either direction as a continuous transition, or it can occur in a series of distinct stages or steps.

Eyes: The subject is instructed to keep his/her eyes focused on the moving visual target. The eye imaging module measures eye movement and/or eye position and/or eye orientation changes at different depths and positions, as the visual target is moving toward and away from the subject's eyes at step 642.

Head: In this test, the subject is asked to keep his/her head motionless while looking at the visual target, as shown at 612. Note that, a head orientation sensor, as described herein, can be used to ensure that the head is, in fact, motionless during testing.

The test sequence without the use of a head orientation sensor is as follows;
1. The visual target moves on the display in a selected pattern of motion toward the user's eye, as shown at step 614.
2. The subject's eyes remain focused on the moving visual target as it appears to be moving toward the eyes, causing convergence of the eyes.
3. The eye imaging module measures eye movement and/or eye position and/or eye orientation changes, as the visual target is moving toward the subject's eyes at step 642.
4. The visual target initiates movement on the display in a selected pattern of motion away the user's eye, as shown at step 616.
5. The subject's eyes remain focused on the moving visual target as it appears to be moving away from the eyes, causing divergence of the eyes.
6. The eye imaging module measures eye movement and/or eye position and/or eye orientation changes, as the visual target is moving away at step 642.
7. The process can be repeated as needed, and at varying speeds.

Processor: The processor in the system compares the eye movement and/or eye position and/or eye orientation changes 642, from step 614, of each eye as the target moves towards the subject's eye and from step 616, as the visual target moves away from each of the eyes. Vergence performance 686 can be measured as eye movement and/or eye position and/or eye orientation changes including accuracy of convergence and divergence peak velocity, amplitude, symmetry, and latency.

Figure 15:
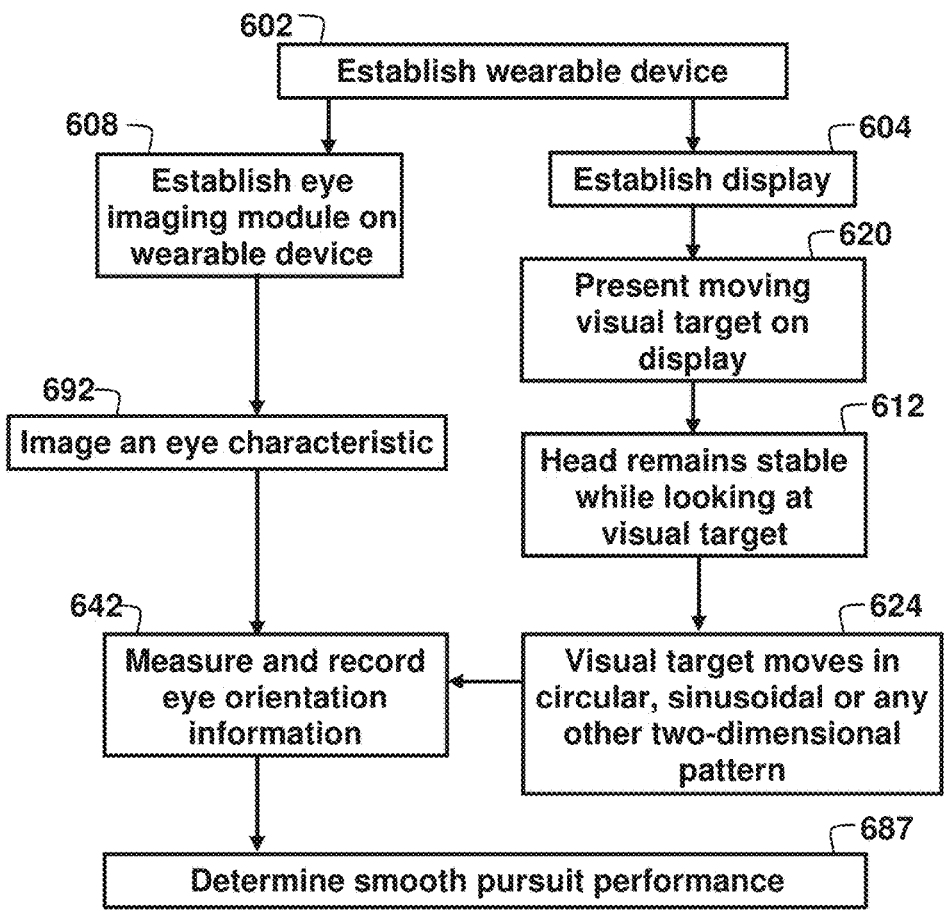
FIG. 15 shows a method for determining smooth pursuit performance.

FIG. 15 shows an example of a smooth pursuit test method. This test comprises the following configuration and steps:

This test uses a wearable device 602 that comprises a display 604, and an eye imaging module 608, which images an eye characteristic 692. A head orientation device 606 (not shown) can also be established on the wearable device for calibration of the ocular performance, to measure any head orientation changes, and to ensure the head remains motionless during smooth pursuit.

Display: Like the tests described with reference to FIG. 13 and FIG. 14, the smooth pursuit test method in FIG. 15 uses a moving visual target, as shown at step 620.

Head: In this test, the subject is asked to keep his/her head motionless while looking at the visual target, as shown at step 612. Note that, a head orientation sensor, as described herein, can be used to ensure that the head is motionless during testing.

Eyes: The subject is instructed to keep his/her eyes focused on the moving visual target. The eye imaging module measures eye movement and/or eye position and/or eye orientation changes 642, as the visual target is moving, at step 624.

The test sequence is as follows:
1. The visual target initiates movement on the display in a selected pattern of motion including horizontal, vertical, sinusoidal, rotary or any other pattern 624.
2. The subject is instructed to follow the moving visual target object with the eyes.
3. The process can be repeated as needed, and at varying speeds.

Processor: The processor in the system compares the eye movement and/or eye position and/or eye orientation changes including position of each eye, at step 642 to the visual target position at step 624, at a specific time, to determine smooth pursuit performance, as shown at step 687. Smooth pursuit performance can be determined by the measured eye movement and/or eye position and/or eye orientation changes including, but not limited to, gain (peak velocity/target velocity), velocity changes, accuracy of following a moving object and latency and comparing these measurements to the target movement.

Figure 16:
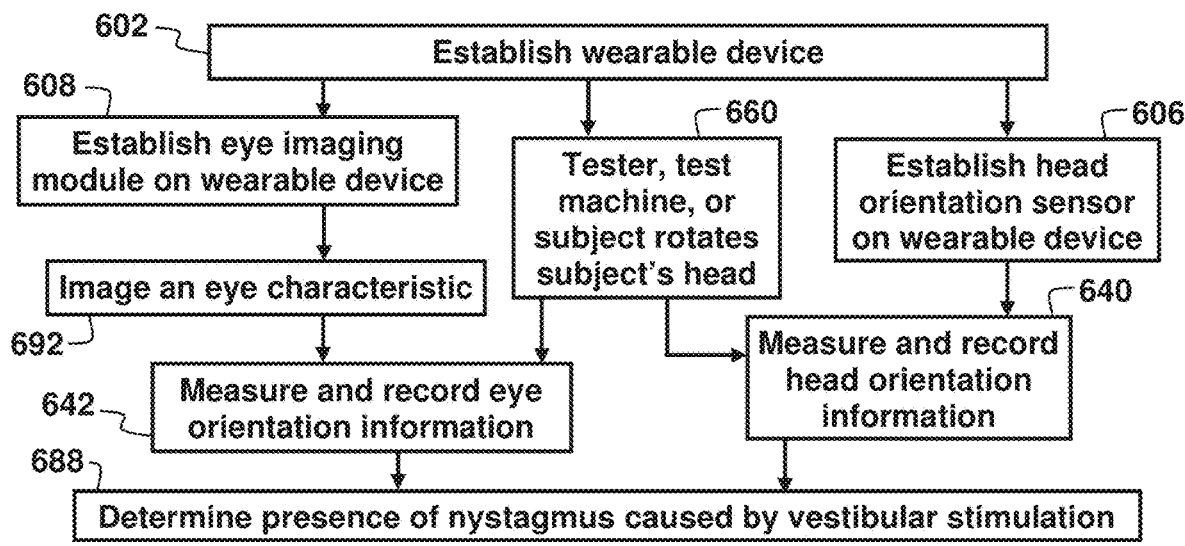
FIG. 16 shows a method for assessing nystagmus caused by vestibular stimulation.

FIG. 16 shows an example of a test method that uses vestibular stimulation to induce nystagmus. This test comprises the following configuration and steps: This test uses a wearable device 602 that comprises a head orientation sensor 606, and an eye imaging module 608, which images an eye characteristic 692.

Head: In this test, a tester, test machine, or the subject rotates the subject's head, as shown at step 660 to include positions which maximally stimulate the semicircular canals as described in FIG. 12 and FIG. 20. The head orientation sensor 606 measures changes in head pitch, roll, and/or yaw. Motion of the subject's head could be left and right. It could be up and down. It could be any other direction or set of directions capable of being understood by anyone skilled in the art. This test can be performed at any frequency and amplitude desired, but the most important range of frequencies is between 0.01 Hz and 20 Hz. This test is typically performed with a sinusoidal excitation of the head and maximum amplitudes must be kept low enough so that rotational accelerations do not create concussions. For this reason, rotational accelerations should be kept to less than 4,000 radians per second.

Eyes: The subject cannot focus on any specific visual target. The eye imaging module measures and records eye movement at step 642. Note that eye movement should be measured with an imaging device capable of operating at frequencies of 0.01 Hz to 20 Hz and rotational accelerations of up to 4,000 radians per second, to match the performance of the head rotations that were discussed previously.

The test sequence is as follows:
1. The subject's head is rotated as shown at step 660.
2. The eye movement is measured and recorded at step 642.
3. The head movement is measured and recorded at step 640. This must be measured in the same range of frequencies (between 0.01 Hz and 20 Hz) and amplitudes as the tester or test machine to rotate the subject's head.
4. The process can be repeated as needed, and at varying frequencies and amplitudes.
5. Testing can be vertical, diagonal, off-axis, or a combination of directions.
6. The eye and head orientation changes are measured and compared at step 688 to determine the presence of nystagmus caused by vestibular stimulation (specifically the vestibular labyrinth).
7. The process can be repeated as needed, and at varying rates and amplitudes.

Processor: The processor in the system compares the head orientation changes from step 640 to the eye movement and/or eye position and/or eye orientation changes, of each eye, from step 642 to determine the presence of nystagmus, as shown at step 688. The presence of nystagmus can be determined and measured by the slow-phase velocity (SPV), duration, binocularity, frequency, and amplitude.

Figure 17:
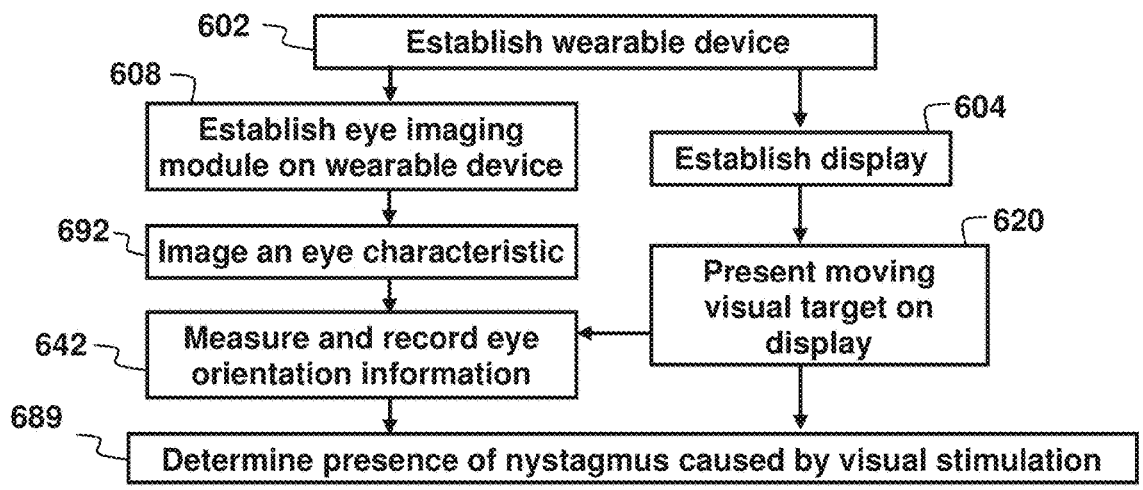
FIG. 17 shows a method for assessing nystagmus caused by visual stimulation.

FIG. 17 shows an example of a test method that assesses visual stimulation to induce nystagmus.

This test comprises the following configuration and steps:
This test uses a wearable device 602 that comprises a display 604, an eye imaging module 608, which images an eye characteristic 692, and a head orientation sensor 606 (not shown, but note that a head orientation sensor, as described herein, can be used to ensure that the head is motionless during testing).

Display: In this test, initially the display is subdued with no specific visual target. After the initial eye measures are recorded, a moving visual target (which could also represent a visual scene) is displayed in the center as shown in step 620.

Eyes: The subject initially cannot focus on any specific visual target. The eye imaging module measures and records eye movement at step 642. Once this initial measure is completed, the subject's eyes will view a moving visual target or visual scene to focus upon 620. This can be a rotary scene with multiple lines moving in a rotational pattern, or scene with undulating movements, like that viewed from riding in a roller coaster, or any other type of visually stimulating motion. The eye imaging module continues to record eye movements and is capable of operating at frequencies of 0.01 Hz to 20 Hz.

The test sequence is as follows:
1. The subject's head is motionless. This can be verified by measuring and recording head orientation changes, as shown in step 640 (not shown but as in FIG. 12, FIG. 13, FIG. 16).
2. A subdued background without a target is initially presented.
3. The eye movement and/or eye position and/or eye orientation changes are measured in the absence of a visual target as shown step 642. Spontaneous nystagmus is recorded.
4. A moving visual target or moving visual scene is then presented in the display, as shown in step 620, and the subject is instructed to visually fixate on the moving target or moving scene displayed.
5. The eye movement and/or eye position and/or eye orientation changes are again measured 642 to determine the presence of nystagmus caused by visual stimulation 689.

Processor: The processor in the system compares the eye movement and/or eye position and/or eye orientation changes of each eye 642, to determine the presence of nystagmus 689. The presence of nystagmus can be determined and measured by the slow-phase velocity (SPV), duration, symmetry of each eye movements or binocularity, frequency, and amplitude.

Figure 18:
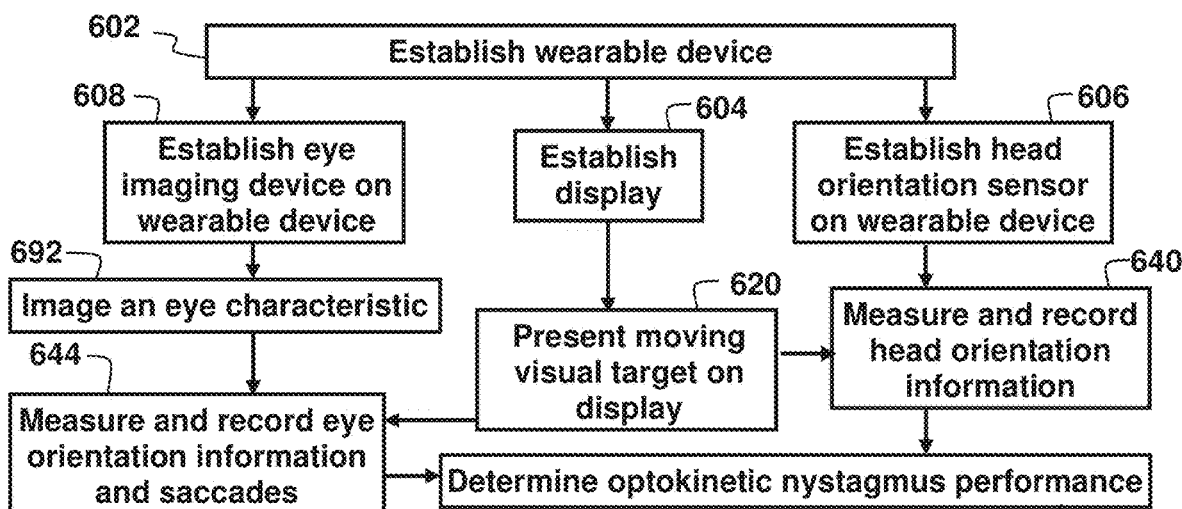
FIG. 18 shows a method for determining optokinetic nystagmus.

FIG. 18 shows an example of an optokinetic (OPK) test that is used to assess optokinetic reflex (OKR) or optokinetic nystagmus (OKN) performance. The optokinetic reflex (OKR) serves to stabilize a moving image on the retina. Optokinetic nystagmus is the eye movement elicited by the tracking of a moving field. It differs from smooth pursuit which is the eye movement elicited by tracking of a single distinct target. As moving fields contain within them distinct targets, OKN generally contains within it, smooth pursuit. Optokinetic nystagmus is the slow eye movement in the direction of a moving object with a rapid return of eye position in the opposite direction. This test comprises the following configuration and steps:

This test uses a wearable device 602 that comprises a display 604, and an eye imaging module 608, which images an eye characteristic 692. A head orientation device 606 (not shown) can also be established on the wearable unit for calibration of the ocular performance, to measure head orientation changes, and to ensure the head remains motionless during optokinetic testing.

Display: In this test, the moving visual target(s) 620 being displayed can be near the center of the display. The display seen is a succession of moving visual targets which can move vertically or horizontally.

Head: In this test, the subject's head is stable. The head orientation sensor 606 ensures that the head remains stable and can measure any pitch, roll, and/or yaw 640 changes.

Eyes: The subject is instructed to keep his/her eyes focused on the visual target(s) 620 as the target(s) scroll across the display screen. The eye movement measurement in step 644 measures eye movement and/or eye position and/or eye orientation changes including measurement of re-fixation saccades to determine the optokinetic nystagmus performance 678.

The test sequence is as follows:
1. The visual target initiates successive visual target movement on the display in vertical motion 620.
2. The subject is instructed to keep his/her head stationary, and eyes focused on the visual target(s) 620 as the target(s) scroll across the display screen.
3. While step 620 is being performed by the subject, eye movement and/or eye position and/or eye orientation changes, including re-fixation saccades are recorded, as shown at step 644.
4. Also, while step 640 is being performed, head orientation changes can be recorded, as shown at step 640.
5. Responses from each eye and head orientation changes are compared and the optokinetic nystagmus performance is determined with vertical motion of the target(s), as shown at step 678.
6. The testing is repeated with steps 1-5 but with the successive visual target movement on the display in horizontal motion 620.

Processor: The processor in the system compares the eye movement and/or eye position and/or eye orientation changes and saccades, of each eye from step 640, to determine optokinetic nystagmus performance, as shown at step 678. OKN can be seen with the slow phase in the same direction as the moving stimulus and interrupted by fast opposing saccade movement. Measurements can include slow phase velocity, amplitude, frequency, and duration as well as symmetry between the eyes or binocularity. Saccade movement can be measured as amplitude, latency, and velocity.

Figure 19:
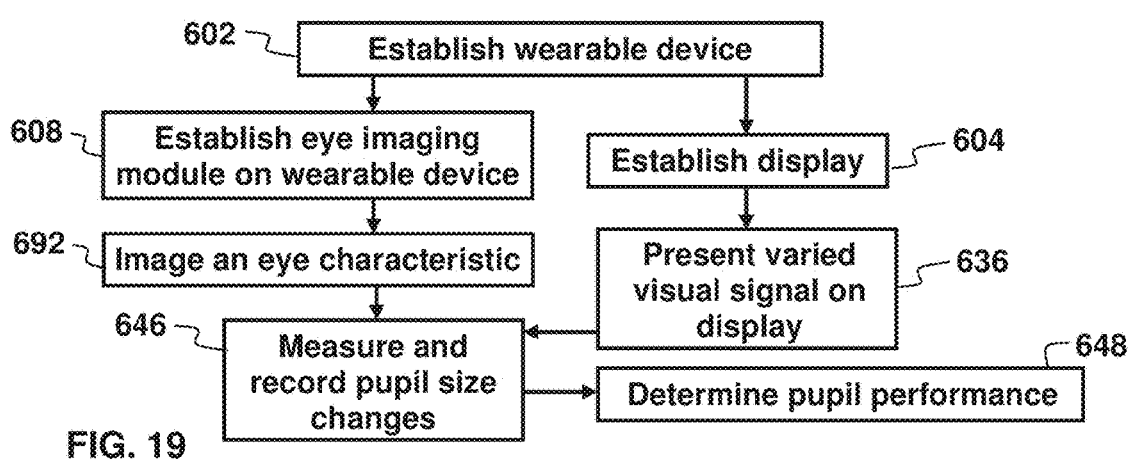
FIG. 19 shows a method for calibrating and determining pupil performance.

FIG. 19 shows an example of a method for determining pupil performance. This test comprises the following configuration and steps:

This test uses a wearable device 602 that comprises a display 604, and an eye imaging module 608, which images an eye characteristic 692. A head orientation device 606 (not shown) can also be established on the wearable device for calibration of the ocular performance, to measure any head orientation changes, and to be sure the head remains motionless during measurement and recording of pupil size.

Display: In this test, the behavior of the visual target on the display can vary, as shown at step 636. It could be stationary. It could vary in intensity. It could vary in size. It could have alternating bright and dim intensities of light with selective wavelengths, such as with chromatic pupillometry and/or with various stimulus presentations, causing the pupils to constrict and/or dilate. The visual target could have the motion described with reference to FIG. 14 with the visual target moving toward and away from the subject's eyes. The visual target could also appear in different positions have various shapes or other changes in features.

Eyes: The subject is instructed to keep his/her eyes focused on the visual target. The eye imaging module, at step 646 measures pupil size and features of pupillary changes.

Head: In this test, the subject is asked to keep his/her head motionless. Note again, a head orientation sensor, as described herein, can be used to ensure that the head is, in fact, motionless during testing.

The test sequence is as follows:
1. The subject's head is motionless.
2. Subject is instructed to view the visual target as it varies, as described previously with reference to the display and step 636.
3. The pupil size and activity changes are measured and recorded as shown at 646.
4. The process can be varied and repeated as needed.
5. Other methods of stimulus for changing pupil size can include light flashes or short-duration light stimuli, stepwise changes in irradiance or ramp-up light exposure and/or can include sound.

Processor: The processor can compare the pupil size at step 646 to determine the pupil performance at step 648. The pupil normally changes its size in response to distinct kinds of stimuli. It normally constricts in response to brightness (pupil light response) and near fixation (pupil near response) and it normally dilates in response to increased cognitive activity, such as increased levels of arousal or mental effort (psychosensory pupil response).

Figure 20:
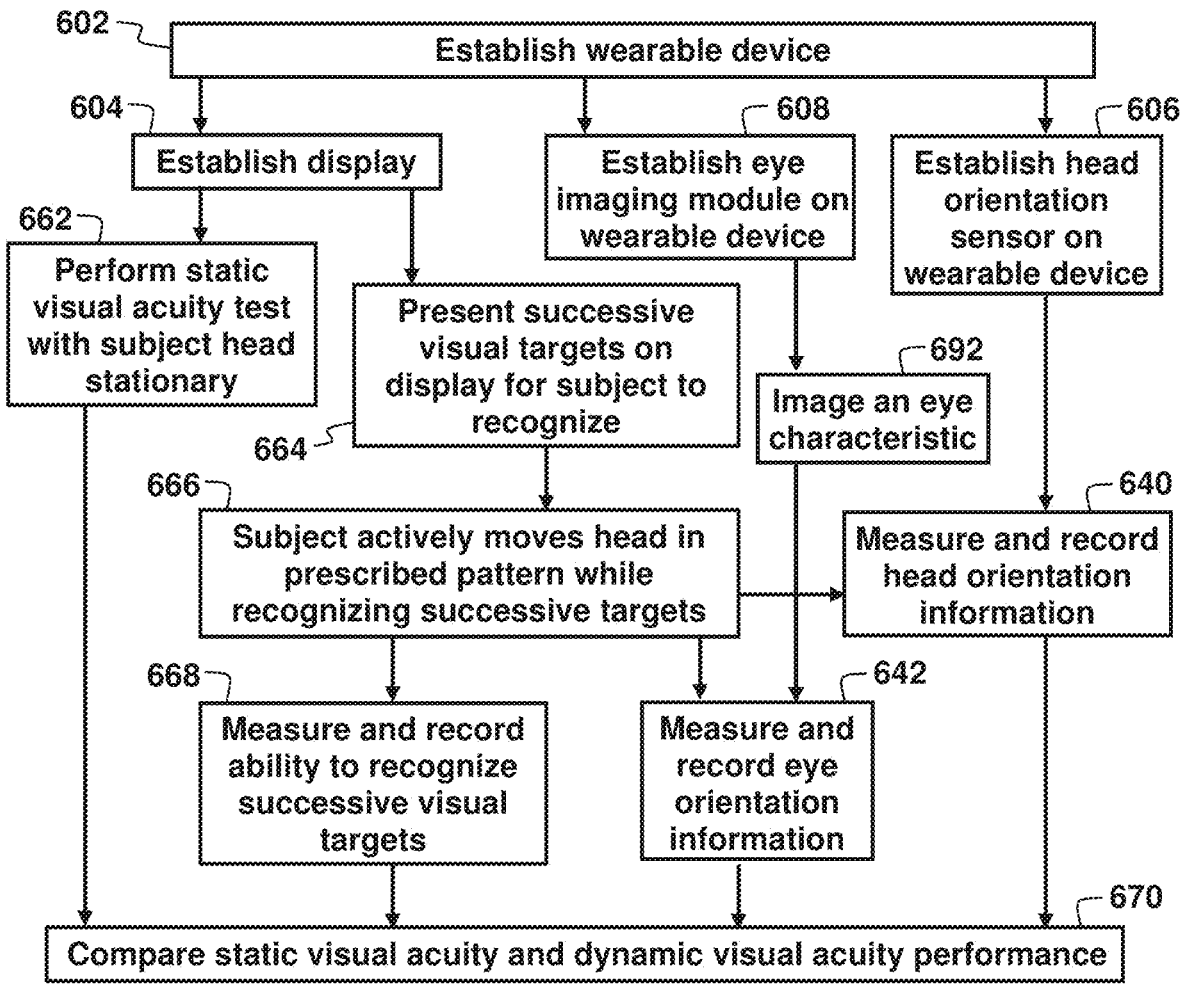
FIG. 20 shows a method for determining dynamic visual acuity performance.

FIG. 20 shows an example of a dynamic visual acuity (DVA) test method. This test comprises the following configuration and steps:

This test uses a wearable device 602 that comprises a display 604, a head orientation sensor 606, and an eye imaging module 608, which images an eye characteristic 692.

Display: In this test, the display can be comprised of a subdued background and a multitude of different images or optypes (letters, symbols, characters, figures of different sizes, shapes, orientation). The display can be used for both a classic static visual acuity test, shown at 662, or a dynamic visual acuity test, shown at 664.

Head: For static visual acuity performance measurement, the head is stationary. For dynamic visual acuity performance measurement, the subject actively moves his/her head in a prescribed pattern at varied velocities while stimulating the horizontal and/or vertical semicircular canals.

Eyes: The subject is instructed to keep his/her eyes focused on the visual target Cues are provided to tell the subject when to move the head with DVA testing. These cues can be audio cues. The cues could be haptic (i.e., vibration on the side of the person's head). The cues could be visual (i.e., change of color or intensity of the visual target of interest). The cues are typically timed randomly so the subject doesn't try to anticipate the timing.

The test sequence is as follows:
1. A routine vision test is first performed by presenting visual targets, similar to letters or elements seen on a Snellen chart, using the display, as shown at 662. This static test establishes a baseline visual acuity test in a static environment (e.g., static visual acuity or SVA). This static test does not necessarily need to be done with a Snellen chart, it could also be done by asking the subject to identify characters of various sizes, positions, and/or locations. The head doesn't move for this routine vision test.
2. The subject is then presented with successive visual targets (such as numbers, letters, or E's in different orientations) in the display center, as shown at step 664, that the subject must correctly identify, while moving the head in a prescribed pattern, as shown at step 666. The prescribed patterns can comprise the following, which have been determined to maximize excitation of the vestibular passages:
   a. The subject rotates the head down typically 20-30 degrees and while in this downward position, the subject moves the head right and left typically about 10-20 degrees from center, alternating to each side, while attempting to recognize the visual targets being displayed; and/or
   b. The subject rotates the head typically 45 degrees to the left of center, and while the head is rotated left of center, the subject moves the head downward typically near 10-20 degrees and upward 10-20 degrees, while attempting to recognize successive visual targets; and/or
   c. The subject rotates the head typically 45 degrees to the right of center, and while the head is rotated right of center, the subject moves the head downward typically 10-20 degrees and upward 10-20 degrees, while attempting to recognize successive visual targets.
3. The subject speaks out the character observed each time it changes, and this information is recorded, as shown at step 668.
4. The process described above that encompasses steps 664 and 666 can be repeated as many times as necessary, at different rotational speeds, with different optypes in the display, and with these optypes at different sizes.

Processor: The processor in the system compares the head orientation changes, shown at step 640, the eye movement and/or eye position and/or eye orientation changes as shown at 642, and the subject's ability to recognize the visual targets, as shown at step 668 to determine dynamic visual acuity. This dynamic visual acuity performance can then be compared to static visual acuity performance, as shown at step 670. It should be noted that such tests are ideally performed separately for each eye. Is should also be noted that vestibular ocular performance can also be determined, and saccades can also be detected, from the test method described in FIG. 20 by comparing head orientation changes from step 640 to eye movement and/or eye position and/or eye orientation changes from step 642.

Figure 21:
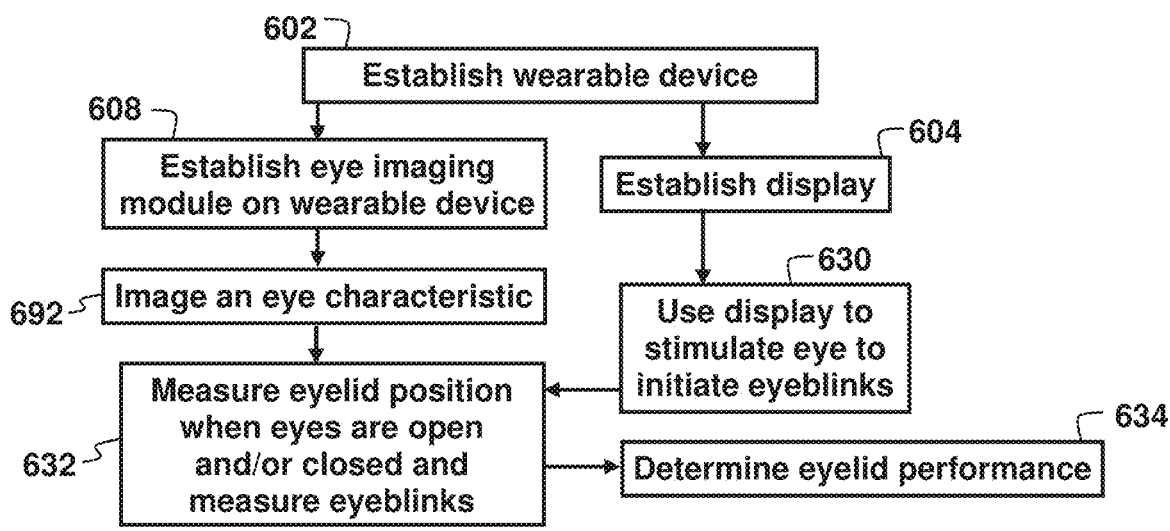
FIG. 21 shows a method for determining eyelid performance.

FIG. 21 shows an example of a method for determining eyelid performance. This test comprises the following configuration and steps:

This test uses a wearable device 602 that comprises a display 604 and an eye imaging module 608, which images an eye characteristic 692. A head orientation device 606 (not shown) can also be established on the wearable device for calibration of ocular performance, to measure any head orientation changes, and to ensure the head is motionless during the measurement of eyeblinks.

Display: In this test, the display is used to provoke eyeblinks.

Eyes: While the subject looks at the display, which stimulates the eye to initiate eyeblinks, as shown at step 630, the eye imaging module 608 measures eyelid position when the eyes are open and/or closed and measures eyeblinks, as shown at step 632.

The test sequence is as follows:
1. The subject is instructed to view the display, or a scene that will provoke eyeblinks, as shown at step 630.
2. The process is repeated as many times as needed, at various intensities of brightness, with varied task content and at varying speeds.
3. Eyelid position when the eyes are open and/or shut is measured and eyeblinks are measured, as shown at step 632.

Processor: The processor in the system uses the data from step 632 to determine eyelid performance, as shown at step 634.

Figure 37:
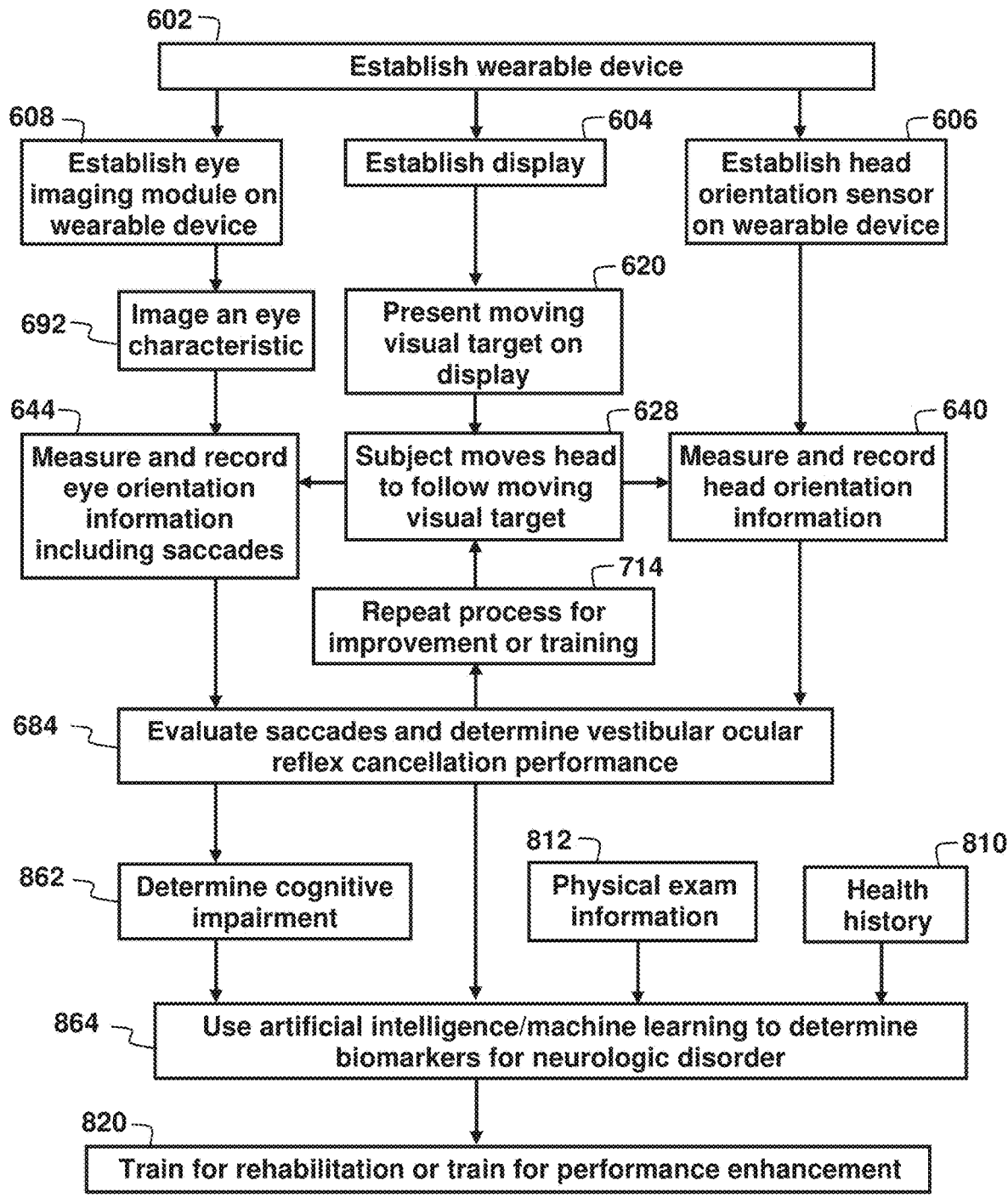
FIG. 37 shows a system for training and/or rehabilitation.
Figure 38:
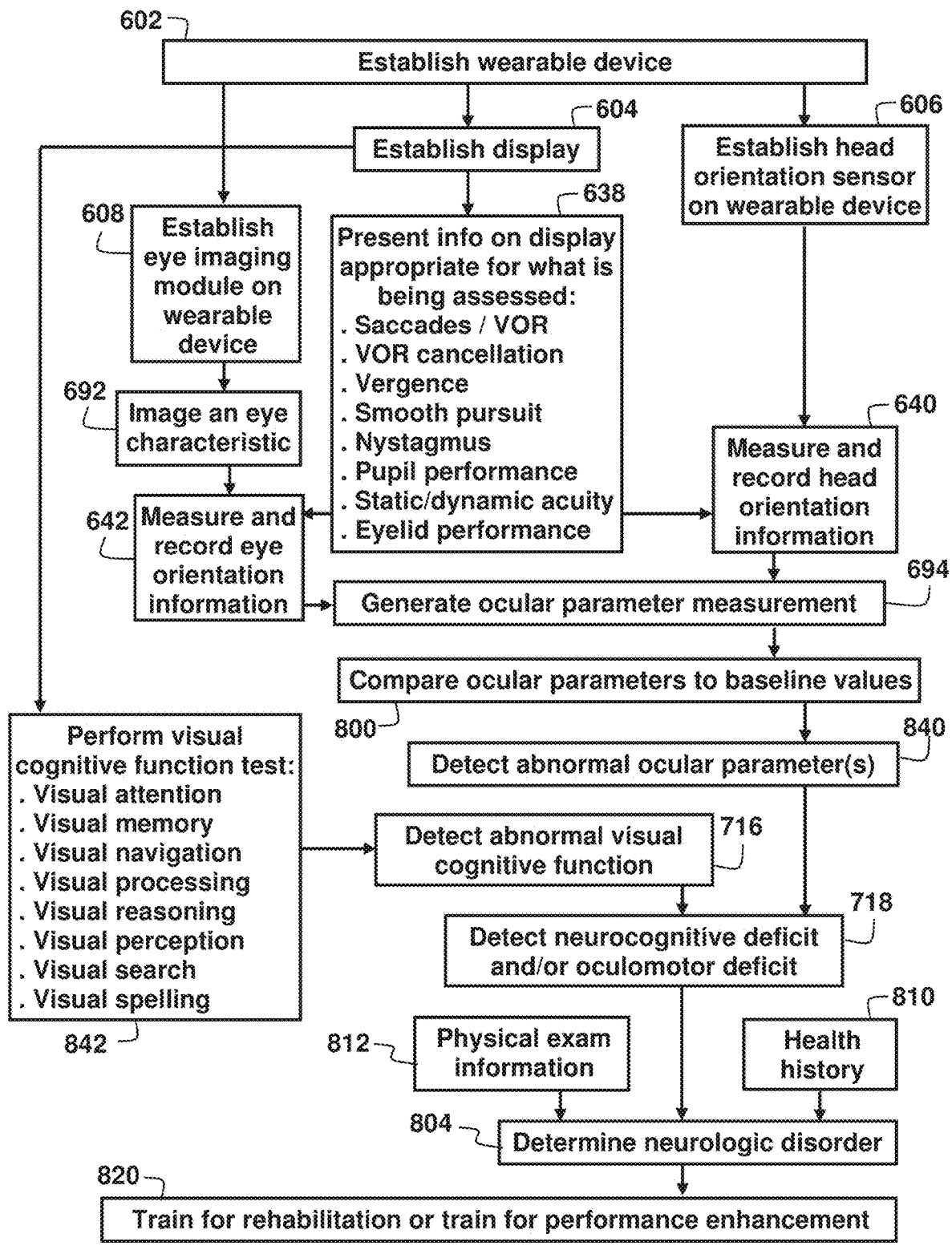
FIG. 38 is a system with cognitive function tests to detect neurologic disorders and for training and/or rehabilitation.
Figure 39:
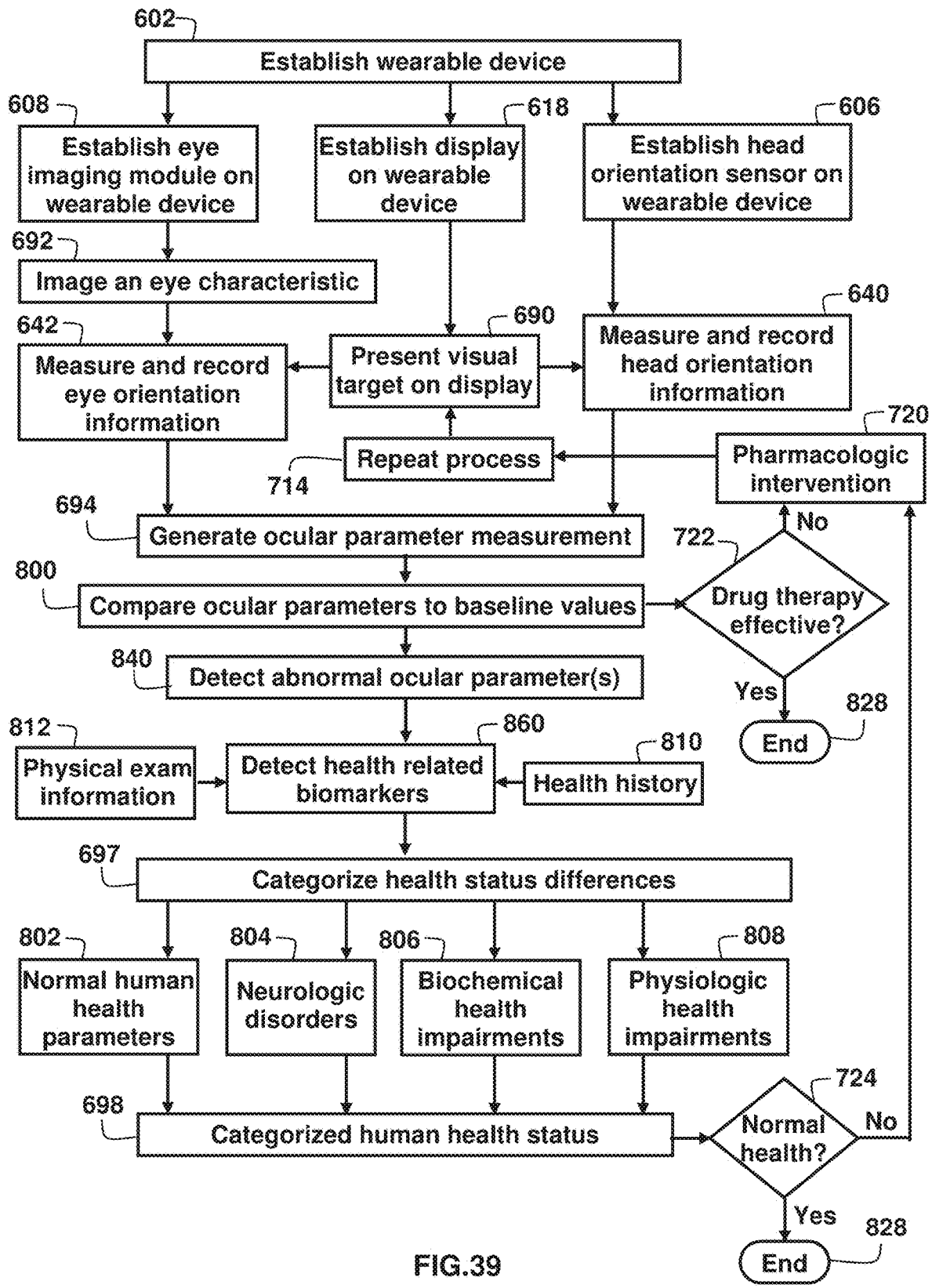
FIG. 39 shows a system for pharmacologic intervention.

There can be many additional embodiments of the ocular performance tests and other uses for the wearable platform (e.g., apparatus) described with reference to FIG. 1, FIG. 11, FIG. 12, FIG. 13, FIG. 14, FIG. 15, FIG. 16, FIG. 17, FIG. 18, FIG. 19, FIG. 20, FIG. 21, FIG. 32, FIG. 33, FIG. 34, FIG. 35, FIG. 36. FIG. 37, FIG. 38, and FIG. 39. The display and behavior of features on the display (i.e., functionality, form, and shape) can include combinations of the variations listed here:
   a. The visual target (an example of which would be a white dot or a visually enhanced object) can be any other shape, size, or coloring or have any other features capable of being understood by anyone skilled in the art. Examples of these variations in the visual target could include:
      A different shape (such as a shape comprising a cross hair);
      Different contrast, either more or less;
      Different intensity;
      Different size.
      Different focus, either more in-focus or out of focus;
      Having one or more features in the visual target that move relative to the rest of the visual target;

Different depths;

The appearance of a natural object (such as a baseball, a basketball, or a bird); and/or;

The appearance of a visual scene which can be stationary or in motion

Any combination of any of the above.

b. The test could be run with the visual target not being stationary. This would make the overall test more like a natural environment in which the head, the eyes, and the visual world are each moving relative to one another and relative to a stationary reference frame at all times. When implemented on a display in an augmented reality or virtual reality (i.e., an extended reality) environment, this would mean that the visual target could:

Move with the head movement;

Move contrary to the head movement;

Move perpendicular to head movement, and/or

Move in any random pattern not associated with head movement c. The background (traditionally subdued, plain, solid, and/or non-distracting) could be presented on the display of the system as any other background understood by anyone skilled in the art. Examples of variations of the background can include embodiments in which the background is more natural and like actual scene and/or any of the variations in the following list:

The background can be completely static;

The background can have moving and/or flashing elements;

The background can be enhanced with auditory distractions consistent with the imagery being displayed;

The background can be in or out of focus;

The background can be low intensity/contrast or high intensity/contrast relative to target of interest;

The object of interest or image can utilize foveated rendering, in which only the target of interest which the user is visualizing is seen clearly, where the fovea is focused, and the remainder of the adjacent region is less detailed.

d. Any of the embodiments of ocular parameter measurements used to determine or influence human health, as described in this document including the combinations of the variations described above, could also be performed without a head worn device.

e. Any of the embodiments of ocular parameter measurements used to determine or influence human health, as described in this document including the combinations of the variations described above, could also be performed without a visual display.

In the tests described with reference to FIG. 1, FIG. 11, FIG. 12, FIG. 13, FIG. 14, FIG. 15, and FIG. 16, FIG. 17, FIG. 18, FIG. 19, FIG. 20, and FIG. 21, a display can also be used for positional testing. For example, extended reality goggles can be configured to display a background that has illumination, but no definable image that might provide orientation information to the subject. The subject, could then be asked to turn the head left, right, lie supine, while supine head turns right, head turns left, then turn the body (roll) right and turn the body (roll) left. During each positional change, the eyes are tracked using the extended reality system to look for abnormal eye movements. If a visual target was visible during this testing the nystagmus would be suppressed. However, targets with poor contrast can be displayed to provide a more immersive test environment. Visual targets in this instance should not have defining characteristics that might enable eye fixation.

Figure 22A:
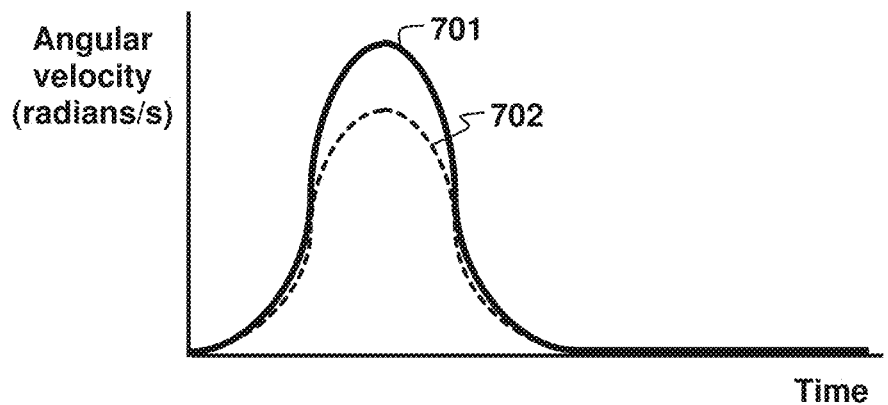
FIG. 22A shows a vestibulo-ocular gain measurement.
Figure 22B:
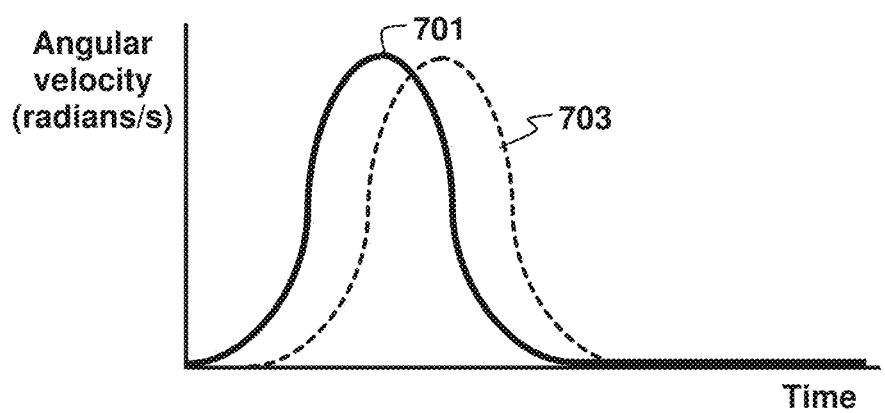
FIG. 22B shows a vestibulo-ocular phase measurement.
Figure 22C:
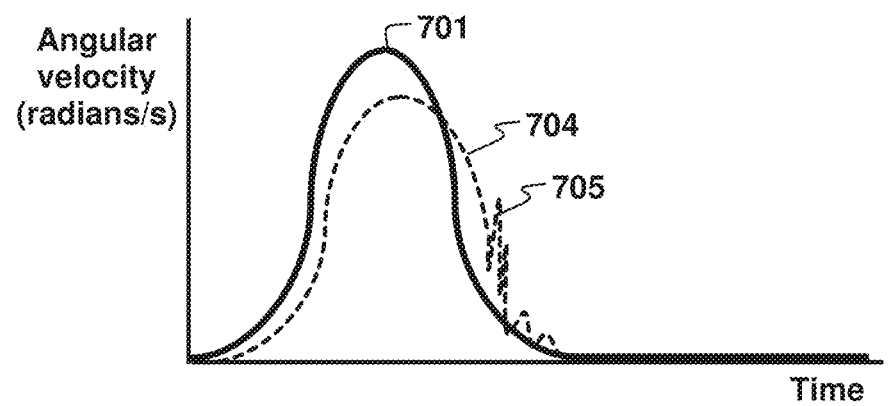
FIG. 22C shows overt ocular saccades.

FIG. 22A, FIG. 22B, and FIG. 22C provide graphs of time versus angular velocity that show how an eye movement response to a vestibular input can be measured. In these figures, the input is a rotation of the head, which is shown as the solid line at 701. This head rotation information would typically be measured using the head orientation sensor 404, that has been shown in FIG. 2, FIG. 3, FIG. 4B, FIG. 5, FIG. 6A, and FIG. 7B. The output is the eye movement response to the head rotation, which is shown as the dotted line at 702, 703, and 704, and would typically be measured using the eye sensor, which is typically an eye imaging device 406, such as that shown in FIG. 2, FIG. 3, FIG. 4B, and FIG. 5. The actual eye movement response is in the direction opposite of the head rotation. 701, but it has been plotted in the same direction to make it easier to compare the input and output of a person's vestibulo-ocular system. In 21A, the velocity of the eyes is slower than that of the head, which results in a gain of less than 1.0 (i.e., a loss of amplitude 702). In FIG. 22B there is a delay between the rotation of the head and the rotation of the eyes, which results in a phase lag, 703. In FIG. 22C, the eye rotation also lags the head rotation as shown at 704 but is caught up by overt saccades 705 near the end of the rotation.

Figure 23A:
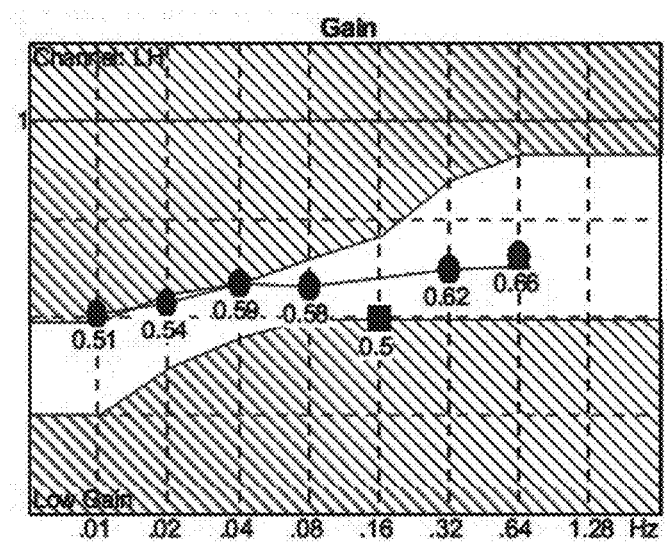
FIG. 23A is left eye gain for healthy vestibulo-ocular response to 0.1-1.28 Hz motion.
Figure 23B:
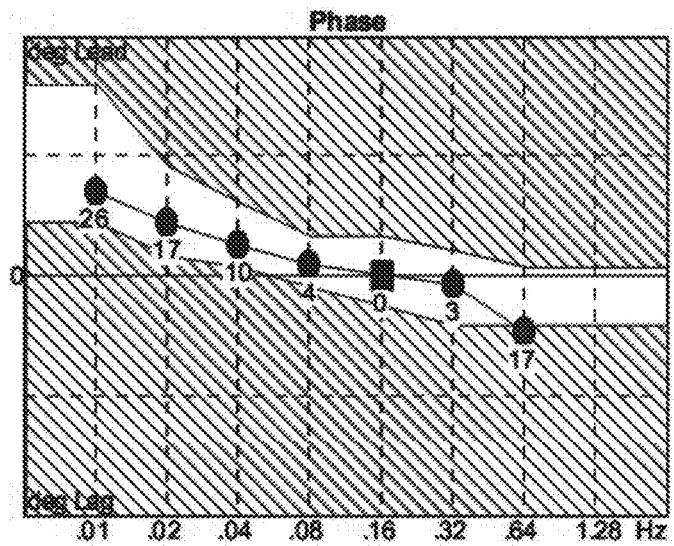
FIG. 23B shows healthy response phase lead and lag for 0.1-1.28 Hz motion.
Figure 23C:
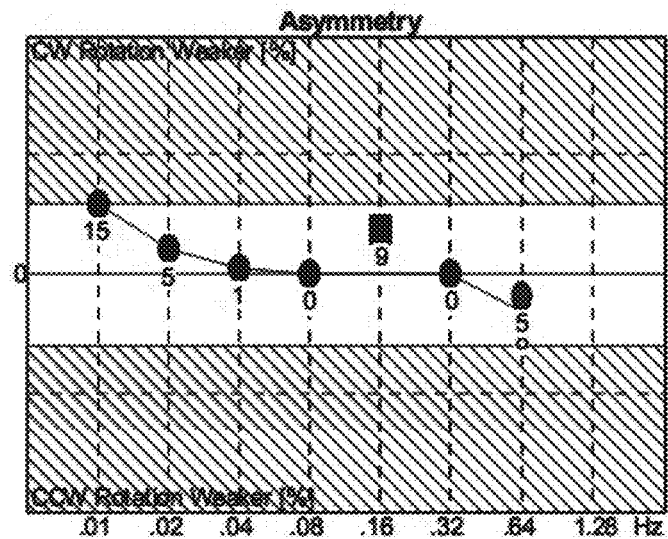
FIG. 23C illustrates an example of the readings between counterclockwise and clockwise horizontal rotation of a healthy person's vestibulo-ocular response to head motion.

The measures shown in FIG. 22A, FIG. 22B, and FIG. 22C, can be processed through a Fourier transform, plotted at different frequencies, and compared between the head movements and the left eye and the right eye movements to create the plots shown in FIG. 23A, FIG. 23B, and FIG. 23C, which illustrate some typical eye responses to oscillation of a healthy person's head (e.g. vestibulo-ocular responses) in a horizontal plane at frequencies ranging from 0.1 Hertz (1 cycle every 10 seconds) to 1.28 Hertz (approximately 5 cycles every 4 seconds). More specifically, FIG. 23A shows the gain at these frequencies, FIG. 23B shows the phase lead or lag at these frequencies, and FIG. 23C shows the relative symmetry (or asymmetry) between clockwise and counterclockwise oscillations. It should be noted that 0.1 Hertz to 1.28 Hertz is typical for the range of frequencies being used by prior art VOR rotary testing systems. The embodiments described in this disclosure can include any frequency in the range of 0.01 Hertz (1 cycle every 100 seconds) to 20 Hertz (approximately cycles every second). It can be understood that such a Fourier transform, or any type of Fourier analysis could be used with any of the embodiments described herein.

FIG. 24A, FIG. 24B, FIG. 25, FIG. 26, FIG. 27, and FIG. 28 relate to visual targets that could be presented without the use of extended reality (virtual reality or augmented reality) displays or presented on an extended reality (XR) display to facilitate measurement and/or improve ocular performance parameters such as vestibulo-ocular reflex function, smooth pursuit, saccades, vergence, DVA, or other ocular parameters discussed herein to determine human health. These visual targets can be designed to enhance the eye fixation on the displayed image when the head is motionless, and the visual target is in motion. These visual targets could also be designed for when the head is in motion and the visual target is motionless or when both the head and the visual target are in motion, such as with vestibulo-ocular reflex cancellation (VORC). In embodiments of the invention, presentation of visual targets without the use of XR displays, such as with a projected image and/or using natural elements in a scene, or when using XR display systems, the displayed visual targets can be static in a position or location or the displayed visual targets can be dynamically changing in position and appearance, depending on the specific test being performed or rehabilitation method being used. The visual targets, upon which the eyes are attempting to focus, can be of a variety of colors, sizes, shapes, and forms. They can change in color, size, shape, and form. They can contrast with other items being displayed to be dominant in order to provide visual weight to enable fixation. These visual targets can use specific colors with more saturation and can change in scale and proportion, all to draw the fovea toward a specific point of fixation on the visual target. With stereoscopic or 3-dimensional viewing, foveated rendering can also allow the image of interest to be seen in detail more clearly and the remaining adjacent region to be less detailed. Without using such enhancements to the target displayed, the eyes tend to wander and have more microsaccades, which decrease fixation ability, attentiveness, and ocular parameter testing accuracy. Generally, it is important to have some small point of focus on the visual target to lessen the microsaccades and enhance the fixation ability. These same visual targets can be used for any oculomotor or ocular performance testing including VOR re-training when a VOR abnormality exists. Each one of the ocular parameters discussed above can be used separately or in combination with others to detect neurologic disorders, such as concussions (traumatic brain injuries) or cognitive deficits, physiologic impairments, such as fatigue or alertness, and/or biochemical impairments such as impairments due to alcohol or drugs. Additionally, they can be used for training in order improve the health status. These eye measures with the use of artificial intelligence and machine learning can predict human disorders and detect health-related biomarkers to diagnose neurocognitive diseases.

The ideas expressed in the previous paragraph can best be explained by looking at some examples. FIG. 24A shows an example of a visual target in the form of a soccer ball 902. This soccer ball could be part of an existing scene viewed on a display, or the soccer ball could have been added to the scene. The soccer ball could be spinning, which might make the pattern on the ball distracting. FIG. 24B shows the visual target (soccer ball) of FIG. 24A that has been altered by defocusing the ball 904 and superimposing a target in the form of a crosshair 906, that is more precise for the eyes to focus on. Focusing on the center of the crosshair target shown in FIG. 24B can provide enhanced fixation accuracy compared to viewing the target shown in FIG. 24A due to the shape, size, contrast, and suppression of the pattern on the ball. Although this example has been done using a black and white image, color and color contrast can be more effective. For example, the visual target seen in the display could be a red colored ball and within the center of the ball or a dark crosshair surrounded by a lighter yellow circle could be placed. This strongly contrasted central focal point can help the eye focus on a specific point and lessen the "eye scanning" while undergoing any ocular performance measurement such as VOR testing or VOR re-training. In another example, the target being viewed can be in the shape of a familiar object, such as a basketball, football, helmet, or object used in one's occupation. It can also have a centered focal point, created by high contrast and high color saturation compared to the surrounding background to maintain foveal fixation duration, attentiveness, and lessen microsaccades.

FIG. 25 shows a scene that can be used for optokinetic testing in a virtual or augmented environment. In traditional optokinetic testing, a person's head is motionless while seated inside a moving drum with alternating black and white vertical lines or alternatively, a hand-held drum, with alternating black and white vertical lines, is placed in front of the person. The drum is slowly rotated. The alternating lines induce nystagmus and cause visually induced motion sickness. The movement of the eyes is measured as the drum rotates left and then right. Measurements can be at different drum speeds. This same test can be performed by creating a visual image on a display that includes targets that work just like the vertical lines in the drum. Examples of natural scenes that are like the drum with lines can include examples such as being seated in a car and watching a train go by or driving and watching the telephone poles move by, such as the scene 910 shown in FIG. 25. Similarly, flying objects can be visualized as moving across the visual field or along another plane of motion beside the person. These visual targets can also change in size, color, or other dimensions, as the person gets closer to the virtual object or further from the visual target. Motion can occur in any direction or depth relative to the person, as the eye movement is being assessed and measured.

Figure 26:
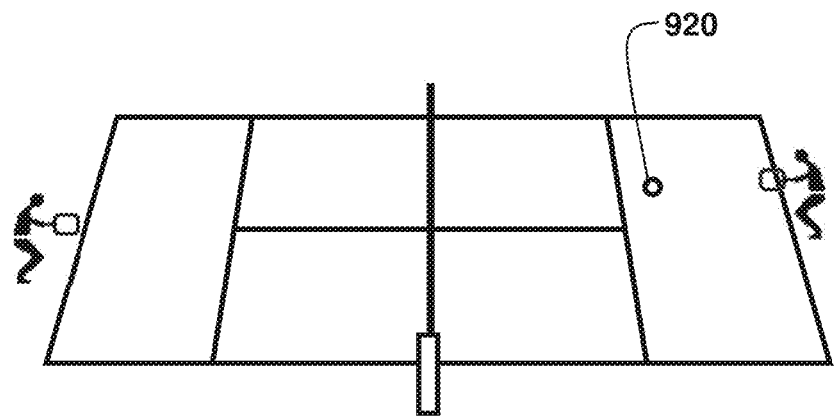
FIG. 26 shows a scene for testing vestibulo-ocular reflex cancellation performance.
Figure 27:
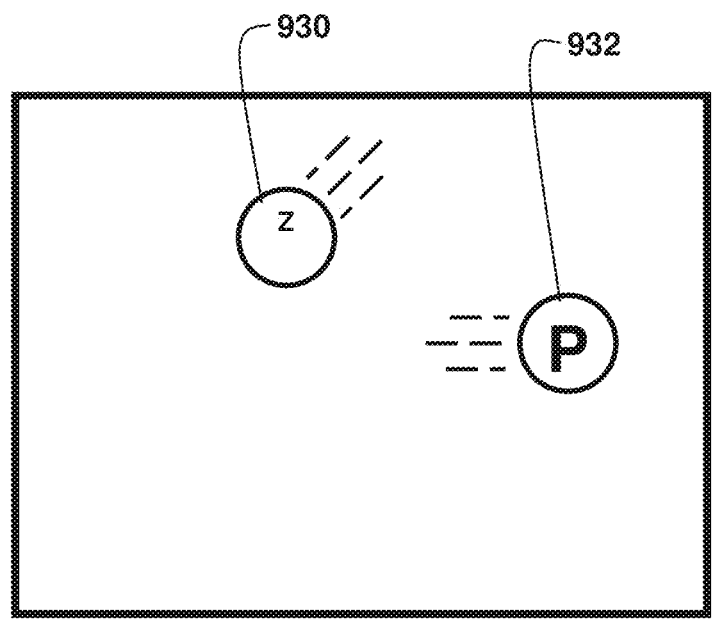
FIG. 27 shows a scene that can be used for dynamic visual acuity testing.
Figure 28:
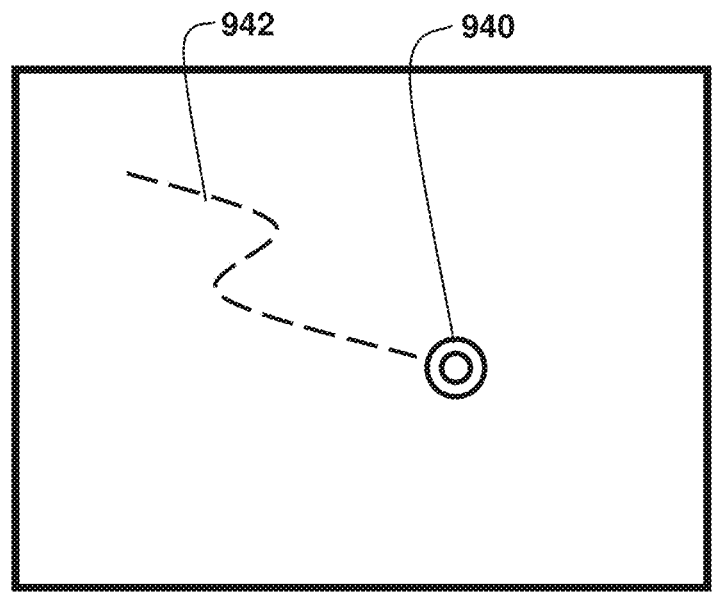
FIG. 28 shows a scene that can be used for scan path tracking.

FIG. 26, FIG. 27, and FIG. 28 illustrate other display scenes that can be used for ocular performance testing such as saccades, vestibulo-ocular reflex (VOR), dynamic visual acuity (DVA), smooth pursuit, vestibulo-ocular reflex cancellation (VORC), vergence, and/or fixation ability testing. These scenes can include a test environment comprising natural background features combined with a visual target whose shape, color, size, motion, depth, or other attributes have been selected or added to facilitate testing of ocular parameters. FIG. 26 shows an example of a scene which illustrates what this type of ocular performance testing, such as with smooth pursuit, VORC, DVA and/or VOR might look like. In the example shown in FIG. 26, the static scene can be a tennis court and the moving target is the tennis ball 920. The visual target (e.g., tennis ball) can remain motionless in the center, surrounded by a static court with 2 players on each side. The individual being tested would rotate his/her head in the horizontal plane while focusing on the visual target. For another alternative measure, the individual can be rotating the head in the same direction as the ball in motion for assessment of vestibulo-ocular reflex cancellation. For more complex testing, the surrounding background can be filled with fans who are also in motion. Smooth pursuit can also be virtually measured using the basketball as the visual target as it moves from player to player or being thrown upwards to the basketball hoop. This can be a more realistic method of assessing ocular performance with smooth pursuit measurement when the head is motionless or with VORC, when the head is in motion in the same direction as the viewed visual target. DVA measurement can also be performed with dynamic changes of the visual target of interest, requiring the person to identify characteristics of the target while it is in motion and the head is motionless, then comparing this to the static visual acuity (SVA) prior to the onset of the DVA test. FIG. 27 shows letters that could be superimposed onto the moving target (such as the tennis ball in FIG. 26) to test DVA. The visual target 920 in FIGS. 26, 930 and 932 in FIG. 26, or 940 in FIG. 28 could move in different trajectories, in different depths, the letters could be of different sizes, and the ball could move at different speeds and accelerations to provide a meaningful test as shown by comparing visual target 930 with visual target 932. The targets can be static or rapidly moving is a specific plane or scan path for (such as watching a tennis ball move across the court or with tracking tests that have a rotating visual target) depending on the ocular parameter being tested. In one example, vergence tracking and measurements can be performed with the visual target or stimulus moving in any known direction or pattern, such as horizontally, vertically, in a circular path, in a sinusoidal pattern, in a trapezoidal pattern, and/or at different velocities and/or combination of motion. The measures can be performed with the head in a static position or with the head in motion and moving in the same direction as the visual target.

DVA testing could be performed with lettered optotypes and as the head rotates back and forth, the letters can rotate in position. Alternatively, numbers can be used as well as other familiar images of objects. The images can also be native or natural to the background environment displayed. As the head rotates back and forth, the visual target is more difficult to visualize. If there is a VOR abnormality, for example the eyes will not be able to focus on the visual target of interest and will subsequently have less fixation and more errors in identifying a visual target. Measurement can also be performed with the visual target stationary and the head in motion or both the visual target and head in motion, which would be more realistic with everyday experiences. Static visual testing (SVT) can be performed to obtain a normal visual test. The visual acuity can be obtained, while the head and the visual target, or optotype being displayed are both motionless. Like a standard eye exam, an XR platform can enable a person's static visual acuity (SVA), a component of DVA testing, by asking a person to identify a multitude of images or optotypes (letters, symbols, characters, figures of different sizes, shapes, orientation) on the visual screen.

Dynamic visual acuity (DVA), and foveal visual stability (FVS) testing can be used to determine a person's vestibulo-ocular reflex performance. Normally, DVA assessment includes identifying a series of static images or optotypes but with the addition of head movement. The displayed images could also be dynamically moving in any direction and can be random in position, appearance, and presentation. Specifically, the image or visual target to be identified can be moving in any direction, randomly or with a specified pattern of motion, and may have different shapes, features, colors, sizes, orientation, patterns, or identifying characteristics, in a specific plane of axis or in variable plane, which the person must identify while the head in motion or rotating. The subject can then provide feedback regarding what they see via an on-screen gesture, keyboard, smart device (e.g., defined as an electronic device, generally connected to other devices or networks via different wireless protocols such as Bluetooth, NFC, Wi-Fi, 3G/4G/5G cellular, etc., that can operate to some extent interactively and autonomously), eye or other physical response or by voice response. The comparison of the smallest visual image or optotypes in both the DVA and SVA tests can determine if the person has a defect in his or her vestibulo-ocular reflex performance. DVA assessment can also be performed as described in FIG. 26, FIG. 27, and FIG. 28 without a display, using only visualized natural elements in the visible scene.

Smooth pursuit testing can be performed with similar visual targets of interest as described previously. Smooth pursuit testing has traditionally been performed with the head motionless and the eyes following a moving light or finger moving across a visual field. FIG. 28 shows a scene for scan path tracking in a virtual or augmented environment. An enhanced visual target 940, can be sent across the scene along a specific path 942, while the measured eye movement follows the visual target. The path of these visual images or targets can assume any pattern, such as a zigzag, a saw toothed, or a square wave, or have a scan path that is snake-like, curved, circular, sinusoidal, or rotational to provide a realistic and natural method of assessment of smooth pursuit. This can also be performed with the head in motion, following the visual target (e.g., vestibulo-ocular reflex cancellation).

Figure 29:
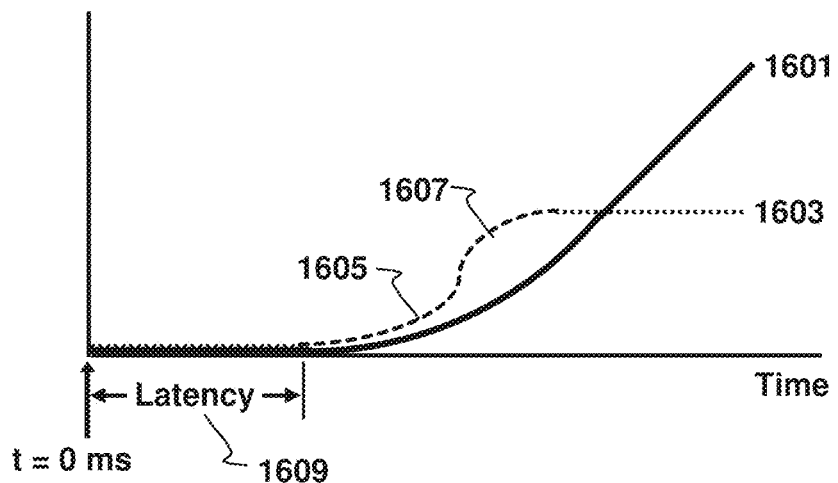
FIG. 29 shows target movement and eye position, velocity, and acceleration for smooth pursuit.

FIG. 29 shows the relationship between target movement, eye position 1601, eye velocity 1603, and eye acceleration for smooth pursuit. The time when the target is moved is identified as t=0 ms. The eye position 1601, and eye velocity 1603, can then be tracked as a function of time. Latency 1609, is the delay from the time the target moves to the time the eye starts to move. Then the eye velocity 1603, will first accelerate 1605, and decelerate 1607, until the eye velocity 1603, matches the target velocity.

Figure 30A:
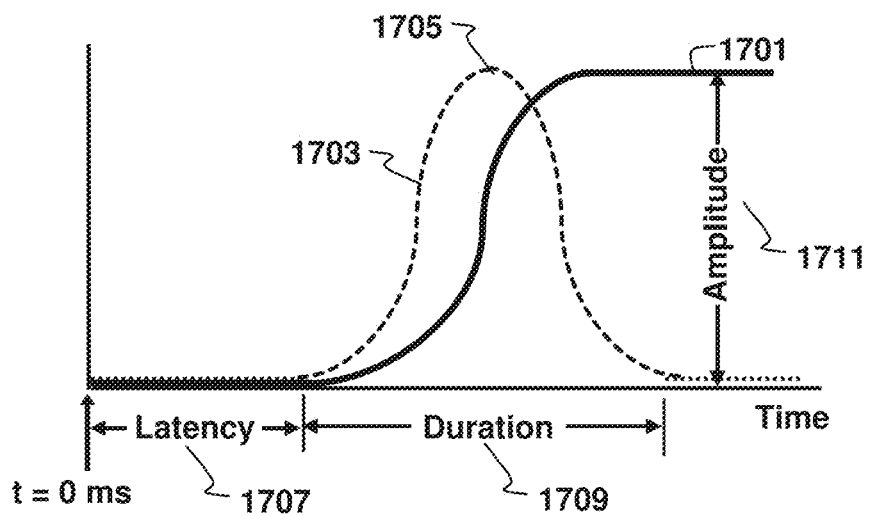
FIG. 30A shows target movement, eye position, and eye velocity for a saccade.
Figure 30B:
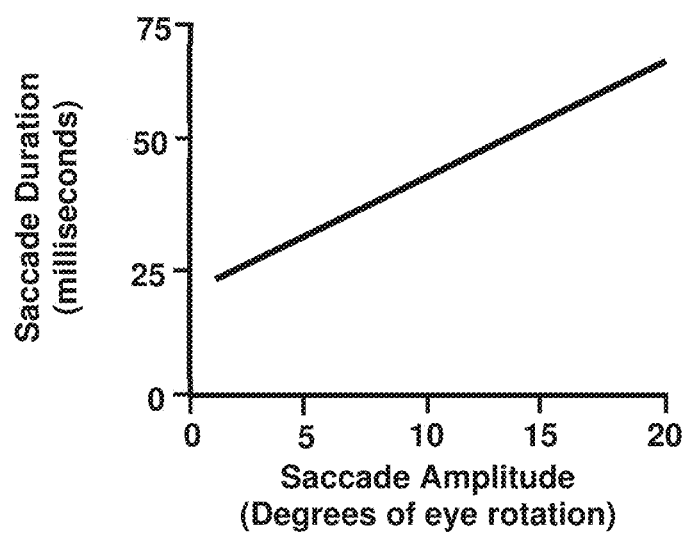
FIG. 30B shows a typical relationship between saccade amplitude and saccade duration.

FIG. 30A shows the relationship between target movement, eye position 1701, and eye velocity 1703, for a saccade. The time when the target is moved is identified as t=oms. The eye position 1701, and eye velocity 1703, can then be tracked as a function of time. Latency 1707 is the delay from the time the target moves to the time the onset of a saccade. As shown, the saccade eye velocity 1703, increases, reaches a peak velocity 1705, and then returns to zero. The length of time from the start to the end of this velocity curve is called the saccade duration 1709. The saccade eye position 1701, changes during this duration 1709 to reach a new position that differs from the initial eye position by a distance that can be defined as a saccade amplitude 1711. FIG. 30B shows the typical relationship between saccade amplitude and saccade duration.

Note that any of the ocular parameter measurements described herein for any of these embodiments can be done with static targets or visual targets being viewed, or with dynamic targets. They can include more complex combinations of different ocular parameters. For example, vergence can be simultaneously measured with VORC and pupil size as the eyes and head are following a visual target moving as it transitions different depths with varying luminosities and when the target simultaneously moves in different directions or patterns as it nears or moves away from the eyes. The images or targets viewed may be familiar objects, such as balls, or objects more familiar to one's occupation. The visual target may be displayed in a manner that is native or natural to the background.

Figure 31A:
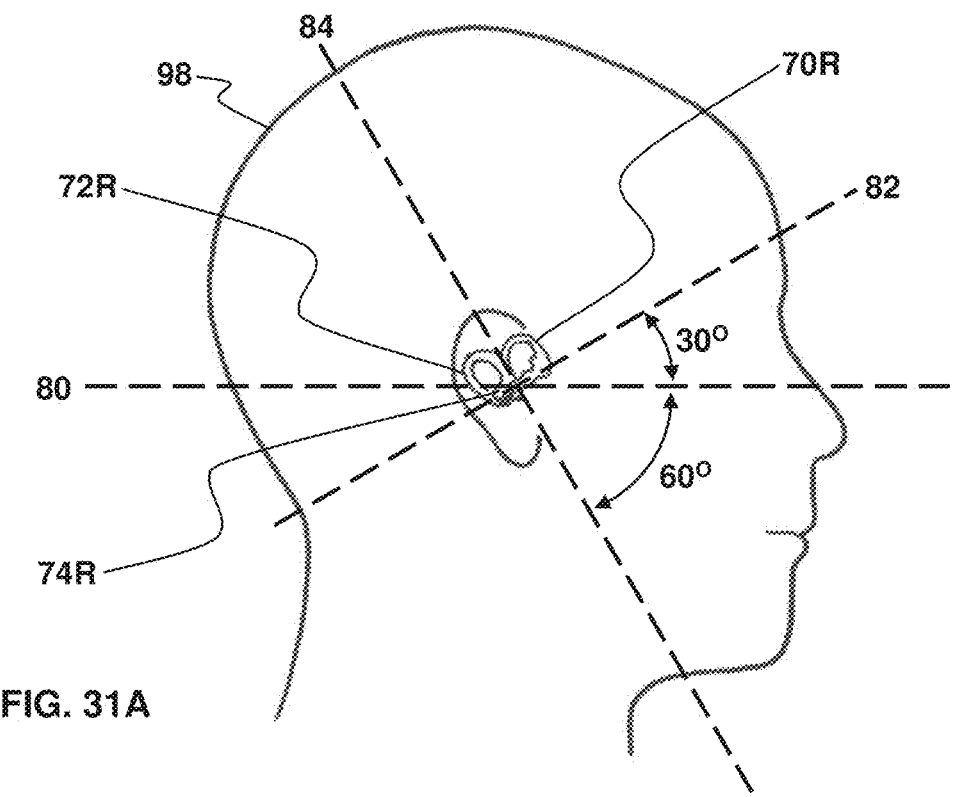
FIG. 31A shows a side view and FIG. 31B shows a top view of the orientation of the semicircular canals in the inner ear (e.g., labyrinth)
Figure 31B:
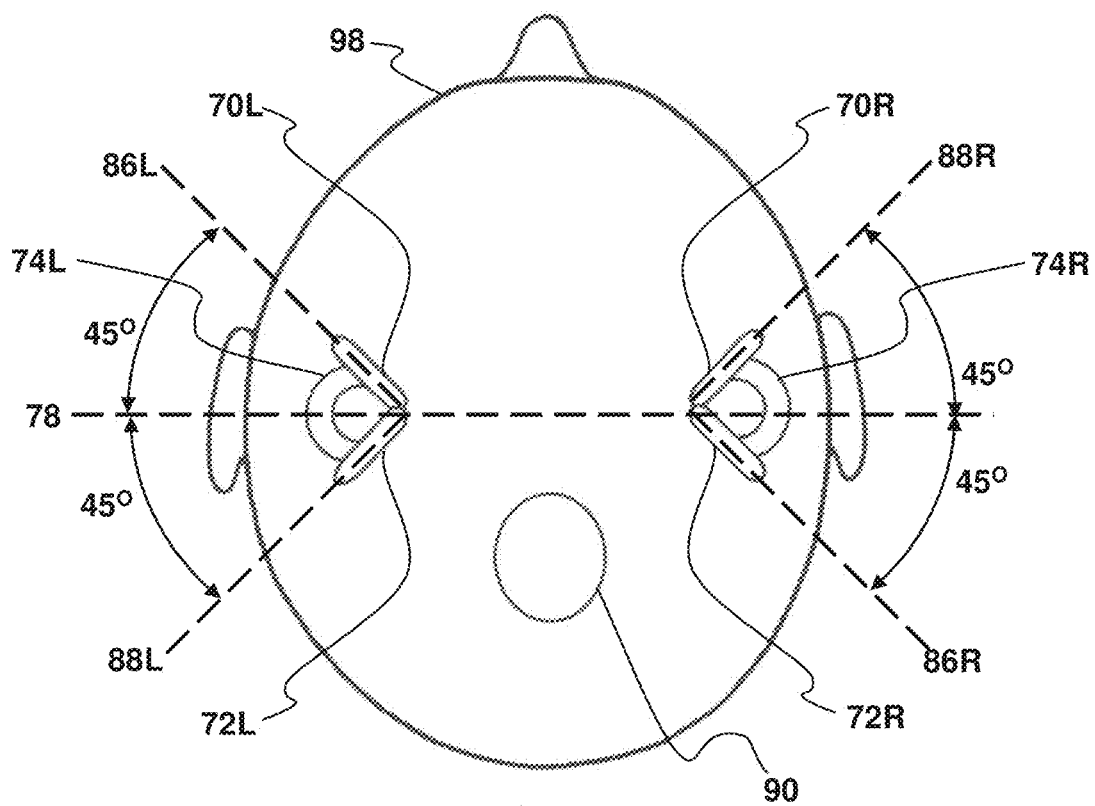

FIG. 31A and FIG. 31B show features and orientation of the vestibular apparatus of each ear, located in the temporal bone of the head 98. The foramen magnum (center of rotation of the head and top of spine) is at 90. The vestibular apparatus comprises three semicircular canals on each side of the head, oriented in different planes. Two vertical semicircular canals are on each side of the head: (1) the anterior semicircular canals, 70R and 70L, (also known as the superior canals) and (2) the posterior semicircular canals, 72R and 72L, (also known at the inferior canals). On each side of the head, there is (3) one horizontal semicircular canal, 74L and 74R (also known as the lateral canal). As shown in FIG. 31B, the vertical canals (72R, 72L, 70R, and 70L) are oriented in planes (86L, 86R, 88L, and 88R) at 45 degrees in relation to the coronal plane 78. As shown in FIG. 31A, the horizontal semicircular canal plane 82 is tilted upward about 30 degrees anteriorly from the horizontal plane 80 (also known at the naso-occipital plane). As shown in FIG. 31A, the plane of the saccule 84 is perpendicular to the horizontal semicircular canal plane 82. The vertical canals form two canal pairs: the left anterior right posterior (LARP): and the right anterior left posterior (RALP). The left anterior and right posterior planes are illustrated at 86L and 86R and the right anterior and left posterior planes are illustrated at 88R and 88L in FIG. 31B.

Each semicircular canal is maximally sensitive to rotations perpendicular to its canal plane. The maximum sensitivity of the horizontal canal 74 occurs when the head is tilted forward about 30 degrees. Maximum sensitivity of the left anterior canal 70L and the right posterior canal 72R occurs when the head 98 is rotated approximately 45 degrees to the right about a vertical axis (about the foramen magnum 90), and the head is pitched downward and upwards in a plane parallel to the LARP planes (86L and 86R). Maximum sensitivity of the left posterior canal 72L and right anterior canal 70R occurs when the head is rotated approximately 45 degrees to the left and the head is pitched backwards and forwards in a plane parallel to the RALP planes (88R and 88L).

Human health status related to the vestibular apparatus can be determined using the tests described previously with reference to FIG. 11, FIG. 12, FIG. 13, FIG. 14, FIG. 15, FIG. 16, FIG. 19, FIG. 20, and FIG. 21. Eye measurement occurs with the abrupt head rotation in the plane of the canal. One of the measures is the ratio of eye movement response to the head movement stimulus (e.g., the gain of the VOR) for each canal tested. For example, when the head is turned right approximately 45 degrees, a diagonal head pitch forward activates the left anterior canal 86 and causes an upward eye movement, and a head pitch back activates the right posterior canal 86 and causes a downward eye movement. To test these canals, the head impulses must be delivered in the plane of the canal pair under test. However, in these tests, to have a valid measure of vertical VOR, gaze position must be directed along a line in the plane of the stimulated semicircular canal pair.

Figure 32:
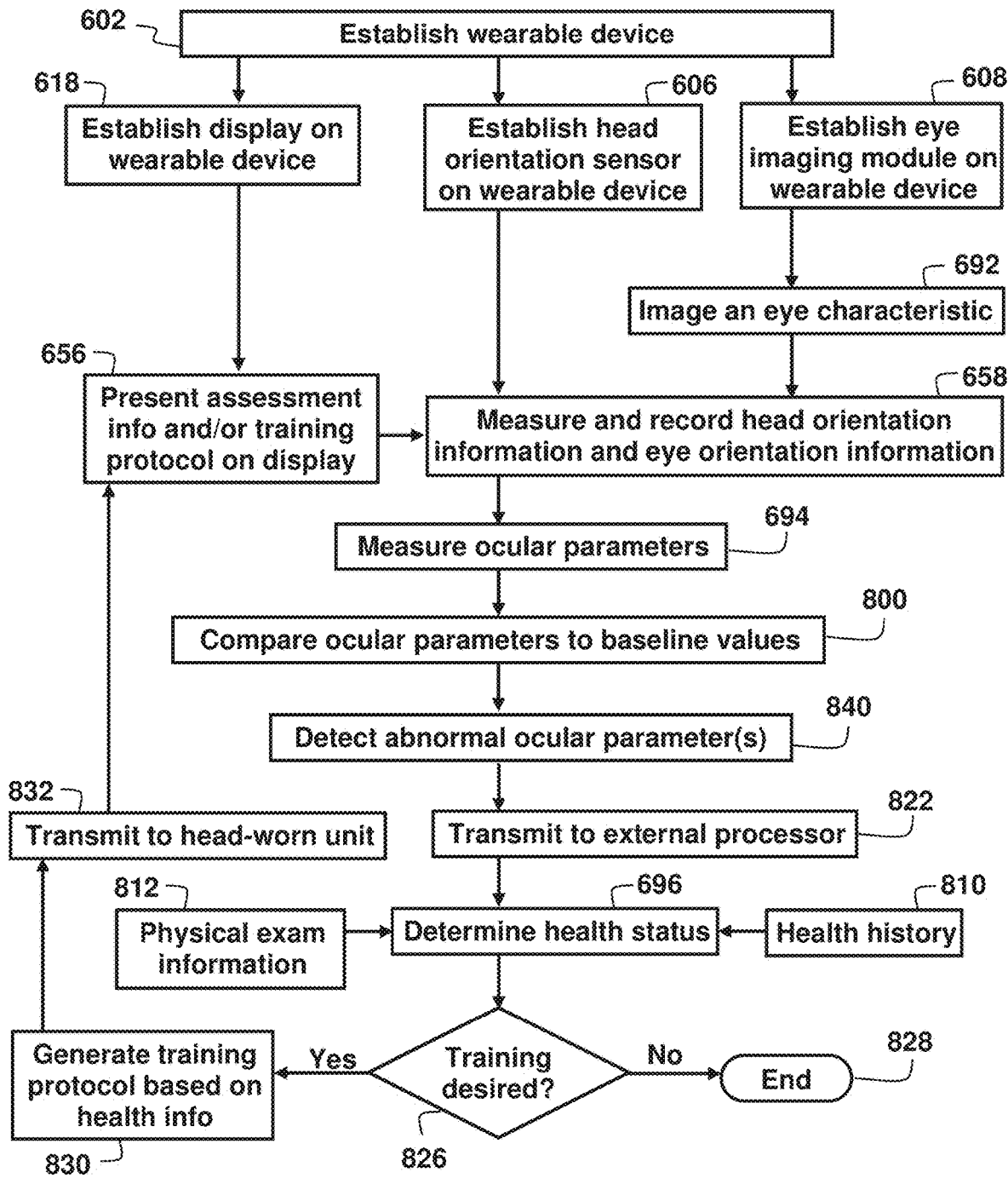
FIG. 32 shows a training, rehabilitation, and/or performance enhancement method.

FIG. 32 shows an example of a test method that uses the human health device as described in this document to provide an electronic prescription, using the measured ocular parameter values for rehabilitation, treatment, or training. This test comprises the following configuration and steps:

- This test uses a wearable device 602 that comprises a display 618, an eye imaging module 608, which images an eye characteristic 692, and a head orientation sensor 606.
- Display: In this test, the visual target being displayed is variable, depending on the target needed for rehabilitation or requested for training. The visual target can be comprised of a target as described in the FIG. 1, FIG. 12, FIG. 13, FIG. 15, FIG. 17, FIG. 18, FIG. 20, and FIG. 21. The visual target in this embodiment is being used to present assessment information and/or training protocol to the user by means of the wearable display as shown at step 656.
- Eyes: The subject is instructed to keep his/her eyes focused on the visual target. The eye imaging module measures eye movement and/or eye position and/or eye orientation changes 658 and is capable of detecting eye movements at frequencies of 0.01 Hz to 20 Hz.

The test sequence is as follows:
1. The first time that the wearable device is used with a subject, the visual target information in step 656 is used to measure the head movement, and or head position and/or head orientation and eye movement and/or eye position and/or eye orientation response, as shown in step 658. Note that step 658 is the same as a combination of step 642 and step 640 shown in FIG. 1 and other tests shown previously.
2. Results from step 658 are used to measure ocular parameters (step 694), which can be any ocular parameter discussed previously including calibration (FIG. 11), saccades (FIG. 12 and/or FIG. 13), vestibular ocular reflex (FIG. 12), vestibular ocular reflex cancellation (FIG. 13), vergence (FIG. 14), smooth pursuit (FIG. 15), nystagmus caused by vestibular stimulation (FIG. 16), nystagmus caused by visual stimulation (FIG. 17), optokinetic nystagmus (FIG. 18), pupillometry (FIG. 19), dynamic visual acuity (FIG. 20), and/or eyelid performance (FIG. 21).
3. The ocular parameters measured in step 694 can be compared to baseline (normal) values for ocular parameters for healthy individuals, as shown at 800 to detect abnormal ocular parameters, as shown at step 840.
4. Abnormal ocular parameter information 840 can then be transmitted to an external processor, step 822, either wirelessly or using a wired configuration, and can be done using a security protocol capable of being understood by anyone skilled in the art. The external processor could be a local computer, or it could be a computer in the internet cloud, or any other processor capable of being understood by anyone skilled in the art. Note that in an alternate embodiment, the processor could be on the wearable device, instead of being external.
5. An external processor can then use the abnormal ocular parameter information 840 in conjunction with physical exam information 812 and health history 810 to determine health status, as shown at step 696.
6. A decision can then be made at step 826, as to whether training is desired. This training could be used for rehabilitation or performance enhancement. Note that this step is similar to step 820 in FIG. 1, where it is labeled as "train for rehabilitation or train for performance enhancement". If the decision is that no training etc. is possible or desired, the process ends, as shown at 828.
7. If it is decided to perform training, a training protocol is generated as shown at step 830 and will be described in more detail later in this document.
8. Training protocol information can then be transmitted to the wearable device, as shown at step 832. More specifically, this training protocol information from step 830 can then be presented on the wearable display, as shown at step 656. This training protocol information can comprise (a) instructions for a human subject to follow, and (b) information of what to present on the wearable display. For example, how the visual target should be displayed and/or should move.
9. Established programs using artificial intelligence and machine learning algorithms (e.g., computer codes) can be stored in the cloud for (a) providing training to normal subjects who want to improve performance to above normal levels with ocular parameters and (b) providing specific visual-oculomotor-vestibular rehabilitation to subjects having abnormal ocular parameters.

Systems and methods for performing visual-oculomotor-vestibular (VOV) rehabilitation can comprise any of the elements and modules described in this document. The display can be a virtual reality display, a see-through display, or any other display capable of being understood by anyone skilled in the art. As an example, VOV rehabilitation could be used for traumatic brain injuries associated with cognitive deficits. VOV can be a specific rehabilitative therapy designed to correct an abnormal ocular parameter measurement detected. For example, for a vestibulo ocular reflex (VOR) abnormality, an individual could be presented with a visual display of a stationary visual target and then asked to rotate the head back and forth in a horizontal and/or vertical manner while focusing on the visual target. This can be repeated, or other variants of the therapy can be presented, depending on the abnormality, until the ocular parameter measurement returns to normal value. The visual target activity can be changed as well as the user head movement for VOV rehabilitation, depending on the abnormal finding of the ocular parameter which was measured. This VOV rehabilitation therapy can be considered a non-pharmacological prescription (e.g., an electronic prescription) used to recover ocular parameter abnormalities. The goal of this rehabilitation using a display with visual stimuli is to use a problem-oriented training approach to promote compensation. This is achieved by customizing exercises to address the specific abnormal ocular parameter detected with each subject. Depending on the abnormal ocular parameter(s) identified, three principal training methods of visual rehabilitation can be prescribed: 1) Habituation Training, 2) Gaze Stabilization Training, and/or 3) Balance Training using the visual display. Habituation Training therapy is indicated for subjects who report increased dizziness when moving, such as quick head movements, or when changing positions. Also, habituation exercise is appropriate for subjects who report increased dizziness in visually stimulating environments. The goal of habituation exercise is to reduce the dizziness through repeated exposure to visual stimuli that provokes patients' dizziness. Gaze Stabilization Training exercises are used to improve control of eye movements so vision can be clear during head movement. These exercises are appropriate for subjects who report problems seeing clearly because their visual world appears to bounce or jump around, such as when reading or when trying to identify objects in the environment, especially when moving. There are different types of eye and head movement exercises used to promote gaze point stability. The choice of the exercise(s) depends on the detected ocular parameter. For example, impairment of the VOR can be improved by targeted gaze-stability training. Gaze stability refers to the ability to hold the eyes on a fixed location while the head is in motion. Gaze-stability training requires a subject to maintain visual focus while moving his or her head and can be used in a variety of different conditions to facilitate recovery from VOR impairment. Alternatively, to improve gaze point stability the head can be moving in the same direction of the visual target, or the head can move in the opposite direction, while in both conditions the eyes remain fixed on the target. For dysfunction of visual motion sensitivity, graded and systematic exposure to visually stimulating environments in the display can be used as a rehabilitative technique to habituate the subject. For subjects with symptoms of positionally induced vertigo, such as with benign paroxysmal positional vertigo, identified with ocular parameter testing like that described related to FIG. 31A and FIG. 31B, different repositioning maneuvers can be performed to help resolve the spinning. Balance Training using the visual display, comprised of instructional exercises, can be used with different visual stimuli to habituate motion sensitivity while ambulating and provide orientation cues. Visual-oculomotor-vestibular therapies, especially those that target specific ocular parameter impairments can also use other screening tools like the Dizziness Handicap Inventory to select the visual training rehabilitation program. This Dizziness Handicap Inventory is a 25-item self-report questionnaire assesses the functional, physical, and emotional effects of dizziness which the subject has experienced. It can also be useful in determining the effectiveness of this rehabilitation.

Further referring to FIG. 32, the human subject's health status, from step 696 could be enhanced to a "supernormal" level with visual training, and/or this health status from 696 could be treated with visual-oculomotor-vestibular (VOV) rehabilitation if an abnormality is detected with any of the ocular parameters. Visual training with repeat ocular parameter methods, can provide an above normal level of eye fixation while performing athletic activities or activities of one's occupation. While VOV rehabilitation is often referred to as a restoration of a visual acuity deficit, it also refers to specific visual tasks to restore ocular parameters which were found to be previously abnormal. Visual-oculomotor-vestibular rehabilitation can be performed with or without a display. If an abnormality is detected with one or more of the specific ocular parameters being tested, a specialized program can be viewed. For example, if an abnormal VOR (vestibular ocular reflex) is detected with a TBI (traumatic brain injury) or other disorder, the individual can receive a VOV rehab program, like the method shown in FIG. 1, but in repetitive fashion, in different directions and with optimizing the visual elements to enhance visual fixation. Effective rehabilitation interventions initiated early after a TBI has been shown to enhance the recovery process and minimize the functional disability. The return of normal ocular parameters can provide a precise risk assessment to guide the determination for return to deployment (RTD) or return to play activities with high performance predictability, based on the ability for return of measured eye movement responses to achieve normal values.

With reference to step 830 in FIG. 32, the training protocol (or training information) is responsive to the ocular parameter measurement from step 694, baseline values (normal values) from step 800, which allow the detection of abnormal ocular parameter 840, and health history information from 810. The following table illustrates more specifically how the abnormal ocular parameters from step 840 can be used to generate the training protocols in step 830 in FIG. 32. This table gives an overview of the behavior of the visual target and instructions for the human subject to follow.

| Abnormal Ocular Parameter | Generated training protocol |
| --- | --- |
| Abnormal saccades | Gaze point stabilization training, which can be combined with balance training to reduce saccadic activity and improve saccade accuracy:<br>a. Visual target enhanced to reduce microsaccades.<br>b. Subject views visual target in center of display, ensuring that head is aligned with target, then views target to left, then right. This can be repeated at different speeds.<br>c. Subject view visual target in center of display, ensuring that head is aligned with target, then views target above, then below. This can be repeated at different speeds. |

-continued

| Abnormal Ocular Parameter | Generated training protocol |
|---|---|
| | d. Subject reads the first letter of words in a paragraph on the display.<br>e. Subject reads vertical strips of letters.<br>f. Balance training tasks, such as standing, or walking can be added while the subject repeats the above tests. |
| Abnormal vestibulo-ocular reflex (VOR) | Targeted gaze stabilization training, which can be combined with balance training with instructional exercises:<br>a. Subject eyes remain fixed on a stationary visual target as the head moves horizontally, then vertically.<br>b. Subject head is stationary with the eyes fixed on a visual target, while the target moves in a horizontal direction, then in a vertical direction.<br>c. Subject head moves in the same direction as the visual target while the eyes remain fixed on the target. This is performed with vertical and horizontal movements.<br>d. Subject head moves in the opposite direction of tire movement of the target, with eyes remaining fixed on the target. This is performed in the horizontal and vertical directions.<br>e. The above exercises (a, b, c, and d) can be performed horizontally, vertically, and in the pane of the abnormal semicircular canal, that has previously been identified with ocular parameter testing.<br>f. The above exercises can be performed at different speeds.<br>g. The above exercises can be performed in conjunction with balance training tasks, while the subject is ambulating.<br>h. Subject can rotate head and trunk together in a horizontal direction while maintaining eye fixation on the visual target. |
| Abnormal vestibulo-ocular reflex cancellation (VORC) | Gaze point stabilization training exercises, which can be combined with balance training:<br>a. Subject eyes remain fixed on a stationary visual target while the head moves. This can be performed with the head moving horizontally and vertically.<br>b. Subject head is stationary with the eyes fixed on a visual target, while the target moves in a horizontal direction, then in a vertical direction.<br>c. Subject head moves in the same direction as the visual target while the eyes remain fixed on the target. This is performed with vertical and horizontal movements.<br>d. Subject head moves in the opposite direction of the movement of the target, with eyes remaining fixed on the target. This is performed in the horizontal and vertical directions.<br>e. Subject is asked to imagine a head-fixed target in darkness during head movements.<br>f. The above exercises can be performed at different speeds.<br>g. The above exercises can be performed in conjunction with balance training tasks, while the subject is ambulating. |
| Abnormal vergence | Gaze point stabilization training exercises, which can be combined with balance training:<br>a. Subject view's an enhanced visual target as the target is moved toward the nose. Subject is instructed to focus on the target.<br>b. The target continues to move toward the nose until double vision occurs. At this point, the target is moved away until the double vision resolves. The distance of the visual target moving away from the nose can vary.<br>c. The target is held stationary for a few seconds while the subject focuses on the visual target and the training exercise is repeated.<br>d. Subject can work on improving this threshold by achieving a closer distance from the nose each time.<br>e. Balance training tasks can be added, such as doing the above exercise while standing with feet together, split stance (one foot in front of the other), or on one foot. |
| Abnormal smooth pursuit | Gaze point stabilization training exercises, which can be combined with balance training:<br>a. Subject views an enhanced visual target as the target is in motion.<br>b. The target in this exercise can move in any direction and at different speeds.<br>c. Subject then focuses on two separate targets, alternating between them in the horizontal plane and/or the vertical plane.<br>d. Subject uses quick eye movements to move the visual focus from target to target in a zig-zag pattern.<br>e. Subject can also focus on visual target motion of a bouncing ball or other visual target object. |
| Abnormal nystagmus with vestibular stimulation | Habituation therapy with goal of reducing the vestibular nystagmus and symptoms of dizziness through repeated exposure to movement stimuli and Gaze stabilization training and balance training exercises: |

| Abnormal Ocular Parameter | Generated training protocol |
|---|---|
| | a. Subject head moves with visual target motion in the display while standing.<br>b. Subject views stationary visual target while standing and turning head side to side, this is repeated with vertical head motion.<br>c. Subject views different visual stimuli to habituate motion sensitivity while ambulating, while orientation cues are provided.<br>d. Subject's head moves in the specific paired planes of the semicircular canals. |
| Abnormal optokinetic nystagmus (OKN, also referred to as OPK test) | Habituation therapy with the goal of reducing symptoms through repeated exposure to visual stimuli that provokes a subject's dizziness: Gaze stabilization training and balance training exercises:<br>a. Subject views visually stimulating environments in the display as a rehabilitative technique to habituate the subject.<br>b. Subject views stationary' visual target to minimize and eliminate optokinetic nystagmus in a moving visual field.<br>c. Subject views different visual stimuli to habituate motion sensitivity while ambulating, while orientation cues are provided.<br>d. Subject can view oscillation of an optokinetic drum or of a light-emitting-diode (LED) stimulus.<br>e. Subject views moving targets, such as railroad cars, vertical visual elements similar to telephone poles, or viewing a cascade of railroad tracks moving vertically.<br>f. Subject watches videos with conflicting visual scenes. |
| Abnormal dynamic visual acuity | Gaze point stabilization training:<br>a. Subject maintains visual fixation on an enhance visual target while moving head horizontally and vertically.<br>b. Subject reads letters written on moving visual targets.<br>c. Subject reads smallest letter displayed while head is in motion. |
| Abnormal pupil performance | Pupil control is balanced between sympathetic and parasympathetic nervous system. Rest and relax eyes. Avoid direct light in eyes, drugs, and alcohol. Different visual stimuli can increase or decrease pupil size. Control conditions or stimuli adversely affecting pupil performance |
| Abnormal eyeblinks | Conscious training of firm blinks can increase the blink rate and alter incomplete blinks. |

Further referring to the table above, it should be noted that dynamic activity (walking or other movement) could be added to any of the above training protocols. Such requested movements could be performed at a prescribed metronomic pace. The above training protocols could be performed by the subject multiple times per day.

Figure 33:
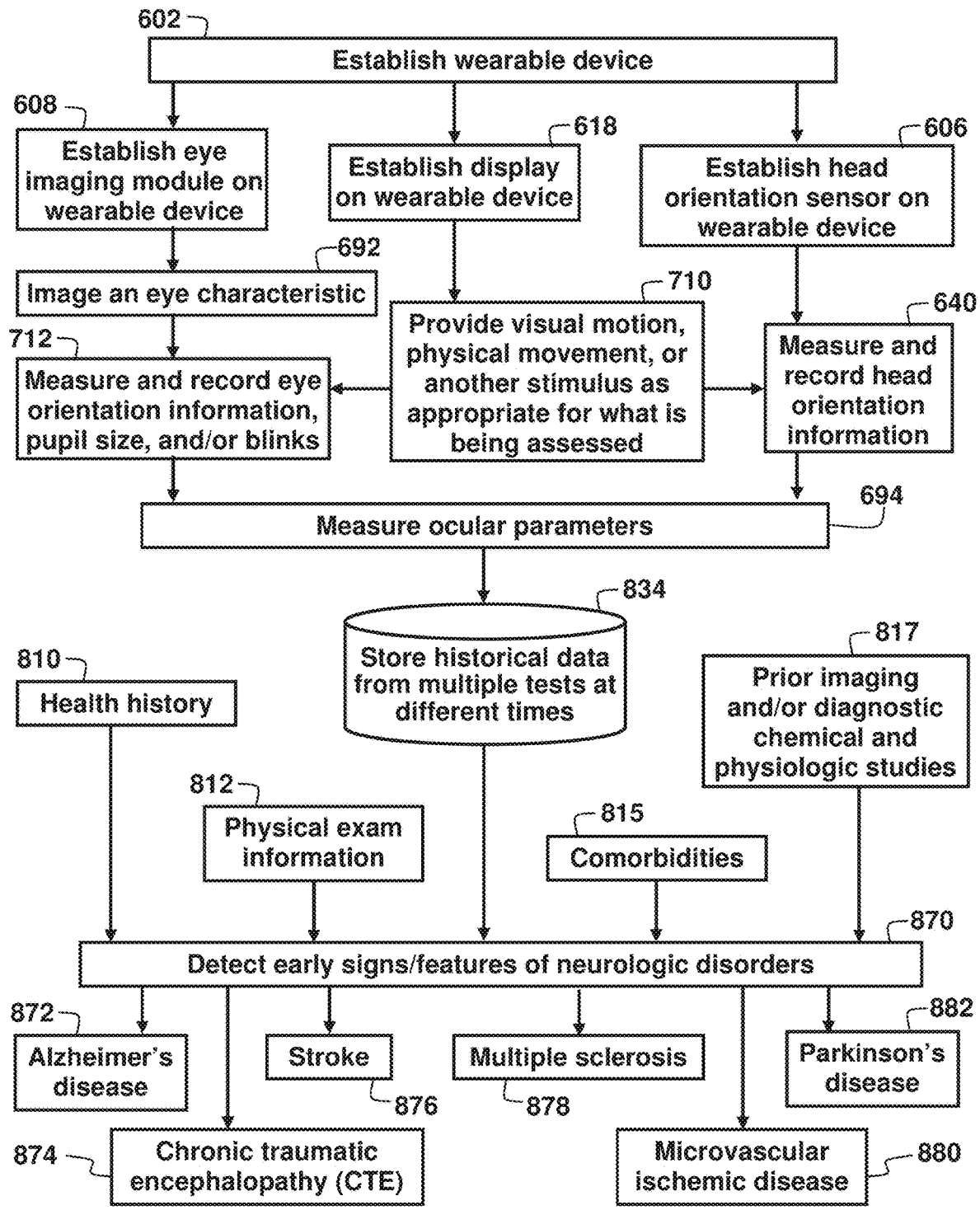
FIG. 33 shows a method for early detection of different neurologic disorders.

FIG. 33 shows an example of a test method that uses the human health device as described in this document to provide data logging of measured ocular parameters to be used for early detection of neurologic disorders, such as chronic traumatic encephalopathy from TBIs, Alzheimer's disease or Parkinson's disease. This test comprises the following configuration and steps:

This test uses a wearable device 602 that comprises a display 618, an eye imaging module 608, which images an eye characteristic 692, and a head orientation sensor 606.

Display: In this test, the visual target being displayed is variable, depending on the target used for ocular parameter evaluation. The visual target can be comprised of a target as described in the FIG. 1, FIG. 11, FIG. 12, FIG. 13. FIG. 14, FIG. 15, FIG. 17, FIG. 18, FIG. 19, FIG. 20, and FIG. 21.

Eyes: The subject is instructed to keep his/her eyes focused on the visual target. The eye imaging module measures eye movement and/or eye position and/or eye orientation changes and is capable of detecting eye movements at frequencies of 0.01 Hz to 20 Hz.

The test sequence is as follows:
1. A wearable display presents a visual target appropriate to the ocular parameter being measured.
2. The subject is instructed to focus on the visual target and will either move the head or keep the head stable 710, depending on the ocular parameter measured.
3. The eye imaging module measures and records the eye changes, during the specific ocular parameter being evaluated (step 712) and the head orientation sensor measures and records the head movement, and or head position and/or head orientation (step 640).
4. Ocular parameters (e.g., saccades, VOR, VORC, etc) can be measured (step 694).
5. The ocular parameters, as well as raw head movement, and or head position and/or head orientation data from step 640 and eye data from step 712 is then stored, as shown at step 834.
6. Over time, the ocular parameter(s) can be repeated and each time the recorded data is logged (step 834). This data can also be compared to baseline values for normal human health, for example.
7. When the ocular parameter testing (step 694) detects an abnormality, compared to baseline values, this can trigger a process for detecting early signs and/or features of neurologic disorders, as shown at step 870. In addition to the logged historical data (834) and this detection step 870, the following can be used as additional inputs: patient history and symptoms (810); physical exam information (812), an assessment of any comorbities (815); and a review of any prior imaging, diagnostic chemical, or physiologic studies (817).

8. Among the neurocognitive disorders that can be detected in this way are Alzheimer's disease (872), chronic traumatic encephalopathy (874), strokes (876), multiple sclerosis (878), microvascular ischemic disease (880), and/or Parkinson's disease (882).
9. The detection of the early health-related biomarkers (signs/features) 870 of these neurologic diseases can provide early intervention with treatment to delay symptoms and prevent disability.

Figure 34:
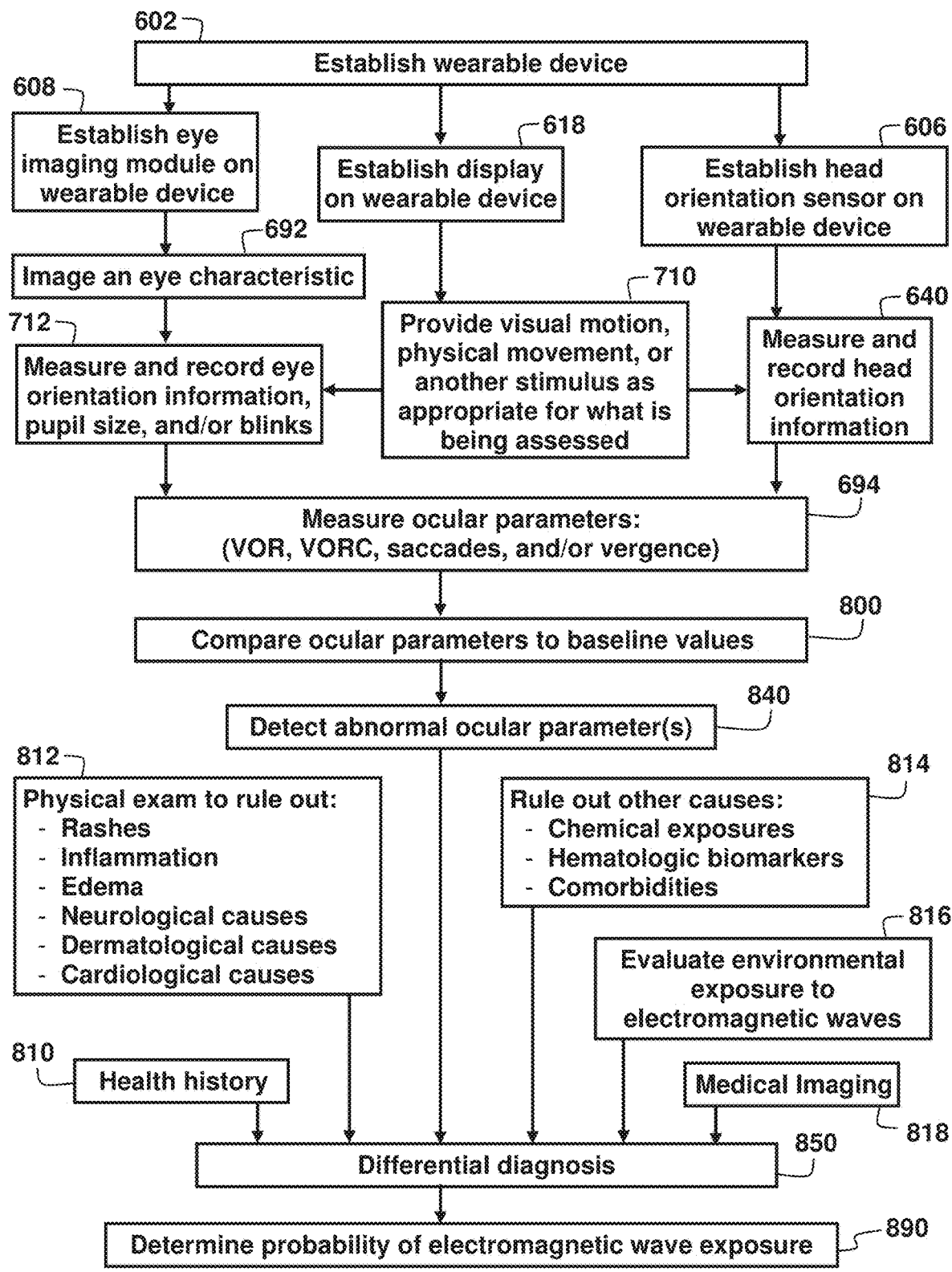
FIG. 34 shows a method for assessing electromagnetic wave exposure.

FIG. 34 shows an example of a test method using the human health device as described in this document to detect the harmful effects of electromagnetic wave exposure, such as vestibular disturbances and cognitive deficits. This test comprises the following configuration and steps:

This test uses a wearable device 602 that comprises a display 618, an eye imaging module 608, which images an eye characteristic 692, and a head movement, head position and/or head orientation sensor 606.

Display: In this test, the visual target being displayed is variable, depending on the target used for ocular parameter evaluation. The visual target can be comprised of a target as described in FIG. 1, FIG. 12, FIG. 13, and FIG. 14.

Eyes: The subject is instructed to keep his/her eyes focused on the visual target. The eye imaging module measures eye movement and/or eye position and/or eye orientation changes and is capable of detecting eye movements at frequencies of 0.01 Hz to 20 Hz.

The test sequence is as follows:
1. The wearable display presents a visual target appropriate to the ocular parameter being measured.
2. The subject is instructed to focus on the visual target and will either move the head or keep the head stable 710, depending on the ocular parameter measured.
3. The eye imaging module measures and records the eye changes 712, during the specific ocular parameter being evaluated and the head movement, and or head position and/or head orientation sensor measures and records the head motions (step 640).
4. Ocular parameters are measured and recorded (step 694). Note that in this case, only vestibular ocular reflex (VOR), vestibular ocular reflex cancellation (VORC), saccades, and/or vergence are of interest.
5. Measured ocular parameters (694) are compared to baseline values (step 800).
6. If an abnormal ocular parameter, or parameters, is detected (step 840), the differential diagnostic process (step 850) can correlate subject's symptoms with: health history and signs (810) including the time and location of symptoms; a physical examination information (812) to rule out conditions such as rashes, inflammation, edema, neurological causes, dermatological causes, and cardiological causes; ruling out other causes (814) such as chemical exposures, hematologic biomarkers, and comorbidities; evaluating potential environmental exposure (816) to radio waves or other electromagnetic fields; and reviewing any prior medical imaging (818).
7. A differential diagnosis (step 850), that comprises the detected abnormal ocular parameter(s), can then determine the probability of electromagnetic exposure (step 890). It is the health history with all symptoms, their occurrences in spatial and temporal terms and in the context of electromagnetic wave or field exposure that is most important for diagnosing this physiologic health impairment.

Figure 35:
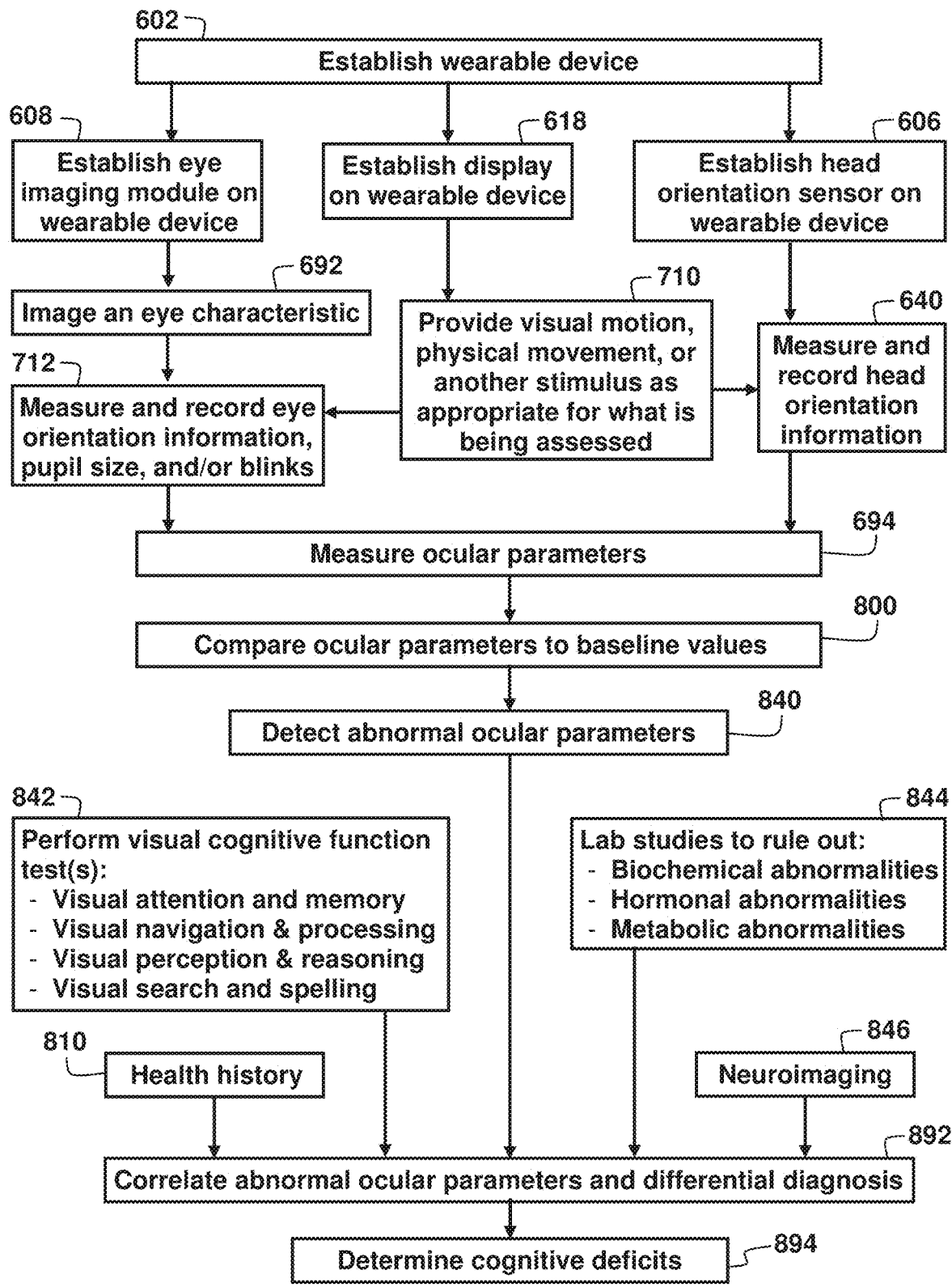
FIG. 35 shows a method for assessing cognitive deficits.

FIG. 35 shows an example of a test method using the human health device as described in this document to detect cognitive deficits, such as impairment of different domains of cognition associated with traumatic brain injury, Alzheimer's disease, Parkinson's disease, and other neurologic disorders. This test comprises the following configuration and steps.

This test uses a wearable device 602 that comprises a display 618, an eye imaging module 608, which images an eye characteristic 692, a head movement, head position and/or head orientation sensor 606.

Display: In this test, the visual target being displayed is variable, depending on the target used for ocular parameter evaluation. The visual target can be comprised of a target as described in the FIG. 1, FIG. 11, FIG. 12, FIG. 13. FIG. 14, FIG. 15, FIG. 16, FIG. 20, and FIG. 21.

Eyes: The subject is instructed to keep his/her eyes focused on the visual target. The eye imaging module measures eye movement and/or eye position and/or eye orientation changes and is capable of detecting eye movements at frequencies of 0.01 Hz to 20 Hz.

The test sequence is as follows:
1. The wearable display presents a visual target appropriate to the ocular parameter being measured.
2. The subject is instructed to focus on the visual target and will either move the head or keep the head stable 710, depending on the ocular parameter measured.
3. The eye imaging device measures and records the eye changes (step 712) during the specific ocular parameter being evaluated (step 694), and the head orientation sensor measures and records the head movement, and/or head position and/or head orientation (step 640).
4. Processor: The processor in the system can measure the ocular parameters (e.g., saccades, VOR, VORC, etc) in step 694. The ocular parameter measures at step 694 are compared to baseline values 800 to detect any abnormal ocular parameters at step 840. The detected abnormal ocular parameters 840 can be analyzed and correlated with the visual cognitive function tests 842, laboratory studies 844, health history 810, and neuroimaging studies 846 to establish a differential diagnosis 892 for determining accurate cognitive deficits at step 894. The visual cognitive function tests (842) can include visual attention and memory, visual navigation and processing, and/or visual search and spelling. Laboratory studies (844) are performed to rule out biochemical abnormalities, hormonal abnormalities, and/or metabolic abnormalities; and neuroimaging (846) can image the central nervous system to determine any pathology. The health history in this instance is comprised of present and past medical history, family history, social history, and medications used. The accumulated diagnostic information from step 840, 842, 844, 810, and 846 all aid in the accuracy of the differential diagnosis 892 and identification of cognitive deficits 894.

Regarding step 842 in FIG. 35, there can be numerous visual cognitive function tests performed with visual targets on a display. Examples include:
(a) In this document and appended claims a visual attention test can evaluate the duration of sustained attention by asking the subject to count or otherwise mentally keep track of sequentially presented visual information. For example, the subject is asked to count the number of odd numbers presented over 1-2 minutes. Auditory distractors can be used to make the tasks more complicated.

(b) In this document and appended claims a visual memory test can present visual information to a subject for a brief period of time (~5 seconds) and requests that the subject encode as much information as possible. Memory can be tested by having the subject blink twice (as an example) when an item is presented that was in the previous display. The reaction time and errors are recorded.

(c) In this document and appended claims a visual navigation test can use maps or mazes to evaluate a subject's ability to execute smooth pursuit of eyes, the cognitive abilities of following directions, and quickly identifying visual targets. The reaction time and errors are also recorded. For example, the subject is asked to visually move from one numbered circle to another and identify each before moving on to the next target.

(d) In this document and appended claims a visual processing test can assess numerous cognitive processing issues. A visual discrimination test assesses cognitive difficulties seeing the difference between two similar letters, shapes, or objects. For example, the subject may mix up letters, confusing d and b, or p and q. A visual figure-ground test assesses cognitive difficulties identifying a shape or character from its background. The subject may have trouble finding a specific piece of information on a page. A visual sequencing test assesses cognitive difficulty telling the order of symbols, words, or images. The subject may struggle to write answers on a separate sheet or skip lines when reading. The subject may also reverse or misread letters, numbers, and words. A visual spatial test assesses cognitive difficulties telling where objects are in space. This includes determining how far things are from them and from each other. It also includes objects and characters described on paper or in a spoken narrative.

(e) In this document and appended claims a visual perception test assesses the ability to see and interpret (analyze and give meaning to) the visual information that surrounds us. An example is Figure Ground (Foreground-Background Differentiation). This is the ability to focus on a selected target and screen out or ignore irrelevant images, and associations between the objects.

(f) In this document and appended claims a visual reasoning test can assess the process of analyzing visual information and being able to solve problems based upon it. A person's visual reasoning abilities are related to overall intelligence. It is a component of nonverbal intelligence, meaning that a person does not have to use language in order to solve visual problems.

(g) In this document and appended claims a visual search test can use patterns of varying complexity on the display, and the subject must scan the visual field and find specific target items. For example, the subject views a display with numerous colored dots and must count the pink dots. The reaction time and errors are recorded.

(h) In this document and appended claims a visual spelling test can also use a display of the alphabet, and the subject fixates on particular letters to spell words in response to questions or to initiate conversation. The complexity of the responses and the ability of the subject using memory to retain the earlier parts of words spelled is evaluated.

Figure 36:
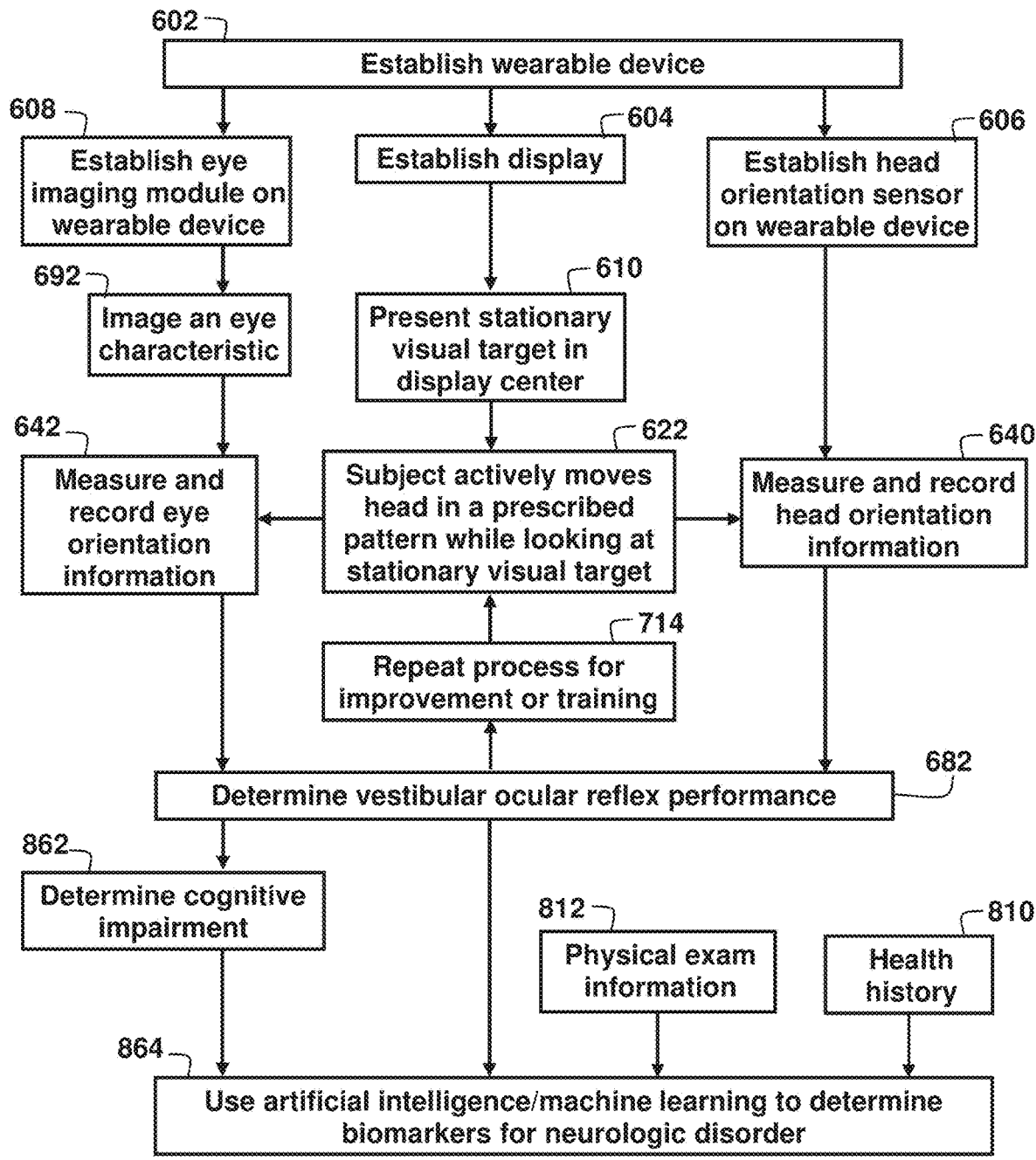
FIG. 36 shows a system that uses artificial intelligence, machine learning, and/or health-related biomarkers to detect a neurologic disorder.

FIG. 36 shows an example of an ocular parameter test method, such as the vestibular ocular reflex, that uses the human health device, as described in this document, to determine health-related biomarkers for neurologic disorders using artificial intelligence and machine learning. This test comprises the following configuration and steps:

This test uses a wearable device 602 that comprises a display 604, an eye imaging module 608, which images an eye characteristic 692, and a head orientation sensor 606.

Display: In this test, the display is stationary—neither the background nor the visual target of interest moves or changes in any way. The display comprises a subdued background and a centered white circular dot or other visually enhanced visual target, as shown at step 610.

Head: In this test, the subject is asked to actively move his/her head, in a prescribed pattern at varied velocities, each time he/she is given a cue signal, as shown at step 622. Each semicircular canal can be separately evaluated for vestibular ocular reflex by having the subject rotate the head in a specific prescribed pattern.

Eyes: The subject is instructed to keep his/her eyes focused on the stationary visual target as the head is moved in a prescribed pattern by the subject. The eye imaging device module measures eye movement, in the opposite direction as the head movement, at step 642. This eye movement measurement in step 642 includes the measurement of overt and covert saccades.

Cues are provided to tell the subject when to move the head. These cues can be audio cues. The cues could be haptic (i.e., vibration on the side of the person's head). The cues could be visual (i.e., change of color or intensity of the visual target of interest). The cues are typically timed randomly so the subject doesn't try to anticipate the timing.

The test sequence is as follows:

1. A stationary visual target is established on the display, as shown at step 610.
2. The subject actively moves the head in a prescribed pattern while looking at the stationary target, as shown at step 622. Examples of prescribed patterns, for assessment of each semicircular canal, can include those previously discussed in FIG. 12.
3. While step 622 is being performed by the subject, eye movement, and/or eye position and/or eye orientation changes, including overt and covert saccades are recorded, as shown at step 644.
4. Also, while step 622 is being performed by the subject, head orientation changes are being recorded, as shown at step 640.
5. Eye position, and/or eye movement, and/or eye orientation responses are measured, recorded, and at step 642 and compared with each other
6. Responses from each eye and head orientation changes are compared and the vestibular ocular reflex performance is determined, as shown at step 682.
7. If a vestibular ocular reflex abnormality is determined the process can be repeated 714, with 622, 642 and 640 for improvement or training.

Processor: The processor in the system compares the head orientation changes from step 640 to the eye movement and/or eye position and/or eye orientation changes of each eye 642, to determine vestibulo-ocular reflex performance, as shown at step 682. Performance can be measured as accuracy, gain (amplitude ratio of eye to head movement), phase (the timing response for the eye and head position), symmetry, eye, and head velocity, and/or saccade movement. These measurements can determine a cognitive impairment 862, and when combined with the physical examination 812 and human health history 810, health-related biomarkers can be determined to detect neurologic disorders at step 864 with the use of artificial intelligence and/or machine learning. The health history is comprised of present and past medical history, social history, medications, prior laboratory studies and imaging studies.

The health-related biomarkers for neurologic disorders can include those for Alzheimer's disease, Parkinson's disease, traumatic brain injuries, Multiple Sclerosis, as well as others discussed. Early detection of health-related biomarkers at step 864 for a neurologic disorder can provide more rapid intervention with pharmacological treatment, visual rehabilitation treatment, or other therapy to delay symptoms and prevent disability.

FIG. 37 shows an example of an ocular parameter test method, such as vestibular ocular reflex cancellation, that uses the human health device, as described in this document, to rehabilitate a person when a human health abnormality has been detected or to train for performance enhancement using health-related biomarkers identified by artificial intelligence and machine learning. This test comprises the following configuration and steps:

This test uses a wearable device 602 that comprises a display 604, an eye imaging module 608, which images an eye characteristic 692, and a head orientation sensor 606.

Display: In this test, the visual target being displayed for vestibular reflex cancellation is moving. The motion of the visual target can be horizontal, vertical, rotary, sinusoidal or a combination of any motion.

Head: In this test, the subject's head is moving with the visual target in the same direction. The intent is to maintain fixation of the eye while the visual target and head are both in motion (e.g., in the same direction and having the same speed), as shown at step 628. The head orientation sensor measures changes in head pitch, roll, and/or yaw 640.

Eyes: The subject is instructed to keep his/her eyes focused on the moving visual target as the head moves. The eye imaging module measures eye movement at step 644.

This eye movement measurement in step 644 includes the measurement of overt and covert saccades.

The test sequence is as follows:
1. The visual target initiates movement on the display in a selected pattern of motion, as shown at step 620.
2. The subject is instructed to move the head in the same direction as the visual target in order to follow the visual target at the same velocity and time, as shown at step 628.
3. The process can be repeated as needed at step 714 for performance enhancement training or rehabilitation improvement, and at varying speeds.
4. This test can be conducted in the vertical, horizontal, rotary, sinusoidal or a combination of directions.

Processor: The processor in the system compares the head orientation changes from step 640 to the eye movement and/or eye position and/or eye orientation changes of each eye 644, and to the target movement 620, to determine vestibulo-ocular reflex cancellation performance, as shown at step 684. Performance can be measured as accuracy of eye movement/position relative to target movement/position, gain (amplitude ratio of eye to head movement), phase (the timing response for the eye and head position relative to target motion), symmetry of both eyes following the moving target, eye and head velocity compared to target velocity, and/or saccade movement. These measurements can determine a cognitive impairment 862, and when combined with the physical examination 812 and human health history 810, health-related biomarkers can be determined for neurologic disorders at step 864 with the use of artificial intelligence and machine learning. The health history is comprised of: present and past medical history, social history, medications, prior laboratory studies and imaging studies. For those neurologic disorders determined at step 864, training for rehabilitation or for performance enhancement can be completed at step 820.

FIG. 38 shows an example of a test method using the human health device as described in this document to train for rehabilitation or train for performance enhancement.

This test comprises the following configuration and steps:
This test uses a wearable device 602 that comprises a head orientation sensor 606, a display 604, and an eye imaging module 608, which images an eye characteristic 692.

Display: In this test, as shown at 638, the visual target being displayed is variable, depending on the target used for ocular parameter evaluation. The visual target can be comprised of an image previously described for assessment of saccades, VOR, VORC, vergence, smooth pursuit, nystagmus, pupil performance, DVA, and eyelid performance.

Eyes: The subject is instructed to keep his/her eyes focused on the visual target. The eye imaging module images an eye characteristic 692 and measures eye movement and/or eye position and/or eye orientation at step 642 and is capable of detecting eye movements at frequencies of 0.01 Hz to 20 Hz.

Head: A head orientation sensor 606 is on the wearable device 602, and measures and records head pitch, roll, and/or yaw orientation information 640. Depending on the ocular parameter assessed, the subject's head may remain stationary or in motion. Even when not required for motion, the head orientation device 606 is used to measure any head orientation changes, and ensures the head remains motionless during the ocular parameter being measured.

The test sequence is as follows:
1. The wearable display presents a visual target appropriate to the ocular parameter being measured.
2. The subject is instructed to focus on the visual target and will either move the head or keep the head stable depending on the ocular parameter measured.
3. The eye imaging module images an eye characteristic 692 and measures and records the eye changes (step 642) during the specific ocular parameter being evaluated (step 694), and the head orientation sensor measures and records the head movement, and/or head position and/or head orientation (step 640).
4. Ocular parameters (e.g., saccades, VOR, VORC, etc) can be measured (step 694).

Processor: The processor in the system compares the measured ocular parameters (694) to baseline values (step 800). If an abnormal ocular parameter(s) is detected (step 840), an abnormal oculomotor deficit and/or neurocognitive deficit 718 can be detected when combined with visual cognitive function testing 842, which initially detects an abnormal visual cognitive function at step 716. The combined physical exam information 812, health history 810, and detected neurocognitive deficit and/or oculomotor deficit 718 can determine the neurologic disorder 804 present. The health history is collectively comprised of: the present and past medical history, social history, medications taken, prior laboratory and imaging studies. Once a neurologic disorder is determined, visual rehabilitation or performance enhancement training 820 can be instituted. Regarding step 842, there can be numerous visual cognitive function tests performed with visual targets on a display as previously discussed in FIG. 35.

FIG. 39 shows an example of a test method using the human health device as described in this document to categorize health status differences and determine the pharmacological intervention effects on the measures of ocular parameters for individuals having neurologic disorders and/or physiologic impairments and/or biochemical impairments.

This test uses a wearable device 602 that comprises a display 618, an eye imaging module 608, which images an eye characteristic 692, a head movement, head position and/or head orientation sensor 606.

Display: In this test, the visual target being displayed 690 is variable, depending on the target used for ocular parameter evaluation. The visual target can be comprised of a target as described in the FIG. 1, FIG. 11, FIG. 12, FIG. 13, FIG. 14, FIG. 15, FIG. 16, FIG. 20, and FIG. 21.

Eyes: The subject is instructed to keep his/her eyes focused on the visual target. The eye imaging module 608 measures eye movement and/or eye position and/or eye orientation 642 and is capable of detecting eye movements at frequencies of 0.01 Hz to 20 Hz.

Head: A head orientation sensor 606 is on the wearable device 602, and measures and records head pitch, roll, and/or yaw orientation information 640. Depending on the ocular parameter assessed, the subject's head may remain stationary or in motion. Even when not required for motion, the head orientation device 606 is used to measure any head orientation changes, and ensures the head remains motionless during the ocular parameter being measured.

The test sequence is as follows:
1. The wearable display 618 presents a visual target 690 appropriate to the ocular parameter being measured.
2. The subject is instructed to focus on the visual target and will either move the head or keep the head stable depending on the ocular parameter measured.
3. The eye imaging module images an eye characteristic 692 to measure and record the eye position, eye movement, and or eye orientation (step 642) during the specific ocular parameter being evaluated (step 694).
4. The head orientation sensor measures and records the head movement, and/or head position and/or head orientation (step 640).
5. Ocular parameter measurements are generated at step 694

Processor: The processor in the system compares ocular parameter measurements generated (step 694) to baseline values (step 800). If an abnormal ocular parameter(s) is detected (step 840), this abnormal ocular parameter can detect a health-related biomarker 860, when combined with the physical exam information 812 and health history 810. Health-related biomarkers 860 can then categorize health status differences 697 to determine normal health 802, neurologic disorders 804, biochemical impairments 806, and/or physiologic health impairments 808. Upon establishing the category of human health status 698, a determination is made regarding normal health 724, and if a disorder or impairment is determined, pharmacological intervention 720 can be provided and the method for assessing response or efficacy to the pharmacologic intervention can be repeated at step 714. This can be repeated as often as necessary to assess effectiveness of drug therapy 722, appropriate drug dosage or modification of pharmacologic therapeutics in the treatment of a neurologic disorder and/or biochemical and/or physiologic impairment. When normal health is determined to be present no further testing or therapy is needed at step 828.

There can be numerous other embodiments, capable of being understood by anyone skilled in the art, using the above-described figures which use eye and head orientation sensors for measurement of ocular parameter to determine human health status, including neurologic disorders, such has traumatic brain injury and neurocognitive deficits; biochemical health impairments, such as alcohol and drug use; and/or physiologic health impairments, such as motion sickness, fatigue, spatial disorientation, and vertigo.

Ocular Parameter Measurement for Human Health Assessment

The measurement of eye fixation ability while performing visual tasks, can provide a rapid method to detect normal human health, concussions (traumatic brain injuries), and other human health neurologic disorders, physiologic or biochemical impairments. Such ocular parameters include saccades, vestibulo-ocular reflex, vestibulo-ocular reflex cancellation, vergence, smooth pursuit, nystagmus dynamic visual acuity, pupil size, and/or eyeblinks. As has been shown, these measurements are used to assess different areas of the brain and each disorder or impairment can adversely affect a specific brain region, the vestibular system, or its connections (e.g., the neural tracts and pathways).

Some health disorders or impairments are associated with abnormal eyelid performance, such as eyeblinks, and can be detected by measuring the eyelid movements. Specific health issues can affect different neurologic pathways and hence different movements of the eyelids. For example, facial paralysis prevents eyelid closure because the orbicularis oculi muscle, which is innervated by the seventh cranial nerve, severely impairs blinking but does not alter the vertical eyelid movements. Eyelid performance (eyeblink frequency and timing) can be measured to detect cognition, physiologic impairments, (such as attention deficits and fatigue), and biochemical impairments (such as with hypoxia and hypercapnia). Eyelid performance can accurately be measured with a portable wearable device with the systems and methods discussed in this document, with an XR display or without a display using natural visual targets. In a preferred embodiment, eyelid performance, such as the frequency, amplitude, latency, duration, and timing of eyeblinks, can determine the human health status.

Ocular parameter measurement can be combined with head motion measurement for human health assessment. Head motion is virtually constant with our everyday activities. It is present with sports and with all our activities of daily living, including speaking, reading, breathing, and eating. The only time our head is not likely to be completely motionless is when the head is held in a rigid head frame. Observing objects or visual information in our visual field is most often associated with head motion. Additionally, many individuals have involuntary head movements. Genetics can have a close relationship with involuntary head movement. Other common causes of involuntary head movement can include traumatic brain injuries, strokes, brain tumors, diseases related to thyroid hormone secretion, degenerative disorders like Parkinson's disease, untreated syphilis and others. Our ocular parameters function naturally with head motion while performing everyday activities. The clinical method of testing some parameters, such as smooth pursuit, with the head placed in a head frame is unnatural and will not provide real-life measurements. To understand how an individual performs with ocular parameter measures in real-life or natural environments and determine the human health status, eye and head tracking should both be utilized.

The vestibulo-ocular reflex (VOR) is generated by head motion and produces eye movements in the opposite direction, while the individual is viewing a stationary target. This allows the visual image to remain stable on the retina so that the VOR gain (eye velocity/head velocity) is equal to unity (gain=1.0). The stimuli during rotational testing of the head can be passive or active impulses or sinusoidal rotations. Impulse rotations demand a rapid acceleration (usually about 100°-150°/s/s) to a constant speed and, after the vestibular provoked nystagmus fades away, a sudden stop during which the nystagmus is again recorded. Sinusoidal rotations are performed by rotating the patient's head or body from side to side so that head movement recordings appear as a series of sine waves. The frequency of the rotations refers to the number of turns per second and is expressed in Hertz. By convention, measurement of the VOR in rotational testing is expressed in terms of gain and phase shift, which is an offset in the timing of eye movement relative to head motion. A gain of 1.0 and a phase shift of 180° indicate perfect VOR, i.e., the eyes move synchronously with head movement but in the opposite direction. The VOR is at its best during head oscillations or rotations of 2 to 6 Hz as encountered in natural locomotion but is less efficient at the extremely low frequencies of head movement. In active head rotation, the subject's head is rotated from side to side horizontally or vertically, as described in this document, at frequencies ranging from 0.1 to 20 Hz. Eye movements and head movements are recorded using sensors discussed in this document attached to the head. At frequencies from 1.0 to 5.0 Hz, VOR gain is not significantly affected whether the head motion is active or passive. This is especially true if an auditory signal indicating the command for moving the head is random. The VOR allows for eye movements in the opposite direction of head movement to maintain steady gaze and prevent retinal image slip. Motion signals from the utricle, saccule, and/or semicircular canals in the inner ear (e.g., vestibular portion of the labyrinth) travel through the utricular, saccular, and/or ampullary nerves to areas in the vestibular nucleus, which sends output to cranial nerve III, IV, and VI nuclei to innervate the corresponding muscles. The VOR is an ocular parameter, which is very useful in detecting abnormalities of human health and can be an accurate measurement to predict human performance ability when motion is present. An abnormal VOR can include overt and/or covert saccades while an individual rotates the head, and it can indicate bilateral, complete, or severe (>90%) loss of vestibular function. In the technology discussed in this document, a display, such as XR, can be used to provide enhanced visual target(s) for the individual to view while the head is moving. The VOR assessment can be performed in a natural environment without a display and viewing natural elements or targets while the head is in motion. This can easily be performed with sufficiently high scan rate using eye sensing technology, such as opto-electric transducers, and scanners which can rapidly convert eye information into electrical signals and transmitting this to photodectors. In a preferred embodiment, the VOR can determine the human health status and detect neurologic disorders, like TBIs, Multiple Sclerosis, biochemical impairments, which occurs with alcohol use, and/or physiologic impairments, such as spatial disorientation, and/or exposure to electromagnetic waves because such impairments affect the associated VOR neural tracts and pathways.

Vestibulo-ocular reflex cancellation (VORC) occurs when the visual target and head are both moving in the same direction, ideally with the same angular velocity. The vestibulo-ocular reflex (VOR) mechanism triggers eye movements, as a result of head motion, in order to keep gaze stationary relative to the world. However, in order to shift the direction of the gaze along with head motion, the VOR mechanism must be overridden ("cancelled"). Two separate mechanisms provide VOR suppression during eye-head pursuit, that is to overcome the vestibular drive that would move the eyes away from the target of interest. The first is the cancellation of the VOR by a smooth pursuit signal based on a cerebro-ponto-cerebellar neural pathway. The second suppression mechanism is a partial, parametric reduction of VOR gain (eye velocity/head velocity). These pathways point to the complexity of regulation of the VOR suppression, involving a large network of brain areas and, therefore, being vulnerable to the risk of age and brain lesion-associated deficits of this movement. The VORC can also accurately be measured with a portable wearable device with the systems and methods discussed in this document, with an XR display or without a display using natural visual targets. In a preferred embodiment, the vestibulo-ocular reflex cancellation can determine the human health status, including neurologic disorders like TBI, biochemical impairments, which occurs with alcohol use, and physiologic impairments, such as dizziness, because such impairments affect specific anatomic regions and neural tracts and pathways of the brain related to VORC.

The rapid eye movement of saccades cannot consciously be controlled. After gazing on a moving target of interest, which was initially motionless, it takes about 200 milliseconds for eye movement to begin. During this delay, the position of the target with respect to the fovea is computed, and the difference between the initial and intended position, or "motor error", is converted into a motor command that activates the extraocular muscles to move the eyes the correct distance in the appropriate direction. If the target moves again during this time (which is in the order of 15-100 milliseconds), the saccade will miss the target, and a second saccade must be made to correct the error. While visual information is not processed during saccadic eye movements, they still can provide information about viewing behavior. According to the theory of visual hierarchy a stimulus is inspected by scanning it through a sequence of visual entry points. Each entry point acts like an anchor, which allows the user to scan for information around it. According to this perspective, longer duration of saccadic eye movements could indicate increased cognitive effort in finding a suitable entry point into a visual display. One reason for the saccadic movement of the human eye is that the central part of the retina (known as the fovea) plays a critical role in resolving objects. By moving the eye so that small parts of a scene can be sensed with greater resolution, body resources can be used more efficiently. The saccade that occurs at the end of a head turn with someone who has an abnormal VOR is usually a very clear saccade, and it is referred to as an overt saccade. An overt saccade can be indicative of abnormal semicircular canal function on the side to which the head was rotated. Covert saccades are small corrective saccades that occur during the head movement of a person with abnormal inner ear function. Covert saccades reduce the need for overt saccades that the end of the head movement and are more difficult to identify than overt saccades. Covert saccades are very fast. This makes them almost impossible to detect by the naked eye, and therefore sensitive eye tracking measurements are typically required to detect covert saccades. There is a rapid deceleration phase as the direction of sight lands on the new target location. Following a very short delay, large saccades are frequently accompanied by at least one smaller corrective saccade to further approach a target location. Corrective saccades can occur even if the target has been made to disappear, further supporting the projected, ballistic nature of saccadic movements. However, corrective saccades are more frequent if the target remains visible. Saccade accuracy, latency, duration, frequency, and velocity for a plurality of saccades can be measured with oculomotor eye movements, such as smooth pursuit, and vestibulo-ocular movements. Saccades can be elicited voluntarily, but occur reflexively whenever the eyes are open, even when fixated on a target. They serve as a mechanism for fixation, rapid eye movement, and the fast phase of optokinetic nystagmus. The rapid eye movements that occur during an important phase of sleep are also saccades. For saccadic amplitudes up to 15 or 20°, the velocity of a saccade linearly depends on the amplitude (the so-called saccadic main sequence). Saccade duration depends on saccade amplitude. In saccades larger than 60 degrees, the peak velocity remains constant at the maximum velocity attainable by the eye. In addition to the kind of saccades described above, the human eye is in a constant state of vibration, oscillating back and forth at a rate of about 60 Hz. Saccades are important ocular parameter measurements used to detect numerous health disorders, or impairments and can accurately be measured with a portable wearable device with the systems and methods discussed in this document, with an XR display or without a display using natural visual targets. In a preferred embodiment, saccade measurement can determine the human health status, including neurologic disorders, like TBI and Parkinson's Disease, physiologic impairments, including deficits caused by electromagnetic wave exposure and motion sickness, and biochemical impairments, such with electrolyte deficits and organic solvents because such impairments affect the related saccade neural tracts and pathways.

When we shift our point of gaze from a far object to a near object, such as with vergence, our eyes converge, the lenses of our eyes modify their focus (accommodate), and our pupils often constrict. The mechanism and control of vergence eye movements involves complex neurological processes that can be compromised in individuals with traumatic brain injury, thus frequently resulting in a wide range of vergence dysfunctions and related near-work symptoms, such as oculomotor-based reading problems. Vergence requires that the occipital lobes be intact, and the pathway involves the rostral midbrain reticular formation (adjacent to the oculomotor nuclei) where there are neurons that are active during vergence activities. It comprises a complex and finely tuned interactive oculomotor response to a range of sensory and perceptual stimuli. There is an important interaction between the vergence system and vestibular labyrinth (e.g., inner ear balance organs) system. To keep the eyes focused on a visual target or object of interest, while the head is moving, the vestibular labyrinth system senses head rotation and linear acceleration which activates the eyes to counterrotate to keep gaze constant even though the head is moving. Measuring the ocular parameter vergence is important as it can be adversely affected not only by concussion or traumatic brain injury (TBI) but also by factors including aging, drug use, visual abnormalities and with some other physiologic impairments. Vergence can accurately be measured with a portable wearable device with the systems and methods discussed in this document, with an XR display or without a display using natural visual elements. In a preferred embodiment, measures of vergence can determine the human health status, including neurologic disorders like TBI, physiologic impairments, including deficits caused by electromagnetic wave exposure, and biochemical impairments, such with drug use because these disorders or impairments affect the anatomic region and neural tracts and pathways related to vergence in the brain.

Pupillometry entails the measurement of minute fluctuations in pupil diameter in response to a stimulus and assessment of pupil measures includes the pupil characteristics previously discussed. The size of the pupil is controlled by the activities of two muscles: the circumferential sphincter muscle found in the margin of the iris (innervated by the parasympathetic nervous system), and the iris dilator muscle, running radially from the iris root to the peripheral border of the sphincter (which contain $\alpha$-adrenergic sympathetic receptors that respond to changes in sympathetic tonus and changes in the blood level of circulating catecholamines). The pupillary light reflex is an autonomic reflex that constricts the pupil in response to light, thereby adjusting the amount of light that reaches the retina. Pupillometry can accurately be measured with a portable wearable device with the systems and methods discussed in this document, with an XR display or without a display using natural visual elements. In a preferred embodiment, pupil measurements can determine the human health status, including neurologic disorders, such as Alzheimer's disease and strokes, physiologic impairments, including decreased attention and cardiac deficits, and biochemical impairments, such as with drug use, because such impairments affect the neural tracts and pathways related to pupil performance and activity.

Smooth pursuit, the eye movement in which the eyes remain fixated on a moving object, is an important ocular parameter measurement for detecting neurologic disorders and/or biochemical and physiologic impairments. Smooth pursuit can also be accurately measured with a portable wearable device with the systems and methods discussed in this document, with an XR display or without a display using natural visual elements. In a preferred embodiment, measures of smooth pursuit can determine the human health status, including neurologic disorders, like TBI, and microvascular brain disease, physiologic impairments, including motion sickness, spatial disorientation, deficits caused by electromagnetic wave exposure, and biochemical impairments, such with drug and alcohol use because these disorders or impairments involve the smooth pursuit neurologic tracts and pathways in the central nervous system.

The rhythmic eye movement of nystagmus is comprised of a slow eye movement driving the eye off the target followed by a second movement that brings the eye back to the target and can be comprised of various waveforms.

Nystagmus can accurately be measured with a portable wearable device and the systems/methods discussed in this document, with or without a display. In an embodiment, nystagmus can detect the human health status, including neurologic disorders, such as strokes, and physiologic impairments, including motion sickness, spatial disorientation, and dizziness because these disorders or impairments can affect the area and pathways in the central nervous system associated with occurrence of nystagmus.

When optokinetic nystagmus (OKN) occurs, the initial eye movement is a smooth pursuit movement followed by an opposite saccade back to the primary gaze or direction of visual interest and when the optokinetic system is activated, a perception of self-motion, (i.e., vection) occurs. The neural pathways for optokinetic nystagmus include the smooth pursuit pathway and accessory optic system. This ocular parameter measure is used detect visual and neurologic disorders and can be measured with a portable wearable device with the systems and methods discussed in this document, with or without a display using natural visual elements. In a preferred embodiment, OKN can determine the human health status, including neurologic disorders, like brain tumors of the rostral midbrain, or optic nerve lesions, biochemical impairments with metabolic abnormalities involving the cortex, brainstem and/or cerebellum, and physiologic impairments, such as inner ear or labyrinthine impairments, because such disorders or impairments affect the associated OKR neurologic tract and pathway.

Infectious diseases can adversely affect ocular parameters. For example, Covid 19 has been associated with demyelination of the optic nerve, pupillary changes, and cranial neuropathy affecting cranial nerves III, IV and VI, resulting in paresis. In an embodiment, such impairments can be detected by pupil movement, VOR, DVA and vergence because of the affected neurologic pathway.

FURTHER EMBODIMENTS

In one embodiment, the head worn device can be comprised of an XR display device with at least one affixed eye imaging sensor and head orientation sensor discussed herein with an electronic circuit. The eye imaging sensor can be configured to generate an electrical image in response to eye information received from the eye sensor and the head orientation sensor can be configured for generating an electric head orientation signal in response to head movement or head information. The eye information can include horizontal, vertical and tortional eye movements and eye position, pupil size and movement activity information as well as eyelid movement information, including eyeblink frequency, amplitude, latency, duration, and timing. The eye imaging sensor and head orientation sensor can be responsive to the display. The eye imaging sensor can be comprised of an eye imaging device (e.g., module) constituted of at least one opto-electric transducer. This eye imaging device can convert a light signal into an electric signal and configured to image the eye characteristics or surface characteristics of the eye and/or the eyelid performance. The imaging device can image the eye a plurality of times to create a moving image of the eye or surface of the eyes. The electronic circuit can be responsive to the eye imaging device electric signal and the head orientation electronic signal. The eye information received from the imaging device electric signal can be compared to information received from the head movement, and or head position and/or head orientation electric signal to determine the measured differences. This embodiment can be configured to determine human health status, including those associated neurologic disorders, physiologic and biochemical impairments from the measured eye information responses and measured head information responses and the different measures between the eye sensor and head orientation sensor.

In another embodiment, the system discussed herein can be comprised of artificial intelligence (AI) or train a machine learning-based model used for detecting the eyelid position based on the eye surface characteristic reflections, extracting eyelid positions by analyzing the images (image-based positions), generating data points based on the image-based positions: generating digital values based on the reflections: and providing the data points and digital values to train the machine learning based model for detecting the eyelid position based on the eye surface reflections.

In another embodiment, the discussed system above can also comprise a forward-facing camera, configured to transmit video information, and which can communicate with the electronic circuit, eye imaging sensors and head orientation sensor. This can be used to determine location of eye fixation, identify and correct slippage offsets of the head worn device.

In another embodiment, the system described can be comprised of physiologic and biochemical sensors, which are in contact with the skin to provide biochemical and physiologic information from the body, which can communicate with the electronic circuit, eye sensors, head sensors and the recorded data from the physiologic and biochemical sensors can be correlated with the ocular parameter measures.

In an embodiment, the present invention can be comprised of a device which uses eye and head information to measure ocular parameters to determine human health. The eye information can be acquired from an eye sensor that is comprised of at least one opto-electric transducer configured for converting a light signal to an electrical signal and the head information can be acquired from the head orientation sensor comprised of an IMU. The head orientation sensor and eye imaging sensor(s) can be integrated into the wearable device. The system described is configured for measuring the position and movement responses of the eyes and head. The head orientation sensor senses pitch and yaw of the person's head in a range of frequencies that comprises at least one frequency greater than 0.01 Hertz and less than 20 Hertz. The head movement, and/or head position and/or head orientation sensor can be comprised of one or more accelerometer(s), magnetometer(s), and/or gyroscopes.

In the embodiments discussed herein, features including a forward-facing camera, extended reality (virtual reality or augmented reality) display, eye imaging device, head orientation sensor controlled by an electronic circuit. Components of the electronic circuit can be activated or controlled haptically, auditorily, remotely, wirelessly, with gestures or movement of the eyes, head, hands or manually with a power switch on the head worn device. Additionally, a bone or air conducting sensor can be incorporated in the framework of the head worn device which can provide auditory/acoustic signals to issue an input signal to a controller to operate the system. The electronic circuit can also be activated by placing the head worn device on the head which can issue a similar input signal w % ben in contact with the skin and when removed from the head, the system will automatically become deactivated.

In an embodiment of the device, the system may include the user interface for providing information to the user of the device. The user interface may be associated with displayed images, a touchpad, a keypad, buttons, a microphone, a haptic device, and/or other peripheral input devices. The processor may control functions of the system based on input received through the user interface. The system and/or testing function controls and input connections can be in a wearable device and/or in a remote device. The computing system could be a distributed computing system. The computing system could comprise cloud computing. The ocular parameter measure methods can be comprised of an application connected to a cloud-based artificial intelligence infrastructure. The application can be made up of a series of tasks, and a user's eye movement can be recorded in data sets called Eye Movement Biomarkers (EMBs) and Gaze Mapping Biomarkers (GMBs).

In an embodiment, the head worn system can include a gyroscope, a global positioning system (GPS), magnetometer, and an accelerometer. The head worn eye and head tracking system may be configured to provide information associated with a position and an orientation to the processor. The gyroscope may include a micro-electromechanical system (MEMS) gyroscope or a fiber optic gyroscope as examples. The gyroscope may be configured to provide orientation information to the processor. The GPS unit can include a receiver that obtains clock and other signals from GPS satellites. The GPS unit can be configured to provide real-time location information to the processor. The head worn system may further include an accelerometer configured to provide motion input data to the processor.

In one embodiment, the head worn device or method can present a visual target to one eye (monocular) or both eyes (binocular). A power source can be attached to the head worn device and which can be rechargeable by a wireless interface.

In another embodiment, the head worn device described herein can measure information between position and orientation of the head and eye position, and/or movement and/or eye reflexes and the ocular parameter being assessed. The data acquired can be processed by the head worn device and displayed to the user or collected data can be transmitted wirelessly to a smart phone, electronic device, or other computer source for the processing and viewing.

In an embodiment, the head worn display system can include an eye imaging and measuring system, a connected head orientation and measuring system, a power supply, a micro-processor, a memory, and a user interface. Components of the system may be configured to work in an interconnected fashion with each other and/or with other components coupled to respective systems. For example, the power supply may provide power to all the components of the system. The processor may receive information from all the affixed sensors and control the eye imaging system and the head movement, position and/or orientation system. The processor may be configured to execute program instructions stored in the memory unit and to generate a display of images on the user interface. The display to the user can be presented as a 2D or 3D (3 dimensional) extended reality (virtual reality or augmented reality) display.

In another embodiment, the head worn system can have a manual control operating switch with an active and inactive mode. It can provide real-time feedback on the display screen, has the capability to display time and can be adjusted to fit users of different statures. It can be comprised of an imaging device, a head orientation sensor, physiologic sensors, biochemical sensors, an electronic circuit comprising a central processing unit with memory unit and a display system which can project visual targets to the user for measuring various ocular parameters. It can also comprise an auditory input for testing instruction, signaling randomized head movement, and serving as an auditory distractor for some visual cognitive tests. Auditory signals can be presented to either ear, indicating the direction for the head to rotate. Visual instructions can also be displayed regarding information to complete the ocular parameter testing. Collected data can be transmitted to a small electronic device where easily understandable results can be seen.

In another embodiment, a cognitive deficit can be determined by an abnormal ocular parameter and/or an abnormal cognitive function test from a group of neurocognitive assessment tools including attention, memory, navigation, processing, perception, reasoning, search, and spelling tests.

In an embodiment, neurocognitive training and/or cognitive feedback can be performed and measured by comparing the eye position and/or movement between each eye, between the position and/or movement of the head and eyes, between the position and/or movement of the eyes and displayed target visualized and between the position and/or movement of a natural scene target and eyes.

In embodiments of the invention, the imaging device can comprise components configured to provide images of eye position and eye movement using characteristics or surface characteristics of the eye. The components can include a light source, diffracting elements to alter the light source, and opto-electric transducer configured for converting the light signal to an electrical signal. A head movement, and or head position and/or head orientation sensor can be configured to generate electrical signals in response to head information and both the imaging device and head orientation sensor components can be electrically coupled such that eye information can be compared to head orientation signals with ocular parameter measurements.

In another embodiment, the extended reality display can be part of a face shield and may allow the wearer to view images in one or both eyes and can allow a view of the real-world environment while providing superimposed virtual images. The eye imaging device and head orientation sensor described in this document may be integrated into the electric circuit with a data storage and logging recorder.

In another embodiment, two or more eye imaging devices can be configured in a complementary fashion to increase eye sensor accuracy. Imaging devices can be configured from the following group: imaging devices of the same type across different focal lengths, imaging devices of the same type across different angular locations and/or imaging devices of differing types to provide composite images.

In another embodiment, the imaging devices can be attached to or mounted within the structural member(s) of a face shield/visor. At least one of the imaging devices can be positioned at a sight plane below the inferior margin of the upper eyelid. It is below the upper eyelid to more easily visualize the pupil, cornea, iris, or other characteristics of the eye used for eye tracking and measurement. Above this plane of sight, the eye sensor would have difficulty tracking the eye movements, due to obstruction of the upper lid and eyelashes.

In an embodiment, the human ocular performance measuring system can be comprised of an eye imaging device, attached to the head worn device, and configured to measure eye movement responses using different techniques of eye imaging measurement including, but not limited to use of one or multiple eye imaging devices, or simultaneous use of different types of eye imaging devices for eye tracking. In another embodiment, at least one eye imaging device can track one or more different locations simultaneously on the surface of one or both eyes (e.g., cornea, pupil, limbus, sclera) or image characteristics from the retina (e.g., optic disc, fovea, *macula*, retina vessels). In another embodiment, the eye imaging device can measure more than one corneal reflection or other eye characteristic using one or more different types of illumination sources simultaneously. In one embodiment, different types of illumination sources can also alternate or combine the type of illumination, depending on the light needed.

In an embodiment, imaging of structural characteristics and functional parameters of the retina can serve as biomarkers using artificial intelligence, for the detection of cognitive impairment. Alternatively, with artificial intelligence driven platforms, eyen retinal vein changes and/or optic disc changes, and/or optic nerve head swelling can serve as biomarkers of intracranial pressure.

In another embodiment, eye imaging devices attached to the head worn unit can be in different positions to acquire different focal points of the eyeball, to achieve more accuracy with eye tracking. Eye imaging devices can also be configured to merge eye movement responses from different imaging devices for more accurate measurement. For example, an imaging device tracking one surface characteristic of the eye can be merged with the same imaging sensor, or another imaging devices attached to a different location on the head worn unit, which is tracking a different eye surface characteristic. The merged data can provide more information regarding gaze and eye movement responses. In embodiments described, eye imaging devices can have multiple functions which enable different measurement characteristics of the eye.

In one embodiment, a single eye imaging device can be used for the eye tracking. In another embodiment, multiple imaging devices are used, and the eye imaging devices can be in different sight planes or located at different distances from the measured area of the eye.

In embodiments of the invention, the light source can be infrared, short-wavelength infrared, near infrared, and/or visible light, such as LED, and can be directed toward one or both eyes. The eye imaging device can be used to detect and measure the reflection of the light source and visible eye characteristics such as the pupil characteristics, cornea reflection characteristics, iris registration characteristics, limbus characteristics, or for retina data imaging. The collected data from the eye imaging device can be used to measure the position and movement features of the eyes or eyelids or orientation of the eye, acceleration/velocity of the eye movement, duration of the eyelid closure, rate of the eyelid closure and the direction of gaze. Additional information such as blink frequency and changes in pupil diameter can also be detected by the eye imaging device. Aggregated eye imaging device data can be written to a file for later analysis. Stored eye imaging device data can be used to analyze the visual path. Eye data information can be translated into a set of pixel coordinates and the presence or absence of collected eye data points in different areas can be assessed. From this information, an analysis can be used to determine which features are seen, when a particular feature captures attention, how quickly the eye moves, what content is overlooked and virtually any other gaze-related data. Eye position can be extracted by the eye imaging device and graphics can be generated on a remote device to visualize the findings. Analysis of visual attention and stored eye data obtained can be examined to measure the cognitive state, fatigue, alertness, or other human health information.

In another embodiment, iris scanning can be used as a controller to turn on a personal device and/or to determine a personal program needed for testing, training or rehabilitation. By scanning the iris, the same device can be used by different individuals, yet personal and private information can be retrieved and/or stored in their own healthcare database.

In other embodiments of the present invention, at least one beam splitter can be used to provide a guide light into the eye. Alternatively, two or more of the single prism beam splitters can be combined to form compound beam splitters that split a single beam of light into three or more different beams of light. A beam splitter can have an optical multi-layer thin film, formed by laminating numerous layers in sequence. The numerous laminated layers can each be comprised of having a different refractive index.

In other embodiment, multiple prisms can be used which can use a corrective optical element to eliminate any deviation or aberrations in the see-though viewing path. For example, in one of its aspects, the invention may include a wedge prism having only planar surfaces. This prism acts as a light guide to supply illumination light to the eye, as well as providing imaging light to the eye imaging device from the illuminated eye. In this embodiment a complementary prism can be arranged with respect to the thin prism such that the two prisms appear to the eye as a plane-parallel plate.

In an alternative embodiment, an eye imaging device can use a free-form prism between the eye and the eye imaging device. The freeform prism can include one or more surfaces with optical power, which are used both for imaging of the eye by the eye imaging device, and for optical aberration control. In certain embodiments, the freeform prism can be used in conjunction with, or exclusive of, additional focusing optics such as an eye imaging device.

In other embodiments, the head tracking can be done from sensors in an electronic device, smart phone, smart pad, from another sensor system attached to a body part, or from a remote device viewed by the user.

In another embodiment, a face shield with eye imaging device attached to the helmet covering the head can be configured for measuring and correcting slippage offsets. The measurement and correction of slippage offsets is carried out by one or more sensors selected from the group of: the existing multi-axis IMU, the existing eye imaging device, an additional IMU, and a wide field of view eye imaging device and/or forward-facing camera.

In one embodiment, the wearable device as discussed herein can be calibrated before it is used. Calibration can also be performed by viewing a visual target on the XR display, focusing on a distant target of interest in the natural environment, viewing a visual target projected by a laser light source which is projected to a distant surface, or viewing a projected holographic image. The static image or visual target can be positioned vertically, horizontally, and centrally. The calibration can be done with the visual target located up to 9 separate points. Typically, several trials can be performed to establish reproducible results. Ideally, the subject is instructed to slowly rotate the head slowly from side to side—horizontally or vertically—in the plane of each semicircular canal being evaluated while viewing the static visual target. Calibration of this type can allow gain, phase, and asymmetry to be accurately measured separately for each canal and at various frequencies. In another embodiment, the individual can be asked to follow an object at a combination of frequencies ("natural tracking") and a Fourier transform or another analysis can be used to convolve the gain, phase, and asymmetry at various frequencies directly from the complex waveform that was being followed by the individual. Natural tracking in the horizontal plane could entail focusing on a natural visual element or target moving across the horizontal visual field. Watching a moving object ascend and descend in the air can serve as a natural vertical test.

Any combination of the discussed embodiments of head inertial trackers and eye imaging systems can be used to measure the ocular movement or reflex response with head movement (e.g., ocular parameters). Alternatively, in another embodiment, the visualized target required to focus upon for the ocular parameter being tested may be displayed, in the natural environment, as an AR, 3D image, hologram or some other light source image. An eye imaging device, using invisible or visible light, simultaneously can be used with head tracking. As the head moves, the eye responses can be tracked and measured by a variety of modalities. In another embodiment, the eye sensor(s) can be comprised of an array of transparent imaging devices based on graphene. In another embodiment, a hologram can be used to blend the digital world with the real world in an attached AR system, to aid in the testing and measurement of the eye movement. This can enable a more immersive see-through multi-dimensional method for all the visual or ocular parameter tests described in this disclosure. A Fourier transform or other method of analysis can be used to compare the inertial head movement and eye movement response information at various frequencies in a complex waveform and software can process the data. The processed information can be displayed remotely to another electronic device and responses can determine the health status of the user and predict potential performance of the user during an activity.

Embodiments of the invention can incorporate physiological and biochemical sensing elements/transducers in contact with the skin for detecting any abnormal physiological or biochemical properties of the user. These sensors can communicate with the electronic circuit and can be correlated with the ocular parameter measured to determine the human health status. This information can also be wirelessly transmitted to a remote electronic device for viewing.

In one embodiment, the vestibulo-ocular reflex can be measured by comparing each of the eye movement and/or eye position and/or eye orientation responses to the head position, movement, and/or orientation, at various velocities, while viewing a stable visual target on a display. Abnormal VOR performance associated with aberrant accuracy, gain, phase, or symmetry, and/or with abnormal saccades can be used to detect neurologic disorders, including TBI, neurocognitive decline, Multiple Sclerosis, microvascular disease, physiologic impairments like dizziness, or deficits caused by electromagnetic exposure, as well as biochemical impairments with alcohol.

In another embodiment, the testing of the vestibular ocular reflex and training for enhancement or improvement is comprised of a system utilizing a head sensor (which measures information such as movement, and/or position, and/or orientation of the head), an eye imaging sensor (which measures information such as movement, and/or position, and/or orientation of the eye), a computer control system with processors, and a display of a stationary visual object. Measurements from the head sensor of a subject's head position while moving the head horizontally and/or vertically, and from the eye imaging sensor while viewing the displayed stationary visual object, generates a statistical analysis of the vestibular reflex of the subject's eye gaze positions relative to the stationary displayed object.

In another embodiment, the testing of the vestibular ocular reflex cancellation and training for enhancement or improvement is comprised of a system utilizing a head movement, and/or head position and/or head orientation measurement device, an eye imaging device to measure eye position and/or movement and/or orientation, a computer control system with processors, a display of a moving visual object across the visual field, measurements from the head orientation measurement device of a subject's head position and/or movement while moving the head horizontally and/or vertically, measurements from the eye imaging device of a subject's eye gaze position and movement while viewing the movement of the displayed visual object, and a method of statistical analysis of the vestibular reflex cancellation which is generated from the subject's eye gaze position and/or movement relative to the moving displayed object.

In another embodiment, the vestibulo-ocular reflex cancellation can be measured, by comparing the eye movement and/or eye position and/or eye orientation changes of both eyes with the head orientation changes, while the subject's head and eyes follows a viewed moving visual target at various velocities on a display. A poor vestibulo-ocular reflex cancellation performance can be indicated by abnormal responses of accuracy, gain, phase (the timing response for the eye and head position), symmetry or latency, and/or with abnormal saccades. Abnormal vestibulo-ocular reflex cancellation performance can detect neurologic disorders such as TBI, Parkinson's Disease and physiologic impairments like motion sickness, dizziness, and electromagnetic effects as well as biochemical impairments with drug abuse.

In another embodiment, the angular vestibulo-ocular reflex cancellation can be measured, comparing the eye movement and/or eye position and/or eye orientation changes of both eyes with the head orientation changes w % bile the subject's head and eyes are following a viewed moving visual target at various velocities and directions on a display. The moving visual target is the stimulus for the head movement and the moving visual target moves in the same planes and direction as the head rotations. In this instance, the head can be positioned downward typically near 30 degrees (for maximal stimulation of the horizontal semicircular canal) and can move alternatively left and right with the viewed moving visual target, at the same velocity, while the eyes remain fixed on the target of interest. The head can also be rotated typically near 45 degrees to the right (for maximal stimulation of the left vertical and right posterior semicircular canal) and can move alternatively downwards and upwards with the viewed visual target which also is moving in the same 45-degree diagonal plane. The head can also be rotated typically near 45 degrees to the left (for maximal stimulation of the right vertical and left posterior semicircular canal) and can move alternatively downwards and upwards with the viewed visual target, which also moves in the same 45-degree diagonal plane at the same velocity. A poor vestibulo-ocular reflex cancellation performance can be indicated by abnormal responses of accuracy, gain, phase (the timing response for the eye and head position), symmetry or latency, and/or with abnormal saccades. Abnormal angular vestibulo-ocular reflex cancellation performance and/or with saccades can determine neurologic disorders such as TBI, Parkinson's Disease and physiologic impairments like motion sickness, dizziness, and electromagnetic effects as well as biochemical impairments with drug abuse.

In an embodiment, ocular parameter measurements can provide an indicator of the response to a pharmacologic therapeutic intervention.

In another embodiment, ocular parameter measurements can provide a neurologic, or physiologic indicator of a response to a therapeutic intervention.

In another embodiment, saccadometry and specifically prosaccade and antisaccade measures can be used to detect neurologic disorders, including cognitive deficits and neurologic disorders.

In an embodiment, vergence can be measured and compared in both eyes, as a visual target in a display appears to move forward and away from the subject's eyes. This movement of the visual target can be a continuous transition, or it can occur in a series of distinct stages. Poor vergence performance can be recorded, indicating abnormal changes of accuracy, convergence, divergence, peak velocity, amplitude, symmetry, or latency, and can be used to determine neurologic disorders, such as TBI, biochemical impairments such as alcohol and drug use, as well as physiologic impairments including electromagnetic effects.

In another embodiment, vergence can be measured during continuous transition of different depths vertically, horizontally, or diagonally as the visual target gets closer or further from the user's eyes combined with dynamic motion of the head, which is moving in the same pattern or direction as the visual target.

In another embodiment, testing of vergence dysfunction is performed for detection and/or quantification of traumatic brain injury, and/or recovery and is comprised of disconjugate movement of the eyes to track objects varying in depth over the binocular visual field.

In another embodiment, saccades can also be measured during other ocular parameter measures including vestibulo-ocular reflex, vestibulo-ocular reflex cancellation, vergence, dynamic vergence, smooth pursuit, dynamic visual acuity, and optokinetic testing. The occurrence of saccades, saccadic intrusions, or saccade dynamics on fixational eye movement during ocular parameter measure can be related to neurologic disorders or other impairments of human health.

In another embodiment, smooth pursuit can be measured while the head remains stable, and the eyes are focused on a visual target which is moving in various 2-D patterns on a display. An abnormal smooth pursuit performance can be indicated by aberrant measured eye movement and/or eye position and/or eye orientation changes of gain (peak velocity/target velocity), velocity changes, accuracy of following a moving object or latency. These abnormalities can determine neurologic disorders like TBI, Alzheimer's Disease, Parkinson's Disease, microvascular disease, physiologic impairments such as motion sickness, electromagnetic effects, and biochemical impairments due to alcohol or hormonal disorders such as diabetes.

In an embodiment, pupil performance can be measured by determining pupil size on each side and features of the pupil, while viewing stationary alternating bright and dim elements on a display. The visual targets can have selective wavelengths, such as with chromatic light and can be presented with various stimulus presentations such as with stepwise increases in intensity or light flashes. Alternatively in another embodiment, these visual targets can be moving toward or away from the eye, or they can be presented in different positions with different characteristics, requiring the subject to recognize the difference between visual targets. Poor pupil performance can include abnormal measures of pupil size, dilation information of acceleration, amplitude, latency or duration, and constriction information of amplitude, latency, or duration. These abnormal pupil measures can detect neurologic disorders like Alzheimer's Disease, Multiple Sclerosis, Stroke, biochemical impairments with drug use and physiologic impairment with cardiac disease, such as hypotension.

In an embodiment, eyelid performance can be measured and compared between each eye by viewing a display with a visual stimulus, at various intensities of brightness, with varied task content and at varying speeds causing eyeblinks. Abnormal eyelid performance can be associated with aberrant velocity of eyeblinks, the duration of eyeblinks, the amplitude or frequency of eyeblinks which can detect the presence of neurologic disorders such as Alzheimer's Disease or neurocognitive deficits, biochemical disorders associated with electrolyte or metabolic abnormalities and physiologic impairments which occurs with fatigue, or lack of alertness.

In another embodiment, a concussion can be detected by presenting a visual stimulus on a display and capturing eye blink raw data from at least of one eye of the subject in response to the visual stimulus using an eye imaging device and analyzing a measure of how often blinks from the eyes over a period of time when subjected to a visual stimulus.

In an embodiment, a concussion can be detected by presenting a visual stimulus on a display and capturing eye blink raw data from both eyes of the subject in response to the visual stimulus using an eye imaging device and analyzing the number of blinks in one eye of the subject that does not have a corresponding blink frequency rate in the other eye of the subject.

In another embodiment, dynamic visual acuity performance can be measured with an eye imaging device to determine eye movement and/or eye position and/or eye orientation while viewing a display of a visual target, which can change attributes, as the head moves horizontally or vertically and establish DVA performance. Abnormal DVA measures of reduced visual acuity, compared to the SVA, can detect neurologic disorders, such as brainstem lesions, and physiologic impairments such as visual and vestibular impairments as well as gaze point stability.

In another embodiment, the presence of abnormal nystagmus as determined by slow-phase velocity measures including duration, frequency, or amplitude and induced by visual stimulation can be used to detect spatial disorientation, motion sickness and dizziness. Alternatively, in another embodiment the abnormal presence of nystagmus with vestibular stimulation can detect neurologic disorders such as stroke and physiologic impairments with the inner ear, such as Meniere's Disease.

In another embodiment, anyone of the ocular parameter measurements, discussed in this document, can be used to determine the status of human health, and implemented for training athletes or other individuals in their occupational activities, to assume a supernormal level of performance.

In another embodiment, skin sensors (positioned over the temporal region) attached to the wearable device and comprised of near-infrared spectroscopy can identify chemical and eyen structural changes in the brain, by comparing the average intensity of diffusely reflected light. These skin sensors can be correlated with the ocular parameter measurement for assessment of a neurologic disorder.

In another embodiment, the human health device as described in this document, including the wearable device, comprised of an eye imaging device, head orientation sensor, display, and electronic circuit can be configured for use with machine learning such that a classifier can recognize any abnormal ocular parameter measured and provide classification of raw gaze datasets, belonging to fixations, saccades, or other predetermined categories. The classified algorithm can be used to determine whether the data can be used for training or specific visual rehabilitation, based on the abnormal datasets, and can modify an attribute of the training or visual rehabilitation according to the measured ocular parameters.

In an embodiment, the system discussed herein can be portable, autonomous, constantly sensing head and eye information with the use of an artificial intelligence (AI) program and classifiers to determine the human health status and can provide this information to the user as well as wirelessly transmit this information to a remote electronic device. In another embodiment, this system can provide an electronic-type prescription for a non-pharmacological treatment alternative with VOV rehabilitation to treat neurologic disorders, physiologic or biochemical impairments affecting the neural tracts and pathways of the abnormal ocular parameter.

In an alternative embodiment, the present invention can visually rehabilitate or retrain the user when a specific ocular parameter abnormality is present. Visual-oculomotor-vestibular rehabilitation can enhance ocular parameter visual accuracy with specific visual stimulation and head movements. VOV rehabilitation can help a user of the device improve the health disorders or impairments by exercising, enhancing, and/or retraining the abnormally detected ocular parameter. This type of rehabilitation system can also provide more rapid recovery of an abnormal ocular parameter by visually stimulating the associated neurologic pathway and connections affected by the neurologic, physiologic, or biochemical deficits with repetitive ocular parameter techniques.

In another embodiment, ocular parameter assessment can be used to train the oculomotor system and brain with individualized program, which can increase accuracy of eye fixation, cognition, attention, reaction time, fatigue, and treat traumatic brain injuries and neurocognitive deficits.

In an embodiment, neurocognitive testing and/or training can be performed with an eye imaging device which measures the right and left eye movement, and/or eye gaze positions, and/or eye orientation during the time a viewed object is moving on a display and measured. Disconjugate measurement between the eyes is compared to detect an oculomotor impairment. A report can be provided if a disconjugate measure is present, indicating the presence of an oculomotor impairment and/or neurocognitive disorder. Disconjugate measures can also be used for training to improve a neurocognitive disorder or oculomotor impairment.

Alternatively, in another embodiment, neurocognitive testing can be performed with an eye imaging device to measure eye movement, and/or eye gaze position, and/or eye orientation. A measured analysis can be generated from the eye measurement information (e.g., eye movement, and/or eye gaze position, and/or eye orientation) of at least one eye can be compared to the position of the object observed by the user. Another measured analysis, representing a physiologic disorder and/or neurocognitive disorder analysis can be generated when there is a difference between eye measurement information and the position of the object viewed by the user.

In another embodiment, an interactive ocular parameter program can be provided which uses image-based interactivities for testing, management, and rehabilitation of concussions/traumatic brain injury with periodic assessment to analyze the progress of neurocognitive deficits. A neurocognitive rehabilitative program can be used with specific neurocognitive disorders. Cognitive testing can also be used for assessing the neurologic status, alertness, fatigability, inattention, deployment readiness, situational awareness, predicting human performance, stress and managing any deficits detected with a visually interactive cognitive program designed to correct those deficits.

In another embodiment, an artificial intelligence health platform can be operable for autonomous operation using a variety of learning methods and/or predictive analytic techniques to determine the health status and/or need for rehabilitation and/or training. The artificial intelligence health platform, comprised of a plurality of different engines, includes neurologic disorders, neurocognitive deficits, physiologic impairments, biochemical impairments, and normal health.

In another embodiment, artificial intelligence (AI) and machine learning can be used analyze the results of ocular parameter assessments, in tandem with visual cognitive function tests discussed herein, patient records and reported symptoms, to diagnose the type and severity of neurocognitive disorders.

In another embodiment, the collected eye and head movement data from ocular parameter measurements of each subject can be logged into an individual database for that subject, to provide a measure of brain health, biochemical and physiological health over a period of time and a machine learning classifier can be utilized to determine patterns to detect disease early and provide early intervention and therapy.

In an embodiment, the information collected from ocular parameter measurement(s) of a user can be logged and transmitted to the medical health care records of the health care provider(s) and/or insurance company.

In another embodiment, the collected eye and head movement data from ocular parameter measurements can use artificial intelligence and machine learning to detect health-related biomarkers related to diagnosing neurologic disorders such as Alzheimer's Disease, Parkinson's Disease, and strokes with abnormalities of cognitive function, mood, and behavior to automatically personalize VOV rehabilitation therapy plans. This VOV rehabilitation therapy can also access the software therapy from the cloud, through a smartphone, or other electronic device. For example, the display can be designed to provide rehabilitation prescriptions to improve specific cognitive visual deficits or cognitive domains. It can provide more immersive experience with engaging visual targets for measuring ocular parameters to assess cognitive function, while quantifying the degree of the cognitive deficit detected. Once the measured ocular parameters determine the health status of the subject, the identity proofing, privacy, and security for the subject can be established. Information regarding normal ocular parameters and/or abnormal ocular parameters can be wirelessly transmitted to the cloud. Artificial intelligence and machine learning in the cloud can establish the rehabilitation program needed for the display, based on the abnormal ocular parameter measured, or further training desired by the subject to obtain above normal performance with selected parameter. The electronic VOV rehabilitation prescriptions can be specifically designed with programs to train a subject to have above normal performance or to treat or train a subject for rehabilitation with a neurologic, biochemical, or physiologic impairment, identified by an abnormal ocular parameter, to a normal health status level.

In another embodiment, the specific electronic prescription, determined by the computer code (machine learning algorithm) in the cloud or other external electronic device, can be transmitted to the trainer/rehabilitation therapist and/or to the subject or to others, such as providers of the subject's health care. Specific programming can also be accessed and actively streamed to the user automatically, upon sensing an abnormal parameter value associated with a particular disorder or the need for training of a specific parameter desired. The subject with normal parameters desiring training can select specific programs to enhance eye fixation with activities to super-normal levels. The subject having an abnormal ocular parameter(s) can be trained with specific visual ocular tasks to rehabilitate the ocular parameter(s) which was abnormal. Eye movement and/or eye position and/or eye orientation changes, pupil size and eyeblinks can be measured with head orientation changes with the VOV rehabilitation tasks or with the visual training tasks. The improvements can be determined by the measured data and wirelessly transmitted back to the cloud for data logging. The use of eye and head movement information described in this document can be valuable in visual-oculomotor-vestibular rehabilitative evaluation, care, management, and long-term planning for anyone suspected as having a neurologic disorder, biochemical or physiologic impairment.

In another embodiment, a system comprised of a display, eye imaging device and head tracking sensor can determine an abnormal ocular parameter, biochemical or physiological impairment of an individual operating an electronic device or vehicle and the abnormality detected can be configured to be transmitted to a computer controller system of the vehicle or other device. Reception of this abnormal sensing data can control the operating systems of the vehicle or device, through artificial intelligence and machine learning.

In an embodiment, this wearable device discussed can function as a health care provider extender to detect and mitigate the long-term physical and psychological sequelae of traumatic brain injuries. This human health device can be comprised of a display to rapidly and accurately provide optimal triage and early intervention with effective rehabilitation treatment for subjects subjected to head trauma. It can transmit the collected head sensor and eye imaging sensor data information, measured while viewing an ocular parameter on the display, to an electronic device remotely and/or to the injured subject. This can provide a key treatment method of early VOV rehabilitation, as well as providing a more accurate strategy in the decision making to guide return to previous activities.

In another embodiment the human health device as described in this document, comprised of a wearable device, eye imaging device, head orientation sensor, and display can be used for assessing a physiologic health impairment from electromagnetic wave exposure.

In an embodiment, the data obtained from the head worn devices and methods described herein can be transmitted by wireless communication to a remote device.

In another embodiment, the raw data collected from the eye imaging sensor(s) and head movement and/or position sensor is transmitted wirelessly, to an external source such as the cloud, or external device for further processing.

In an alternative embodiment, the head worn system can be tethered to a smart phone or computer and use their display or push eye imaging and head orientation responses to these devices.

Embodiments described herein can be used with a protective helmet including those designed for sport activities. Various embodiments can also be used for safety helmets, such as construction or industrial helmets, and helmets used by law enforcement, security and/or military forces.

In another embodiment, eye tracking and/or measurement can also be done with a contact lens. The contact lens can be embedded with electronics and eye motion sensor and can be comprised of a micro-LED display or augmented reality display, a power source with capability of being charged wirelessly. It can also be wireless connected to a smart phone, such as iPhone or another computer device. It can provide an augmented reality experience without a headset attached. Not only can the electronic contacts provide eye tracking but also can visualize biometric, biochemical, and physiologic data from remote wirelessly connected skin sensors.

In another embodiment, a windshield, attached to a vehicle, can be comprised of an eye imaging device, head movement, and or head position and/or head orientation sensor and electronic circuit within the windshield, to detect abnormal ocular parameters, such as eye closure or attention deficits. If an abnormality is detected and measured, the data can be transmitted to the control operating system of the vehicle through AI and machine learning to control the vehicle. The eye tracking sensors can be fixed in a position within the windshield and below the upper eye lid, for eye imaging and head movement, and or head position and/or head orientation sensing. In an alternative embodiment, the eye imaging sensors, can become "locked" on the eyes when starting the vehicle, and subsequently can continuously move to different locations to maintain the locked tracking feature for ocular parameters measurement, while the vehicle is being operated by the user.

In another embodiment, there can be no display affixed to the head worn device, and the visual stimulus for measuring the ocular parameters could originate from viewing natural elements.

In another embodiment, observing the eye and head information as described herein to measure ocular parameters discussed to determine human health can be performed without use of head worn device. For example, this can be performed with an eye imaging device and head orientation sensors embedded in the windshield or affixed to the dashboard or other area facing the operator in a vehicle that can image the eyes and head.

In another embodiment, ocular parameter measurement can be performed with eye sensors (e.g., eye imaging device) and head orientation sensors embedded or affixed to a smart device or smart phone that can image the eyes and head.

Areas of Application

Sports. Embodiments of the invention(s) can be used in sport environments where ocular parameter measurement can help predict player performance, player fatigue, attention, cognition, and early detection of traumatic brain injury. Additionally, if an athlete had such an abnormality and could be given rehabilitation, this can correct the abnormality and allow the athlete to return to play activities sooner. Embodiments of the invention(s) can be used for TBI/concussion management, in which detection, quantification, and monitoring of concussions can be performed with the technology as well as determining when the athlete is safe to return to play, following a concussion, based on the eye movement responses. This technology can prevent the more serious recurrent concussions, especially if they are closely related to the previous concussion. Alcohol and drugs can also adversely affect ocular performance. Embodiments of the invention(s) can be used for drug screen screening and predict player performance based on eye fixation ability.

Military personnel function in a high-level environment and requiring target fixation of their eyes, while performing other activities such as with head or body movement. They require normal ocular parameters, including VOR. DVA, and VORC. If these ocular parameters are abnormal, the soldier will not demonstrate peak human performance. Embodiments of the invention can be used by the military in places such as the pilot selection process or special operations community to aid in the selection of individuals without such an abnormality. This invention can provide immediate training for rehabilitation if an abnormality is detected with ocular parameter measurements. A non-pharmaceutical electronic prescription can be provided from the cloud for rehabilitation, using a visual display as described, and enabling more rapid recovery of abnormal ocular parameters in remote areas or combat zones to improve the health status of the wounded soldier.

Medical. Embodiments of the present invention can be useful to individuals who have experienced symptoms of dizziness, imbalance, unsteadiness, or have had concussions, or other neurologic disorders as described herein. It also can be utilized by centers performing vestibular rehabilitation and athletic/vocational enhancement environments. This invention can provide objective tools for early detection of health-related biomarkers for neurologic disorders, including traumatic brain injury (TBI), the long-term effects of TBI known as chronic traumatic encephalopathy (CTE), biochemical impairments or physiologic impairments which would affect the human health status. In other embodiments, the invention can be used to assess efficacy of pharmacological interventions, especially if given early with some neurologic disorders, such as Alzheimer's Disease, Parkinson's Disease, and others in order to prevent symptoms and mitigate disability.

Commercial. Embodiments can also be used in other industries where individuals are expected to perform in high activity levels, or provocative motion environments. Like the other environments, the invention can predict human health status, such as performance, and can detect neurologic disorders, physiologic and biochemical impairments which affect the neurologic pathway and their connections.

Although the invention herein has been described with reference to embodiments, it is to be understood that these embodiments are merely illustrative of the principles and applications of the present invention. It is therefore to be understood that numerous modifications may be made to the illustrative embodiments and that other arrangements may be devised without departing from the spirit and scope of the present invention as defined by the appended claims.

Further variations and modifications of the disclosed embodiments can also be used. The principles described here can also be used for applications other than sports, military, commercial and medical. While the principles of the disclosure have been described above in connection with specific apparatuses and methods, it is understood that this description is made only by way of example and not as limitation on the scope of the disclosure.

What is claimed is:

1. A system for diagnosing a neurologic condition, wherein:
   the neurologic condition comprises a human health condition from the group of:
      a stroke;
      a traumatic brain injury;
      microvascular ischemic disease;
      Alzheimer's disease;
      Parkinson's disease;
      epilepsy;
      multiple sclerosis;
      a brain lesion;
      amyotrophic lateral sclerosis;
      an effect of alcohol or drugs;
      a metabolic deficit;
      a pulmonary deficit; and
      a cardiac deficit; and
      a deficit related to electromagnetic wave exposure:
   the system comprises a wearable device and a display:
   the wearable device comprises a head orientationسور and an eye imaging module;
   the head orientation sensor is responsive to head orientation information;
   the head orientation information comprises information selected from the group of pitch and yaw of a person's head wherein pitch represents a rotation about a first axis representing up and down movement of the person's face when the rear of the person's head moves in the opposite direction and yaw represents horizontal movement of the person's face when looked at from the front of the person's face about a second axis wherein the second axis is vertical, substantially aligned with the person's spine, and perpendicular to the first axis;
   the eye imaging module is configured for imaging an eye characteristic, wherein the eye characteristic is selected from the group of:
      a retina characteristic;
      a sclera characteristic;
      a cornea characteristic;
      an iris characteristic;
      a limbus characteristic; and
      a pupil characteristic;
   the eye imaging module determines eye position or eye movement information in response to the eye characteristic;
   the display comprises a visual target;
   the system further comprises an electronic circuit;
   the electronic circuit is responsive to the head orientation sensor and the eye imaging module to generate an ocular parameter measurement selected from the group of:
      a saccade measurement;
      a vestibulo-ocular reflex measurement;
      a vestibulo-ocular reflex cancellation measurement;
      a vergence measurement;
      a smooth pursuit measurement;
      a nystagmus measurement;
      a pupil performance measurement;
      a dynamic visual acuity measurement; and
      an eye fixation measurement; and
   the system is configured to diagnose the neurologic condition in response to the ocular parameter measurement from the electronic circuit.

2. The system for diagnosing a neurologic condition of claim 1, wherein:
   the wearable device comprises the display;
   the head orientation sensor comprises an accelerometer and a sensor selected from the group of a magnetometer and a gyroscope;
   the eye imaging module comprises at least one opto-electric transducer configured for converting a light signal to an electrical signal.

3. The system for diagnosing a neurologic condition of claim 2, wherein:
   the display comprises a see-through display;
   the display is responsive to the head orientation sensor;
   the neurologic condition comprises said traumatic brain injury;
   the eye characteristic comprises said pupil characteristic;
   the eye imaging module comprises a video camera;

the eye imaging module is further configured for being responsive to an eyeblink; and the ocular parameter measurement further comprises said saccade measurement.

4. The system for diagnosing a neurologic condition of claim 1, wherein:

the system is responsive to said saccade measurement.

5. The system for diagnosing a neurologic condition of claim 4, wherein:

the imaging module generates an ocular parameter measurement selected from the group of a saccade measurement, a smooth pursuit measurement, a pupil performance measurement; and the neurologic condition comprises said Alzheimer's disease.

6. The system for diagnosing a neurologic condition of claim 1, wherein:

the system is responsive to said vergence measurement.

7. The system for diagnosing a neurologic condition of claim 1, wherein:

the system is responsive to said vestibular ocular reflex measurement; and the neurologic condition comprises said effect of alcohol or drugs.

8. The system for diagnosing a neurologic condition of claim 1, wherein:

the system is responsive to the pupil performance measurement; and the pupil performance measurement comprises a change in a pupil characteristic selected from the group of:
a change in pupil size;
a change in pupil dilation;
pupil response latency; and
pupil response duration.

9. The system for diagnosing a neurologic condition of claim 1, wherein:

wherein the system is further configured for determining the efficacy of a pharmacologic treatment.

10. The system for diagnosing a neurologic condition of claim 1, wherein:

wherein the system is further configured to generate an electronic prescription.

11. The system for diagnosing a neurologic condition of claim 1, wherein:

the neurologic condition comprises said deficit related to electromagnetic wave exposure.

12. The system for diagnosing a neurologic condition of claim 1, wherein:

the system is configured for performance enhancement.

13. The system for diagnosing a neurologic condition of claim 1, wherein:

the system is responsive to said vestibular ocular reflex measurement; and the neurologic condition comprises said traumatic brain injury.

14. A human health system comprising a display, a wearable head orientation sensor, and a wearable eye imaging module, wherein:

the human health system is configured for detecting a neurologic condition;

the neurologic condition comprises a human health condition from the group of:
a stroke;
a traumatic brain injury;
microvascular ischemic disease;
Alzheimer's disease;
Parkinson's disease;
epilepsy;
multiple sclerosis;
a brain lesion;
amyotrophic lateral sclerosis;
an effect of alcohol or drugs;
a metabolic deficit;
a pulmonary deficit; and
a cardiac deficit; and
a deficit related to electromagnetic wave exposure:

the head orientation sensor is responsive to head orientation information;

the head orientation information comprises information selected from the group of pitch and yaw of a person's head wherein pitch represents a rotation about a first axis representing up and down movement of the person's face when the rear of the person's head moves in the opposite direction and yaw represents horizontal movement of the person's face when looked at from the front of the person's face about a second axis wherein the second axis is vertical, substantially aligned with the person's spine, and perpendicular to the first axis;

the eye imaging module is configured for imaging an eye characteristic selected from the group of a characteristic of the retina, sclera, cornea, iris, limbus, or pupil;

the eye imaging module determines eye position or eye movement information in response to the eye characteristic;

the display comprises a visual target;

the system further comprises an electronic circuit;

the electronic circuit is responsive to the head orientation sensor and the eye imaging module to generate an ocular parameter measurement selected from the group of:
a saccade measurement;
a vestibulo-ocular reflex measurement;
a vestibulo-ocular reflex cancellation measurement;
a vergence measurement;
a smooth pursuit measurement;
a nystagmus measurement;
a pupil performance measurement;
a dynamic visual acuity measurement; and
an eye fixation measurement; and the human health system detects the neurologic condition in response to the ocular parameter measurement.

15. The human health system of claim 14 wherein:

the ocular parameter measurement comprises a saccade measurement; and the saccade measurement comprises a measurement selected from the group of saccade accuracy, saccade latency, saccade duration, saccade frequency, and saccade velocity of a plurality of saccades.

16. The human health system of claim 14 wherein:

the eye characteristic comprises said limbus characteristic.

17. The human health system of claim 14 wherein:

the electronic circuit is configured to use a Fourier transform to generate the ocular parameter.

18. A method for determining a neurologic condition, the method comprising the steps of:

establishing a wearable head orientation sensor and a wearable eye imaging module;

establishing a display;

using the wearable head orientation sensor to collect head orientation information from a human subject, wherein the head orientation information comprises information selected from the group of pitch and yaw of a person's head wherein pitch represents a rotation about a first axis representing up and down movement of the person's face when the rear of the person's head moves in the opposite direction and yaw represents horizontal movement of the person's face when looked at from the front of the person's face about a second axis wherein the second axis is vertical, substantially aligned with the person's spine, and perpendicular to the first axis;

using the wearable eye imaging module to image an eye characteristic of the human subject selected from the group of a retina characteristic, a sclera characteristic, a cornea characteristic, an iris characteristic, a limbus characteristic, and a pupil characteristic;

determining eye position or eye movement information in response to the eye characteristic;

presenting a visual target on the display;

using an electronic circuit to generate an ocular parameter measurement in response to information from the head orientation sensor and the eye imaging module wherein the ocular parameter measurement is selected from the group of:
- a saccade measurement;
- a vestibulo-ocular reflex measurement;
- a vestibulo-ocular reflex cancellation measurement;
- a vergence measurement;
- a smooth pursuit measurement;
- a nystagmus measurement;
- a pupil performance measurement;
- a dynamic visual acuity measurement; and
- an eye fixation measurement; and determining the neurologic condition in response to the ocular parameter measurement, wherein the neurologic condition comprises a human health condition from the group of:
- a stroke;
- a traumatic brain injury;
- microvascular ischemic disease;
- Alzheimer's disease;
- Parkinson's disease;
- epilepsy;
- multiple sclerosis;
- a brain lesion;
- amyotrophic lateral sclerosis;
- an effect of alcohol or drugs;
- a metabolic deficit;
- a pulmonary deficit; and
- a cardiac deficit; and
- a deficit related to electromagnetic wave exposure.

* * * * *